(12) United States Patent
Matthews et al.

(10) Patent No.: US 8,663,939 B2
(45) Date of Patent: Mar. 4, 2014

(54) EQUINE PARASITE DETECTION

(75) Inventors: Jacqui Matthews, Edinburgh (GB); Jane Hodgkinson, Wirral (GB); Christopher Proudman, Wirral (GB)

(73) Assignee: Moredun Research Institute, Penicuik, Midlothian (GB)

( * ) Notice: Subject to any disclaimer, the term of this patent is extended or adjusted under 35 U.S.C. 154(b) by 0 days.

(21) Appl. No.: 13/260,935

(22) PCT Filed: Mar. 31, 2010

(86) PCT No.: PCT/GB2010/000616
§ 371 (c)(1),
(2), (4) Date: Dec. 19, 2011

(87) PCT Pub. No.: WO2010/112836
PCT Pub. Date: Oct. 7, 2010

(65) Prior Publication Data
US 2012/0082992 A1    Apr. 5, 2012

(30) Foreign Application Priority Data

Mar. 31, 2009 (GB) .................................. 0905511.2

(51) Int. Cl.
*G01N 33/569* (2006.01)
*G01N 33/535* (2006.01)
(52) U.S. Cl.
USPC ......................... 435/7.22; 435/7.92; 435/7.95
(58) Field of Classification Search
None
See application file for complete search history.

(56) References Cited

PUBLICATIONS

Lederman et al (Molecular Immunology 28:1171-1181, 1991).*
Li et al (Proc. Natl. Acad. Sci. USA 77:3211-3214, 1980).*
Dowdall, Samantha M.J. et al., "Characterisation of IgG(T) serum antibody responses to two larval antigen complexes in horses naturally- or experimentally-infected with cyathostomins," International Journal for Parasitology, vol. 34, No. 1, Jan. 2004 (pp. 101-108).
Dowdall, S.M.J. et al., "Antigen-specific IgG(T) responses in natural and experimental cyathostominae infection in horses," Veterinary Parasitology, vol. 106, No. 3, Jun. 26, 2002, pp. 225-242.
Dowdall, S.M.J. et al., "Purification and analyses of the specificity of two putative diagnostic antigens for larval cyathostomin infection in horses," Research in Veterinary Science, vol. 75, No. 3, Dec. 2003 (pp. 223-229).
Matthews, Jacqueline B. et al., "Recent developments in research into the *Cyathostominae* and *Anoplocephala perfoliata*," Veterinary Research (Les Ulis), vol. 35, No. 4, Jul. 2004 pp. 371-381.
McWilliam, Hamish E.G. et al., "Identification and characterization of an immunodiagnostic marker for cyathostomin developing stage larvae," International Journal for Parasitology, vol. 40, No. 3, Mar. 2010, pp. 265-275.

Abbott, J.B. et al., "Science: Overview—The problem of diagnosing tapeworm infections in horses," Equine Veterinary Journal (2008), vol. 40, No. 1, pp. 5-6.
Abbott, J.B. et al., "Serological changes observed in horses infected with *Anoplocephala perfoliata* after treatment with praziquantel and natural reinfection," The Veterinary Record, Jan. 12, 2008, pp. 51-53.
Barrett, E.J. et al., "Field trial of the efficacy of a combination of ivermectin and praziquantel in horses infected with roundworms and tapeworms," The Veterinary Record, Mar. 13, 2004, pp. 323-325.
Bendtsen, Jannick Dyrlev et al., "Improved Prediction of Signal peptides: SignalP 3.0," J. Mol. Biol., (2004), vol. 340, pp. 783-795.
Bucknell, D.G. et al., "The Prevalence and Epidemiology of Gastrointestinal Parasites of Horses in Victoria, Australia," International Journal for Parasitology, vol. 25, No. 6, 1995, pp. 711-724.
Chapman, M.R. et al., "Equine cyathostome populations: accuracy of species composition estimations," Veterinary Parasitology 116 (2003), pp. 15-21.
Clark, H.J. et al., "Isolation and characterisation of a beta tubulin isotype 2 gene from two species of cyathostomin," International Journal for Parasitology, vol. 35 (2005), pp. 349-358.
Eysker, M. et al., "The effect of ivermectin treatment against inhibited early third stage, late third stage and fourth stage larvae and adult stages of the cyathostomes in Shetland ponies and spontaneous expulsion of these helminthes," Vet. Parasitol., vol. 42, (1992) pp. 295-302.
Eysker, M. et al., "Mucosal larval recovery techniques of cyathostomes: can they be standardized?" Veterinary Parasitology, vol. 85 (1999), pp. 137-149.
Geldhof, P. et al., "Protein disulphide isomerase of *Osteragia ostertagi*: an excretory-secretory product of L4 and adult worms?" International Journal for Parasitology, vol. 33 (2003), pp. 129-136.
Giles, C.J. et al., "Larval cyathostomiasis (immature trichonema-induced enteropathy): A report of 15 clinical cases", Equine Veterinary Journal, vol. 17, No. 3 (1985), pp. 196-201.
Kaplan, Ray M., "Anthelmintic resistance in nematodes of horses," Vet. Res. 33 (2002), pp. 491-507.
Hodgkinson, J.E. et al., "Evaluation of the specificity of five oligoprobes for identification of cyathostomin species from horses," International Journal for Parasitology, vol. 31 (2001), pp. 197-204.
Kjaer, L.N. et al., "Interpretation of serum antibody response to *Anoplocephala perfoliata* in relation to parasite burden and faecal egg count," Equine Veterinary Journal, vol. 39, No. 6 (2007), pp. 529-533.
Klei, T.R. et al., "Evaluation of ivermectin at an elevated dose against encysted equine cyathostome larvae," Vet. Parasitol., vol. 47 (1993) pp. 99-106.
Larkin, M.A. et al., "Clustal W and Clustal X version 2.0," Bioinformatics, vol. 23, No. 21, (2007) pp. 2947-2948.
Love, S. et al., "The development of naturally acquired cyathostome infection in ponies," Vet. Parasitol., vol. 44, (1992) pp. 127-142.
Lyons, E.T. et al., "Historical perspective of cyathostomes: prevalence, treatment and control programs," Veterinary Parasitology, vol. 85 (1999), pp. 97-112.
Lyons, E.T. et al., "A study (1977-1992) of population dynamics of endoparasites featuring benzimidazole-resistant small strongyles (Population S) in Shetland ponies," Veterinary Parasitology, 1996; 66:75-86.

(Continued)

*Primary Examiner* — Padma V Baskar
(74) *Attorney, Agent, or Firm* — Barnes & Thornburg LLP

(57) ABSTRACT

The present invention provides a method of diagnosing a *cyathostomin* infection, said method comprising the step of identifying a level of anti-*cyathostomin* larval antigen antibodies in a sample, wherein a level of anti-*cyathostomin* larval antigen antibodies is indicative of a *cyathostomin* infection.

12 Claims, 11 Drawing Sheets

(56) References Cited

PUBLICATIONS

Figures 1, 2:
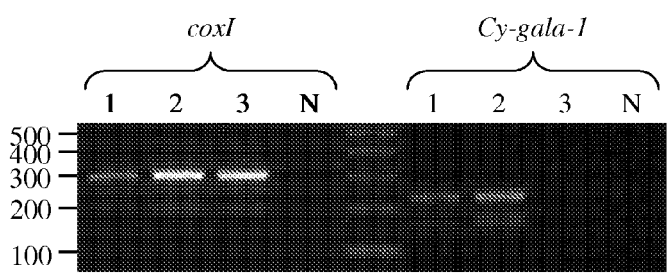

Marchier-Bauer, Aron et al., "CDD: a conserved domain database for interactive domain family analysis," Nucleic Acids Research, vol. 35, 2007, D237-D240.

Murphy, D. et al., "The pathogenic effects of experimental cyathostome infections in ponies," Veterinary Parasitology, vol. 70 (1997), pp. 99-110.

Proudman, Chris et al., "Control of intestinal parasites in horses," In Practice, Feb. 2000, pp. 90-97.

Proudman, C.J. et al., "Correlation of antigen specific IgG and IgG(T) responses with *Anoplocephala perfoliata* infection intensity in the horse," Parasite Immunology, vol. 18 (1996), pp. 499-506.

Proudman, C.J. et al., "Use of excretory/secretory antigens for the serodiagnosis of *Anoplocephala perfoliata* cestodosis," Vet Parasitol. 1996; 61(3-4):239-47.

Reid, S.W.J. et al., "Epidemiological risk factors associated with a diagnosis of clinical cyathostomiasis in the horse," Equine Veterinary Journal, vol. 27, No. 2 (1995) pp. 127-130.

Reinemeyer, C.R. et al., "The Prevalence and Intensity of Internal Parasites of Horses in the U.S.A.," Vet. Parasitol., vol. 15, (1984) pp. 75-83.

Shibui, Akiko et al., "Cloning and characterization of a novel gene encoding keratin-like protein from nematode *Nippostrongylus brasiliensis*," Biochimica et Biophysica Acta, 1522 (2001), pp. 59-61.

Martin, Samuel A.M. et al., "The construction of spliced leader cDNA libraries from the filarial nematode *Brugia pahangi*," Molecular and Biochemical Parasitology, vol. 70 (1995) pp. 241-245.

Altschul, S.F. et al., "Basic local alignment search tool," J. Mol. Biol. 1990:215(3): 403-10 (abstract only).

Klei, T.R. et al., "Irradiated larval vaccination of ponies against strongylus vulgaris," J. Parasitol, 1982:68(4): 561-9 (abstract only).

Lichtenfels, J.R. et al., "Illustrated identification keys to strongylid parasites (Strongylidae: Nematoda) of horses, zebras and asses (Equidae)," Vet Parasitol. 2008:156(1-2):4-161,Epub May 21, 2008 (abstract only).

Ogbourne, C.P., "The prevalence, relative abundance and site distribution of nematodes of the subfamily *Cyathostominae* in horses killed in Britain," J. Helmintol. 1976:50(3):203-14 (abstract only).

Love S et al., "Pathogenecity of cyathostome infection," *Veterinary Parasitology*, 1999; 85: 113-122.

International Search Report prepared for PCT/GB2010/000616, issued Sep. 7, 2010.

\* cited by examiner

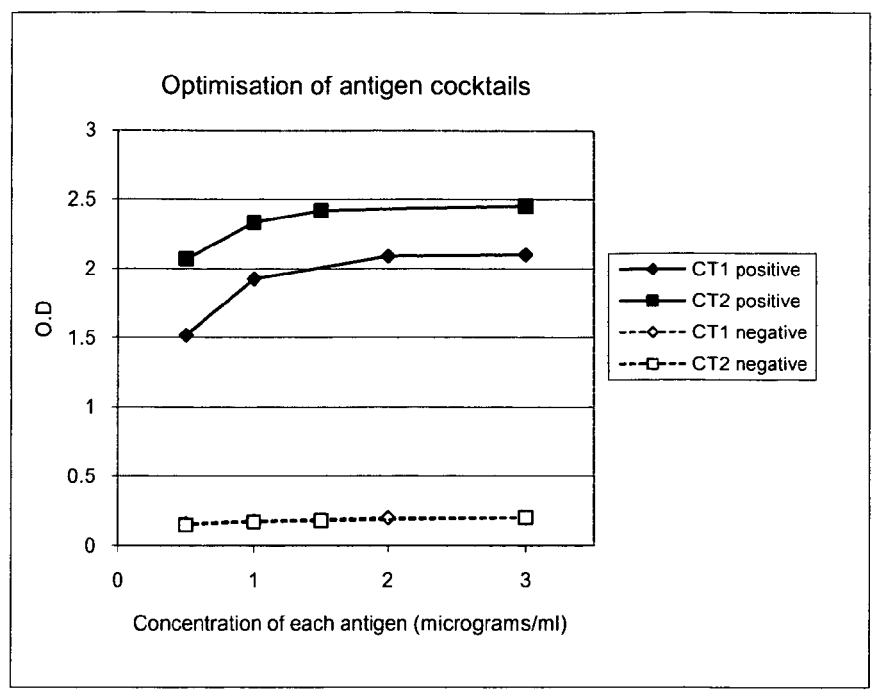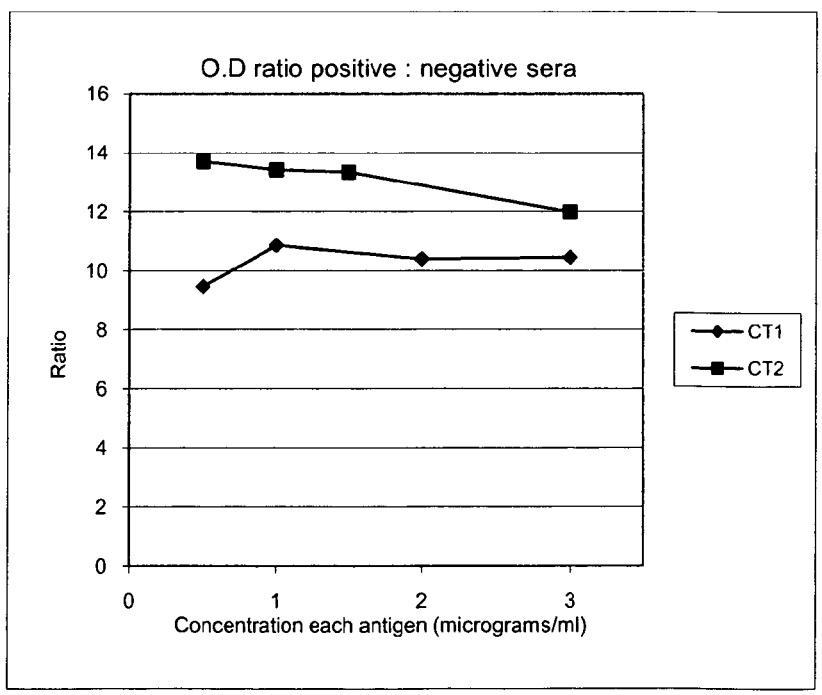
Figure 7 A & B

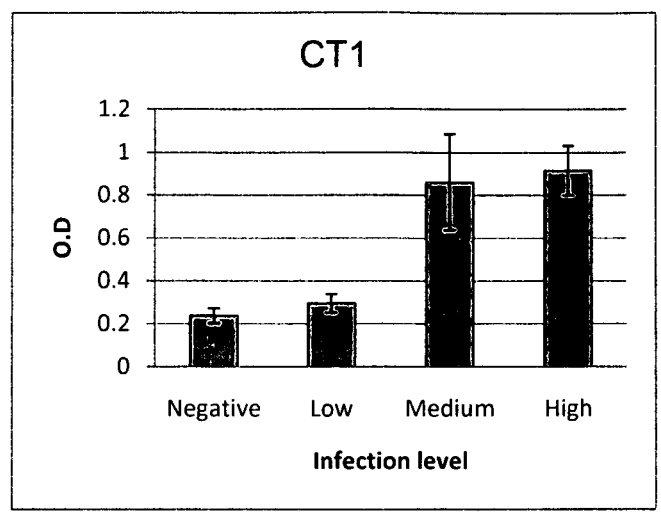
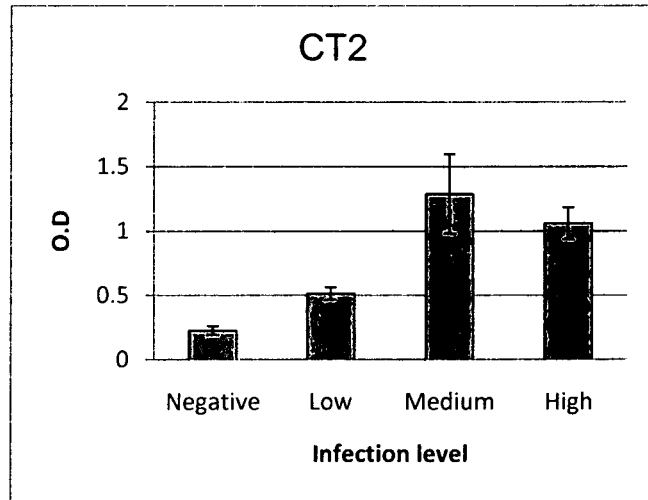
Figure 7 C and D

SEQUENCE LISTING

<160> NUMBER OF SEQ ID NOS: 83

<210> SEQ ID NO 1
<211> LENGTH: 223
<212> TYPE: PRT
<213> ORGANISM: cyathostomum pateratum

<400> SEQUENCE: 1

Met Asn Lys Thr Leu Thr Phe Leu Thr Val Val Ser Ala Val Ala Leu
1               5                   10                  15

Ala Gln Gly Val Met Asp Leu Phe Gly Glu Glu Gly Arg Glu His
            20                  25                  30

Arg Arg His His Arg His Ser Leu Leu Pro Pro Tyr Leu His Asn Val
        35                  40                  45

Ser Cys Glu Ala Lys Trp Glu Tyr Phe Lys Ile Val Gly Asn Arg Ser
50                  55                  60

Leu Thr Phe Ala Glu Lys Arg Lys Glu Ile Ser Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Ala Leu
                100                 105                 110

Pro Asn Ala Val Lys Lys Val Asn Asp Leu Leu Asp Asn Glu Asn Gln
            115                 120                 125

Thr Pro Arg Gln Leu Tyr Val Ala Leu Arg Lys Leu Gly Arg Gln Asn
        130                 135                 140

Pro Ala Leu Tyr Arg Ile Val Glu Tyr Ile Asn Val Ala Val Arg Leu

```
              145                 150                 155                 160
Arg Ser Glu Glu Val Asp Glu Gln Glu Gln Arg Arg Leu Ser Ala
                165                 170                 175

Leu Pro Phe Gly Asp His Asn Asp Asn Leu Glu Glu Gln Asp Phe Gly
            180                 185                 190

Glu Gln Asp Phe Arg Tyr Val Tyr Gly Phe Glu Cys Ala Arg Phe Leu
            195                 200                 205

Leu Gln Asn Gly Arg Met Phe Gly Leu Asn Thr Asp Glu Arg Tyr
            210                 215                 220

<210> SEQ ID NO 2
<211> LENGTH: 669
<212> TYPE: DNA
<213> ORGANISM: cyathostomum pateratum

<400> SEQUENCE: 2
atgaacaaaa cgttaacatt tctcacagtc gttagtgccg tagctctggc ccaaggtgtc      60
atggaccttt ttggtgaaga gggtcgtgaa gaacatcgtc gtcaccatcg tcattcactt     120
ttaccaccat atctccacaa tgtgagctgt gaggctaaat gggagtactt caaaattgtg     180
gggaacagga gtttgacctt tgctgagaaa agaaaggaaa ttagcgagtg ggcaaaaaaa     240
tacaatgttg tggatgaagt tgcaagctac aatgcttaca gggaaaaact caagcaggag     300
cacagaaaaa acgttagcga acttgtttct gctcttccaa acgcagtgaa gaaagtcaat     360
gatcttctag acaatgaaaa tcagactcct aggcaacttt acgttgccct tagaaaactt     420
ggtagacaaa atccggcact ttaccgtatt gtcgagtaca ttaatgtggc tgtaagacta     480
agaagtgaag aagtggatga gcaagaacaa cgaagaaggc tgtcagctct acctttggc      540 gaccataacg ataatttgga agagcaggac ttcggtgaac aagactttcg ctatgtctat     600
ggctttgagt gtgcaagatt tctccttcaa aatggaagaa tgtttggact aacacagat      660 gaaagatat                                                             669

<210> SEQ ID NO 3
<211> LENGTH: 192
<212> TYPE: PRT
<213> ORGANISM: Cylicocyclus nassatus

<400> SEQUENCE: 3

His Glu Glu Leu Arg Arg His His Arg His Ser Leu Leu Pro Pro Tyr
1               5                   10                  15

Leu His Asn Val Ser Cys Glu Ala Lys Trp Glu Tyr Phe Lys Ile Val
            20                  25                  30

Gly Asn Arg Ser Leu Thr Phe Ala Glu Lys Lys Gly Lys Ser Ser Glu
        35                  40                  45

Trp Ala Lys Lys Tyr Asn Val Val Asp Glu Val Ala Ser Tyr Asn Ala
    50                  55                  60

Tyr Arg Glu Lys Leu Lys Gln Glu His Arg Lys Asn Val Ser Glu Leu
65                  70                  75                  80

Val Ser Gly Leu Pro Gly Ala Val Lys Lys Val Asn Glu Leu Leu Asp
                85                  90                  95

Asn Glu Asn Gln Thr Pro Arg Gln Leu Tyr Val Ala Leu Arg Lys Leu
            100                 105                 110

Gly Lys Gln Asn Pro Val Leu Tyr Arg Val Val Glu Phe Val Asn Leu
        115                 120                 125

Val Val Arg Phe Arg Arg Glu Asp Ser Asp Glu Gln Glu Gln Arg Glu
    130                 135                 140
```

```
Met Leu Ser Thr Leu Pro Phe Ser Glu Asn Asn Glu Glu Gln Asp Leu
145                 150                 155                 160

Gly Glu Gln Asp Phe Gln Tyr Ile Tyr Gly Phe Glu Cys Ala Arg Phe
            165                 170                 175

Ile Phe Gln Asn Gly Arg Met Phe Gly Leu Asn Thr Asp Arg Arg Tyr
        180                 185                 190

<210> SEQ ID NO 4
<211> LENGTH: 576
<212> TYPE: DNA
<213> ORGANISM: Cylicocyclus nassatus

<400> SEQUENCE: 4
catgaagaac ttcgtcgtca ccatcgtcat tcacttttac caccctatct ccacaatgtg     60
agctgtgaag ccaaatggga atacttcaag attgtgggga acaggagctt gacttttgct    120
gaaaagaagg gaaaagtag cgagtgggca aaaaaataca atgttgtgga tgaagttgca     180
agttacaatg cctatagaga aaaacttaag caggagcaca ggaaaaacgt tagcgaactt    240
gtttctggtc ttcccggtgc tgtgaagaaa gtaaacgaac tcttggataa tgagaatcag    300
actcctaggc aactttacgt tgctctaaga aagcttggta acaaaatcc agtactctac     360 cgtgttgtcg agtttgtcaa tttggttgtg agatttagac gtgaagattc ggatgagcaa    420
gaacaacgag aaatgctgtc aactttacct ttcagcgaaa ataatgaaga gcaggacctt    480
ggtgaacaag acttccagta catctatggt tttgaatgtg caagattcat ctttcaaaat    540
gggagaatgt ttggactcaa cacggataga agatat                             576

<210> SEQ ID NO 5
<211> LENGTH: 175
<212> TYPE: PRT
<213> ORGANISM: Coronocyclus coronatus

<400> SEQUENCE: 5

Ser Cys Val Ala Lys Trp Glu Tyr Phe Lys Ile Val Ile Asn Arg Ser
1               5                   10                  15

Leu Thr Phe Ala Gln Arg Lys Glu Glu Ile Ser Lys Trp Ala Lys Lys
            20                  25                  30

Tyr Lys Val Glu Asp Glu Val Ala Ser Tyr Asn Ala Tyr Arg Glu Lys
        35                  40                  45

Leu Lys Gln Gln His Arg Lys Asn Val Ser Glu Leu Val Ser Asn Leu
    50                  55                  60

Pro Gly Ala Val Glu Arg Val Asn Lys Leu Leu Asp Asn Glu Asn Gln
65                  70                  75                  80

Thr Pro Lys Gln Leu Tyr Leu Ala Leu Arg Glu Leu Gly Lys Gln Asn
                85                  90                  95

Pro Ala Leu Tyr His Val Val Tyr Val Asn Val Val Arg Leu
            100                 105                 110

Lys Arg Glu Glu Leu Asp Gln Gln Asp Gln Arg Arg Ala Leu Ser Gly
        115                 120                 125

Ser Leu Phe Gly Glu Asn Asn Asp Asn Leu Glu Glu Gln Asp Phe Gly
    130                 135                 140

Glu Glu Asp Phe Arg Tyr Val Tyr Gly Phe Glu Cys Ala Arg Phe Ile
145                 150                 155                 160

Leu Gln Asn Gly Arg Met Phe Gly Leu Asn Met Asp Arg Asn Tyr
                165                 170                 175
```

<210> SEQ ID NO 6
<211> LENGTH: 525
<212> TYPE: DNA
<213> ORGANISM: Coronocyclus coronatus

<400> SEQUENCE: 6

```
agctgtgtgg ctaagtggga gtacttcaag atcgtgatga acaggagtct gacgtttgct    60
caaagaaagg aagaaattag caagtgggcg aaaaaataca agttgagga tgaagttgca    120
agctacaatg cttatagaga aaaactcaag cagcagcaca ggaaaaacgt tagcgaactt   180
gtttctagtc ttcccggtgc aatggaaaga gtgaacaaac ttttggacaa tgaaaaccag   240
accccctaagc aactttacct tgccctacga gaacttggca acaaaatcc ggcactttac    300
catgttgtcg agtatgtcaa tgtggttgtg agacttaaac gagaagaatt ggatgaacaa   360
gatcaatgaa gagcgctgtc gggttcactt tttggcgaga ataacgacaa tctagaagag   420
caggactttg gtgaagaaga ctttcgctat gtctatgggt ttgaatgtgc aagattcatc   480
cttcaaaatg gaagaatgtt tggtctaaac atggatagga attat              525
```

<210> SEQ ID NO 7
<211> LENGTH: 199
<212> TYPE: PRT
<213> ORGANISM: Cyathostomum catinatum

<400> SEQUENCE: 7

Gly Glu Glu Asp Arg Glu Glu His Arg Arg His His Arg His Ser Leu
1               5                   10                  15
Leu Pro Pro Tyr Leu His Asn Val Ser Cys Val Ala Lys Trp Glu Tyr
            20                  25                  30
Phe Arg Ile Val Gly Asn Arg Ser Leu Thr Phe Ala Glu Lys Lys Lys
        35                  40                  45
Glu Ile Ser Glu Trp Ala Lys Lys Tyr Asn Val Leu Asp Glu Val Ala
    50                  55                  60
Ser Tyr Asn Ala Tyr Arg Glu Lys Leu Lys Gln Glu His Arg Lys Asn
65                  70                  75                  80
Val Ser Glu Leu Val Ser Asp Leu Pro Lys Ala Val Lys Lys Val Asn
                85                  90                  95
Asp Leu Leu Asp Asn Glu Asn Gln Thr Pro Arg Gln Leu Tyr Val Ala
            100                 105                 110
Leu Arg Glu Leu Gly Arg Gln Asn Pro Thr Leu Tyr Arg Ile Val Glu
        115                 120                 125
Tyr Ile Asn Val Ala Val Arg Arg Ser Glu Glu Leu Asp Glu Gln
    130                 135                 140
Glu Gln Gly Arg Arg Leu Ser Ala Leu Pro Phe Gly Asp Asn Asn Asp
145                 150                 155                 160
Asn Leu Glu Glu Gln Asp Phe Gly Glu Gln Asp Phe Arg Tyr Val Tyr
                165                 170                 175
Gly Phe Glu Cys Ala Arg Phe Leu Leu Gln Asn Gly Arg Met Phe Gly
            180                 185                 190
Leu Asn Thr Asp Glu Arg Asp
        195

<210> SEQ ID NO 8
<211> LENGTH: 591
<212> TYPE: DNA
<213> ORGANISM: Cyathostomum catinatum

<400> SEQUENCE: 8

```
gaggatcgtg aagaacatcg ccgtcaccat cgtcattcac tcttgccacc atatctccac    60
aacgtgagct gtgtggccaa atgggaatac tttagaattg tggggaacag gagtttaacg   120
tttgctgaga aaagaaaga aattagcgag tgggcaaaaa atacaatgt tctggatgaa    180 gtagcaagct acaatgctta tagggaaaaa ctcaagcagg agcacagaaa aaacgttagc   240
gaacttgttt ctgatcttcc caaggcagta agaaagtca acgatcttct agacaatgaa   300
aatcagactc ctaggcaact ttatgttgcc cttagagagc ttggtagaca aaatccgaca   360
ctttaccgta ttgtcgagta catcaatgtg gctgtaaggc gaagaagtga agaactggat   420
gagcaagaac aaggaagaag gctgtcagct ttaccttcg gcgacaacaa cgataatttg   480
gaagagcagg acttcggtga acaagacttt cgctatgtct acggctttga gtgtgcaaga   540
tttctccttc aaaatggaag aatgttcgga ctcaacacag atgaaagaga t          591
```

```
<210> SEQ ID NO 9
<211> LENGTH: 841
<212> TYPE: DNA
<213> ORGANISM: Cylicocyclus ashworthi

<400> SEQUENCE: 9
atgaacaaaa cgttaacatt tctcacagtc gttagtgccg tagttctggc ccaaggtgtc    60 atggacctttt ttggtgaaga gggtcgtgaa gaacatcgcc gtcaccatcg tcattcactc   120
ttaccaccat atctccacaa cgtgagctgt gtggctaaat gggagtactt caaaattgta   180
gggaacagga gtttaacgtt tgctgagaaa aagaagaaa ttagccagtg ggcaaaaaaa   240
tacaatgttg tggtaagctt ttctgaatta atgtaaatac actcgcatgc tggccttttt   300
aggatgaagt tgcaagctac aatgcttaca gggagaaact caagcaggag cacagaaaaa   360
acgttagcga acttgtttct gctcttccaa acgcagtaaa gaaagtcaac aatcttctag   420
acaatgaaaa tcagactctt aggcaacttt acgttgccct tagagaactt ggtagacaaa   480
atccggcagt aagtagaaag agctgcactc ctgggcttaa taaaacaaat tatttaagct   540
ttaccgtatt gtcgagtaca tcaatgtggc tgtaagacga agaagtgaag gactggatga   600
gcaagaacaa cgaagaaagc tatcagcttt accttcggc gacaacaacg ataatatgga   660
agagcaggac ttcggtgaac aagactttcg ctatgtctac ggctttgagt gtgcaagatt   720
tctccttcaa aatggaagaa tgtttgggct caacacagat gaaagagatt agcaaagaat   780
caattgtagt tcaaagcggt agagtttgag ctgcaaactc agcatgccat catcacctcc   840
t                                                                   841
```

```
<210> SEQ ID NO 10
<211> LENGTH: 223
<212> TYPE: PRT
<213> ORGANISM: Cylicocyclus ashworthi

<400> SEQUENCE: 10

Met Asn Lys Thr Leu Thr Phe Leu Thr Val Val Ser Ala Val Val Leu
1               5                   10                  15

Ala Gln Gly Val Met Asp Leu Phe Gly Glu Glu Gly Arg Glu His
            20                  25                  30

Arg Arg His His Arg His Ser Leu Leu Pro Pro Tyr Leu His Asn Val
        35                  40                  45

Ser Cys Val Ala Lys Trp Glu Tyr Phe Lys Ile Val Gly Asn Arg Ser
    50                  55                  60

Leu Thr Phe Ala Glu Lys Lys Glu Glu Ile Ser Gln Trp Ala Lys Lys
65                  70                  75                  80
```

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Ala Leu
            100                 105                 110

Pro Asn Ala Val Lys Lys Val Asn Leu Leu Asp Asn Glu Asn Gln
        115                 120                 125

Thr Leu Arg Gln Leu Tyr Val Ala Leu Arg Glu Leu Gly Arg Gln Asn
    130                 135                 140

Pro Ala Leu Tyr Arg Ile Val Glu Tyr Ile Asn Val Ala Val Arg Arg
145                 150                 155                 160

Arg Ser Glu Gly Leu Asp Glu Gln Gln Arg Arg Lys Leu Ser Ala
                165                 170                 175

Leu Pro Phe Gly Asp Asn Asn Asp Asn Met Glu Glu Gln Asp Phe Gly
            180                 185                 190

Glu Gln Asp Phe Arg Tyr Val Tyr Gly Phe Glu Cys Ala Arg Phe Leu
        195                 200                 205

Leu Gln Asn Gly Arg Met Phe Gly Leu Asn Thr Asp Glu Arg Asp
    210                 215                 220

<210> SEQ ID NO 11
<211> LENGTH: 841
<212> TYPE: DNA
<213> ORGANISM: Cyathostomum catinatum

<400> SEQUENCE: 11

```
atgaacaaaa cg

```
Arg Arg His Arg Arg His Ser Leu Leu Pro Pro Tyr Leu His Asn Val
            35                  40                  45

Ser Cys Val Ala Lys Trp Glu Tyr Phe Arg Ile Val Gly Asn Arg Ser
 50                  55                  60

Leu Thr Phe Ala Glu Lys Glu Glu Ile Ser Glu Trp Ala Lys Lys
 65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Ala Leu
               100                 105                 110

Pro Asn Ala Val Lys Lys Val Asn Asp Leu Leu Asp Asn Glu Asn Gln
               115                 120                 125

Thr Pro Arg Gln Leu Tyr Val Ala Leu Arg Glu Leu Gly Arg Gln Asn
130                 135                 140

Pro Ala Leu Tyr Arg Ile Val Glu Tyr Ile Asn Val Ala Val Arg Leu
145                 150                 155                 160

Arg Ser Glu Glu Val Asp Glu Gln Gln Arg Arg Leu Ser Ala
               165                 170                 175

Leu Pro Phe Gly Asp His Asn Asp Asn Met Glu Glu Gln Asp Phe Gly
               180                 185                 190

Asp Gln Asp Phe Arg Tyr Val Tyr Gly Phe Glu Cys Ala Arg Phe Leu
               195                 200                 205

Leu Gln Asn Gly Arg Met Phe Gly Leu Asn Thr Asp Glu Arg Tyr
               210                 215                 220

<210> SEQ ID NO 13
<211> LENGTH: 769
<212> TYPE: DNA
<213> ORGANISM: Cylicostephanus goldi

<400> SEQUENCE: 13
atgaacaaaa cgttaacatt tctcacagtc gttagtgccg tagtcctggc tcaaggtgtc      60
gtggaccttt ttggtgaaga gggtcgtgaa gaacatcgcc gtcaccatcg tcattcactc     120
ttaccaccat atctccacaa cgtcagctgt gtggctaaat gggaatactt caaaattgtg     180
gggaatagga gtttgacatt tgctgagaaa aagaagaaa ttagcgagtg gctaaaaaaa     240
tacaatgtag tggtaagctt ttttgacttg atgtaaatgc actcgtatgc cggccctttt     300
aggatgaagt tgcaaggtac aatgcttata gagaaaaact taagcaggaa cacaggaaaa     360
acgtcagcga acttgtttct gatcttccca acgcagtaaa gaaagtgaat gatctcctgg     420
acaatgagaa tcaaactcct aggcaacttt acattgccct cagagaactt ggtagacaaa     480
atccagaagt aagttgaaag tgctgcaatt ttaggcttag ataaaacagt tgtttaagct     540
ttaccgtgtt gtcgagttta tcaatgtggc tgtaagaata agacgtgaag atttggatga     600
gcaagaacaa cgaacaaggc tgtcaacttt acctttggc gacaacaacg acaatttcga     660
agagcaagac ttcggtgaac aagactttcg ctatgtctat ggctttgagt gtgcaagatt     720
tctccttcaa aatggaagaa tgtttggact aaacacggat agaagatac                 769

<210> SEQ ID NO 14
<211> LENGTH: 223
<212> TYPE: PRT
<213> ORGANISM: Cylicostephanus goldi

<400> SEQUENCE: 14

Met As

Ala Gln Gly Val Val Asp Leu Phe Gly Glu Glu Gly Arg Glu His
            20                  25                  30

Arg Arg His His Arg His Ser Leu Leu Pro Pro Tyr Leu His Asn Val
            35                  40                  45

Ser Cys Val Ala Lys Trp Glu Tyr Phe Lys Ile Val Gly Asn Arg Ser
 50                  55                  60

Leu Thr Phe Ala Glu Lys Lys Lys Glu Ile Ser Glu Trp Ala Lys Lys
 65                  70                  75                  80

Tyr Asn Val Val Asp Glu Val Ala Arg Tyr Asn Ala Tyr Arg Glu Lys
                    85                  90                  95

Leu Lys Gln Glu His Arg Lys Asn Val Ser Glu Leu Val Ser Asp Leu
                100                 105                 110

Pro Asn Ala Val Lys Lys Val Asn Asp Leu Leu Asp Asn Glu Asn Gln
                115                 120                 125

Thr Pro Arg Gln Leu Tyr Ile Ala Leu Arg Glu Leu Gly Arg Gln Asn
        130                 135                 140

Pro Glu Leu Tyr Arg Val Val Glu Phe Ile Asn Val Ala Val Arg Ile
145                 150                 155                 160

Arg Arg Glu Asp Leu Asp Glu Gln Glu Gln Arg Thr Arg Leu Ser Thr
                    165                 170                 175

Leu Pro Phe Gly Asp Asn Asn Asp Asn Phe Glu Glu Gln Asp Phe Gly
                180                 185                 190

Glu Gln Asp Phe Arg Tyr Val Tyr Gly Phe Glu Cys Ala Arg Phe Leu
            195                 200                 205

Leu Gln Asn Gly Arg Met Phe Gly Leu Asn Thr Asp Arg Arg Tyr
    210                 215                 220

<210> SEQ ID NO 15
<211> LENGTH: 847
<212> TYPE: DNA
<213> ORGANISM: Cylicostephanus goldi

<400> SEQUENCE: 15
atgaacaaaa cgttaacatt tctcacagtc gttagtgccg tagtcctggc ccaaggtgtc      60
atggaccttc ttgatgaaga ggctcgtgga gagcatcgcc gtcaccatcg tcattcactc     120
ttaccaccat atctccacaa cgtgagctgt gtggctaaat gggaatactt caaaattgtg     180
gggaacagga gtttgacgtt tgctgagaaa aagaaagaaa ttagcgagtg gcaaaaaaaa     240
tacaacgttg tggtaagctt ttgtgactcg atgtagatac cccagatatt ctagataccc     300
atgctggcct ttttaggatg aagttgcaag ctacaatgct tatagagaaa aactcaagca     360
ggaacacagg aaaaacgtta gcgaacttgt atctgatctt cccaatgcag tgaagaaagt     420
gaatgatctc ctggacaatg agaatcaaac tcctaggcaa ctttacgttg ccctcagaga     480
acttggtaga caaaatccag cagtaagttg aaagtgctgc aatttcaggc ttagataaaa     540
cagttgttta agctttaccg tgttgtcgag ctcatcaatg tggctgtaag attaagacgt     600
gaagatttgg atgagcaaga acaacgaaca aggctgtcaa ccttaccttt ggcgacaac      660 aacaacaatt tcgatgagca ggacttcggt gaacaagact tcgctatgt ctatggcttt      720 gagtgtgcaa gatttctcct tcaaaatgga agaatgtttg gacttaacac ggatagaaga     780
tactagtaag agtcaactgt agctcaaagt ggttcgagc acgaacagca tgccatcatc      840
acctcct                                                                847

<210> SEQ ID NO 16

```
<211> LENGTH: 223
<212> TYPE: PRT
<213> ORGANISM: Cylicostephanus goldi

<400> SEQUENCE: 16
```

| | | | | | | | | | | | | | | | |
|---|---|---|---|---|---|---|---|---|---|---|---|---|---|---|---|
| Met | Asn | Lys | Thr | Leu | Thr | Phe | Leu | Thr | Val | Val | Ser | Ala | Val | Val | Leu |
| 1 | | | | 5 | | | | | 10 | | | | | 15 | |
| Ala | Gln | Gly | Val | Met | Asp | Leu | Leu | Asp | Glu | Glu | Ala | Arg | Gly | Glu | His |
| | | | 20 | | | | | 25 | | | | | 30 | | |
| Arg | Arg | His | His | Arg | His | Ser | Leu | Leu | Pro | Pro | Tyr | Leu | His | Asn | Val |
| | | | 35 | | | | 40 | | | | | 45 | | | |
| Ser | Cys | Val | Ala | Lys | Trp | Glu | Tyr | Phe | Lys | Ile | Val | Gly | Asn | Arg | Ser |
| | 50 | | | | | 55 | | | | | 60 | | | | |
| Leu | Thr | Phe | Ala | Glu | Lys | Lys | Lys | Glu | Ile | Ser | Glu | Trp | Ala | Lys | Lys |
| 65 | | | | | 70 | | | | | 75 | | | | | 80 |
| Tyr | Asn | Val | Val | Asp | Glu | Val | Ala | Ser | Tyr | Asn | Ala | Tyr | Arg | Glu | Lys |
| | | | | 85 | | | | | 90 | | | | | 95 | |
| Leu | Lys | Gln | Glu | His | Arg | Lys | Asn | Val | Ser | Glu | Leu | Val | Ser | Asp | Leu |
| | | | | 100 | | | | | 105 | | | | | 110 | |
| Pro | Asn | Ala | Val | Lys | Lys | Val | Asn | Asp | Leu | Leu | Asp | Asn | Glu | Asn | Gln |
| | | | 115 | | | | | 120 | | | | | 125 | | |
| Thr | Pro | Arg | Gln | Leu | Tyr | Val | Ala | Leu | Arg | Glu | Leu | Gly | Arg | Gln | Asn |
| | 130 | | | | | 135 | | | | | 140 | | | | |
| Pro | Ala | Leu | Tyr | Arg | Val | Val | Glu | Leu | Ile | Asn | Val | Ala | Val | Arg | Leu |
| 145 | | | | | 150 | | | | | 155 | | | | | 160 |
| Arg | Arg | Glu | Asp | Leu | Asp | Glu | Gln | Glu | Gln | Arg | Thr | Arg | Leu | Ser | Thr |
| | | | | 165 | | | | | 170 | | | | | 175 | |
| Leu | Pro | Phe | Gly | Asp | Asn | Asn | Asn | Asn | Phe | Asp | Glu | Gln | Asp | Phe | Gly |
| | | | 180 | | | | | 185 | | | | | 190 | | |
| Glu | Gln | Asp | Phe | Arg | Tyr | Val | Tyr | Gly | Phe | Glu | Cys | Ala | Arg | Phe | Leu |
| | | | | 195 | | | | | 200 | | | | | 205 | |
| Leu | Gln | Asn | Gly | Arg | Met | Phe | Gly | Leu | Asn | Thr | Asp | Arg | Arg | Tyr | |
| | | | 210 | | | | | 215 | | | | | 220 | | |

```
<210> SEQ ID NO 17
<211> LENGTH: 835
<212> TYPE: DNA
<213> ORGANISM: Cylicostephanus goldi

<400> SEQUENCE: 17
atgaacaaaa cgttaacatt tctcacagtc gttagtgccg ttgtcctggc gcaaggtgtc    60
atggccctat ttggtgaaga gagtcgtgaa gaacaccgcc gtcaccatcg tcattcactc   120
ttaccaccat atctccacaa cgtgagctgt gtggctaaat gggagtactt caaaattgtg   180
gggaacagga gtttgacgtt tgctgagaaa aagaaagaaa tcagcgagtg gctaaaaaaa   240
tacaatgttg tggataagctt ttttgacttg atgtaaatgc actcgcatgc cggccttttat   300
aggatgaagt tgcaagctac aatgcttata gagaaaaact caagcaggaa cacaggaaaa   360
acgttagcga acttgttttct gatcttccca acgcagtaaa gaaagtcagc gatcttttgg   420
acaacgaaaa tcagacttct aggcaacttt atgttgcact cagagaactt ggtagacaaa   480
atccggcagt aagttgaaga ggctccaatt ttgggctcaa gcaaaaataa ttattttagc   540
tataccgtgt cgtcgagtat atcaatgtgg ctgtgagatt aagacgaaaa gaacaggatg   600
aacaagaacg acaaggaacg ctgtcagctc tacctttttgg cgagaataac gacaatttgg   660
aagagcagga ctttggtgaa caagactttc gctatgtcta tggctttgag tgtgcaagat   720
```

```
ttctccttca aaatggaaga atgtttggac tcaacacgga tagaagatac cagtaagagt    780
caactgtagc tcaaagtggg tttgagctac gaacagcatg ccatcatcac ctcct         835
```

<210> SEQ ID NO 18
<211> LENGTH: 223
<212> TYPE: PRT
<213> ORGANISM: Cylicostephanus goldi

<400> SEQUENCE: 18

```
Met Asn Lys Thr Leu Thr Phe Leu Thr Val Val Ser Ala Val Val Leu
1               5                   10                  15

Ala Gln Gly Val Met Ala Leu Phe Gly Glu Glu Ser Arg Glu His
            20                  25                  30

Arg Arg His His Arg His Ser Leu Leu Pro Pro Tyr Leu His Asn Val
        35                  40                  45

Ser Cys Val Ala Lys Trp Glu Tyr Phe Lys Ile Val Gly Asn Arg Ser
    50                  55                  60

Leu Thr Phe Ala Glu Lys Lys Glu Ile Ser Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Asp Leu
            100                 105                 110

Pro Asn Ala Val Lys Lys Val Ser Asp Leu Leu Asp Asn Glu Asn Gln
        115                 120                 125

Thr Ser Arg Gln Leu Tyr Val Ala Leu Arg Glu Leu Gly Arg Gln Asn
    130                 135                 140

Pro Ala Val Tyr Arg Val Val Glu Tyr Ile Asn Val Ala Val Arg Leu
145                 150                 155                 160

Arg Arg Lys Glu Gln Asp Glu Gln Arg Gln Gly Thr Leu Ser Ala
                165                 170                 175

Leu Pro Phe Gly Glu Asn Asn Asp Asn Leu Glu Glu Gln Asp Phe Gly
            180                 185                 190

Glu Gln Asp Phe Arg Tyr Val Tyr Gly Phe Glu Cys Ala Arg Phe Leu
        195                 200                 205

Leu Gln Asn Gly Arg Met Phe Gly Leu Asn Thr Asp Arg Arg Tyr
    210                 215                 220
```

<210> SEQ ID NO 19
<211> LENGTH: 830
<212> TYPE: DNA
<213> ORGANISM: Cylicostephanus longibursatus

<400> SEQUENCE: 19

```
atgaacaaaa cgttaacatt tctcaccgtc gtctatgccg tagtcctggc ccaaggtgtc    60
atggaccttt tggtgaaga gggtcgtgaa gaacatcgcc gtcaccatcg tcattcactc   120
ttaccaccat atctccacaa tgtgagctgt gtggctaaat gggaatactt caaaattgtg   180
gggaacagga gtttgacgtt tgctgagaaa aaggaagaaa ttagcaagtg ggcaaaaaaa   240
tacaatgttg tggtacgctt ttgtaacccc gtataatata ctctcgcata ctggccgttt   300
caggatgaag ttgcaagcta cagtgcttgc agggaaaagc ttaagcagga acacaggaaa   360
aacgttagcg aaattgtttc taatcttccc aatgcagtga agaaagtaaa cgatcttttg   420
gacaatgaaa atcagacccc caggcaactt tacgttgcct tcagaaaact tggtaaacaa   480
aatccggcag taagttgaaa gagctgcaat tttgggtttg aggagaaaaa actatttag    540
```

```
cttatcgtg ttgtcgagta tatcaatgtg cttgtgagac taagacgtga agaatttgat    600
gaagatcagc gaagatcgct gtcagcttta ccttttggcg acaataacga cgatttggaa    660
gagcaggact ttggtgaaca ggactttcgc tatatctatg gctttgagtg tgcaagattt    720
atccttcaaa atggaagaat gttcggactc aacacggata aagatatta gtaagagtca    780 actgtagctc gagggtttga gctacgaact gcatgccatc atcacctcct              830
```

<210> SEQ ID NO 20
<211> LENGTH: 222
<212> TYPE: PRT
<213> ORGANISM: Cylicostephanus longibursatus

<400> SEQUENCE: 20

```
Met Asn Lys Thr Leu Thr Phe Leu Thr Val Val Tyr Ala Val Val Leu
1               5                   10                  15

Ala Gln Gly Val Met Asp Leu Phe Gly Glu Glu Gly Arg Glu Glu His
            20                  25                  30

Arg Arg His His Arg His Ser Leu Leu Pro Pro Tyr Leu His Asn Val
        35                  40                  45

Ser Cys Val Ala Lys Trp Glu Tyr Phe Lys Ile Val Gly Asn Arg Ser
    50                  55                  60

Leu Thr Phe Ala Glu Lys Lys Glu Glu Ile Ser Lys Trp Ala Lys Lys
65                  70                  75                  80

Tyr Asn Val Val Asp Glu Val Ala Ser Tyr Ser Ala Cys Arg Glu Lys
                85                  90                  95

Leu Lys Gln Glu His Arg Lys Asn Val Ser Glu Ile Val Ser Asn Leu
            100                 105                 110

Pro Asn Ala Val Lys Lys Val Asn Asp Leu Leu Asp Asn Glu Asn Gln
        115                 120                 125

Thr Pro Arg Gln Leu Tyr Val Ala Phe Arg Lys Leu Gly Lys Gln Asn
    130                 135                 140

Pro Ala Leu Tyr Arg Val Val Glu Tyr Ile Asn Val Leu Val Arg Leu
145                 150                 155                 160

Arg Arg Glu Glu Phe Asp Glu Asp Gln Arg Arg Ser Leu Ser Ala Leu
                165                 170                 175

Pro Phe Gly Asp Asn Asn Asp Asp Leu Glu Glu Gln Asp Phe Gly Glu
            180                 185                 190

Gln Asp Phe Arg Tyr Ile Tyr Gly Phe Glu Cys Ala Arg Phe Ile Leu
        195                 200                 205

Gln Asn Gly Arg Met Phe Gly Leu Asn Thr Asp Arg Arg Tyr
    210                 215                 220
```

<210> SEQ ID NO 21
<211> LENGTH: 829
<212> TYPE: DNA
<213> ORGANISM: Cylicocyclus insigne

<400> SEQUENCE: 21

```
atgaacaaaa cgttaacatt tctcaccgtc gtctgtgccg tagtcctggc ccaaggtgtc    60
atggaccttt ttggtgaaga aggtcgtgaa gaacatcgcc gtcaccatcg tcattcactc    120
ttaccaccat atctccacaa tgtgagctgt gtggctaaat gggaatactt caaaattctg    180
gggaacagaa gtttgacgtt tgctgagaaa aaggaaaaaa tcagcgagtg gcaaaaaaag    240
tacaatgttg tggtacgctt ttgtaactcc gtataatata ccctcgcatg ctggccgttt    300
caggatgaag ttgcaagcta caatgcttgc agggaaaagc ttaagcagga acacaggaaa    360
```

```
aacgttagcg aaattgtttc taatcttccc aatgcagtaa agaaagtaaa cgatctttttg    420 gacaatgaaa atcagactcc caggcaactt tacgttgccc tcagaaaact cggtaaacaa    480
aatccgccag taagttgaaa gactgcaact ttgggtttaa gggaaaaaaa ctattttagc    540
tttaccgcgt tgtcgagtat atcaatgtgg ttgtgagact aagacgtgaa gaatctgatg    600
aagaacaacg aagaacgctg tcagctttac cttttggcga caataacgac aacttggaag    660
agcaagactt tggtgaagaa gactttcgct atatttatgg ctttgagtgt gcaagattta    720
tccttcaaaa tgggagaatg ttcggactca acacggatag aagatatcag taagagtcaa    780
ctgtagctta aaagtttgag ctacgaacag catgccatca tcacctcct                 829
```

<210> SEQ ID NO 22
<211> LENGTH: 222
<212> TYPE: PRT
<213> ORGANISM: Cylicocyclus insigne

<400> SEQUENCE: 22

```
Met Asn Lys Thr Leu Thr Phe Leu Thr Val Val Cys Ala Val Val Leu
1               5                   10                  15

Ala Gln Gly Val Met Asp Leu Phe Gly Glu Glu Gly Arg Glu His
            20                  25                  30

Arg Arg His His Arg His Ser Leu Leu Pro Pro Tyr Leu His Asn Val
        35                  40                  45

Ser Cys Val Ala Lys Trp Glu Tyr Phe Lys Ile Leu Gly Asn Arg Ser
    50                  55                  60

Leu Thr Phe Ala Glu Lys Lys Glu Lys Ile Ser Glu Trp Ala Lys Lys
65                  70                  75                  80

Tyr Asn Val Val Asp Glu Val Ala Ser Tyr Asn Ala Cys Arg Glu Lys
                85                  90                  95

Leu Lys Gln Glu His Arg Lys Asn Val Ser Glu Ile Val Ser Asn Leu
            100                 105                 110

Pro Asn Ala Val Lys Lys Val Asn Asp Leu Leu Asp Asn Glu Asn Gln
        115                 120                 125

Thr Pro Arg Gln Leu Tyr Val Ala Leu Arg Lys Leu Gly Lys Gln Asn
    130                 135                 140

Pro Pro Leu Tyr Arg Val Val Glu Tyr Ile Asn Val Val Val Arg Leu
145                 150                 155                 160

Arg Arg Glu Glu Ser Asp Glu Glu Gln Arg Arg Thr Leu Ser Ala Leu
                165                 170                 175

Pro Phe Gly Asp Asn Asn Asp Asn Leu Glu Glu Gln Asp Phe Gly Glu
            180                 185                 190

Glu Asp Phe Arg Tyr Ile Tyr Gly Phe Glu Cys Ala Arg Phe Ile Leu
        195                 200                 205

Gln Asn Gly Arg Met Phe Gly Leu Asn Thr Asp Arg Arg Tyr
    210                 215                 220
```

<210> SEQ ID NO 23
<211> LENGTH: 830
<212> TYPE: DNA
<213> ORGANISM: Cylicostephanus longibursatus

<400> SEQUENCE: 23

```
atgaacaaaa cgttaacatt tctcaccgtc gtctatgccg tagtcctggc ccaaggtgtc    60
atggaccttt ttggtgaaga gggtcttgaa gaacatcgcc gtcaccatcg tcattcactc    120
ttaccaccat atctccacaa tgtgagctgt gtggctaaat gggaatactt caaaattctg    180
```

| | |
|---|---:|
| gggaacagga gtttgacgtt tgctgagaaa aaggaaaaaa tcagcgagtg ggcaaaaaag | 240 |
| tacaatgttg tggtacgctt ttgtaactca gtataatata tcctcgcata ctggccgttt | 300 |
| caggatgaag ttgcaagcta caatgcttgc agggaaaagc ttaagcagga acacaggaaa | 360 |
| aacgttagcg aaattgtttc taatcttccc aatgcagtga agaaagtaaa cgatcttttg | 420 |
| gacaatgaaa atcagacccc caggcaactt tacgttgccc tcagaaaact tggtaaacaa | 480 |
| aatccggcag taagttgaaa gagctgcaat tttgggtttg aggaaaaaaa actattttag | 540 |
| ctttatcgtg ttgtcgagta tatcaatgtg cttgtgagac taagacgtga agaatttgat | 600 |
| gaagatcagc gaagatcgct gtcagcttta ccttttggcg acaataacga cgatttggaa | 660 |
| gagcaggact ttggtgaaca ggactttcgc tatatctatg gctttgagtg tgcaagattt | 720 |
| atccttcaaa atggaagaat gttcggactc aacacggata gaagatatta gtaagagtca | 780 |
| actgtagctc aagggtttga gctacgaact gcatgccatc atcacctcct | 830 |

<210> SEQ ID NO 24
<211> LENGTH: 222
<212> TYPE: PRT
<213> ORGANISM: Cylicostephanus longibursatus

<400> SEQUENCE: 24

Met Asn Lys Thr Leu Thr Phe Leu Thr Val Val Tyr Ala Val Val Leu
1               5                   10                  15

Ala Gln Gly Val Met Asp Leu Phe Gly Glu Glu Gly Leu Glu Glu His
            20                  25                  30

Arg Arg His His Arg His Ser Leu Leu Pro Pro Tyr Leu His Asn Val
        35                  40                  45

Ser Cys Val Ala Lys Trp Glu Tyr Phe Lys Ile Leu Gly Asn Arg Ser
    50                  55                  60

Leu Thr Phe Ala Glu Lys Lys Glu Lys Ile Ser Glu Trp Ala Lys Lys
65                  70                  75                  80

Tyr Asn Val Val Asp Glu Val Ala Ser Tyr Asn Ala Cys Arg Glu Lys
                85                  90                  95

Leu Lys Gln Glu His Arg Lys Asn Val Ser Glu Ile Val Ser Asn Leu
            100                 105                 110

Pro Asn Ala Val Lys Lys Val Asn Asp Leu Leu Asp Asn Glu Asn Gln
        115                 120                 125

Thr Pro Arg Gln Leu Tyr Val Ala Leu Arg Lys Leu Gly Lys Gln Asn
    130                 135                 140

Pro Ala Leu Tyr Arg Val Glu Tyr Ile Asn Val Leu Val Arg Leu
145                 150                 155                 160

Arg Arg Glu Glu Phe Asp Glu Asp Gln Arg Arg Ser Leu Ser Ala Leu
                165                 170                 175

Pro Phe Gly Asp Asn Asn Asp Asp Leu Glu Glu Gln Asp Phe Gly Glu
            180                 185                 190

Gln Asp Phe Arg Tyr Ile Tyr Gly Phe Glu Cys Ala Arg Phe Ile Leu
        195                 200                 205

Gln Asn Gly Arg Met Phe Gly Leu Asn Thr Asp Arg Arg Tyr
    210                 215                 220

<210> SEQ ID NO 25
<211> LENGTH: 832
<212> TYPE: DNA
<213> ORGANISM: Cylicocyclus nassatus

<400> SEQUENCE: 25

```
atgaacaaaa cgttaacatt tctcatcgtc gttagtgccg tagtcctgac ccaaagtgtt      60
atggactttt tcgatgaaga cggtcgtgaa aacatcgcc gtcatcatcg tcattccctt     120
ttaccaccgt atctccacaa tatgagctgc gtggccaaat gggaatactt cgagattgtg    180
ggggacagga gtctgacgtt tgctgaaaag aaggaaaaaa tcggcgagtg ggctaaaaaa    240
tacaatgttg tggtaagatt ttgtaactct atgtaaagat accccgtac gtcgccctgt     300
ttaggatgaa gttgcaagct acaatgctta tagagaaaaa ctaaagcagg agcacaggaa    360
aaacgttagc gagcttgtct ctggtcttcc caatgctgtg aagaaaataa cgaacttt     420
agacaatgaa atcagactg ttaggcaact ttatgttgct ttaagagaac ttggtaaaca     480
aaatccagca gtaagttaaa agaagtgcaa ttttgggctt aactaatgag acaattttag    540
ctctaccgtg ttgtcgagta tatcaatgtg gttgtgagac ttagacgtga agatttggat    600
gagcaggaac aacagagaac gctgtcaacc ccaccttcg gcgagaataa cgaagagcaa     660
gactttggtg aacaagactt tcactatatc tatggttttg agtgtgccag attcatcctt    720
caaaatggaa gaatgtttgg acttaacacg gatagaagat attagtaaga gttaactgca    780
gctcaatgtg atagagattg agccacaacc caacatgcca tcatcacctc ct           832
```

<210> SEQ ID NO 26
<211> LENGTH: 220
<212> TYPE: PRT
<213> ORGANISM: Cylicocyclus nassatus

<400> SEQUENCE: 26

```
Met Asn Lys Thr Leu Thr Phe Leu Ile Val Val Ser Ala Val Val Leu
1               5                   10                  15

Thr Gln Ser Val Met Asp Phe Asp Glu Asp Gly Arg Glu Glu His
            20                  25                  30

Arg Arg His His Arg His Ser Leu Leu Pro Pro Tyr Leu His Asn Met
        35                  40                  45

Ser Cys Val Ala Lys Trp Glu Tyr Phe Glu Ile Val Gly Asp Arg Ser
    50                  55                  60

Leu Thr Phe Ala Glu Lys Lys Glu Lys Ile Gly Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Gly Leu
            100                 105                 110

Pro Asn Ala Val Lys Lys Ile Asn Glu Leu Leu Asp Asn Glu Asn Gln
        115                 120                 125

Thr Val Arg Gln Leu Tyr Val Ala Leu Arg Glu Leu Gly Lys Gln Asn
    130                 135                 140

Pro Ala Leu Tyr Arg Val Val Glu Tyr Ile Asn Val Val Arg Leu
145                 150                 155                 160

Arg Arg Glu Asp Leu Asp Glu Gln Glu Gln Arg Thr Leu Ser Thr
                165                 170                 175

Pro Pro Phe Gly Glu Asn Asn Glu Glu Gln Asp Phe Gly Glu Gln Asp
            180                 185                 190

Phe His Tyr Ile Tyr Gly Phe Glu Cys Ala Arg Phe Ile Leu Gln Asn
        195                 200                 205

Gly Arg Met Phe Gly Leu Asn Thr Asp Arg Arg Tyr
    210                 215                 220
```

<210> SEQ ID NO 27

```
<211> LENGTH: 762
<212> TYPE: DNA
<213> ORGANISM: Cylicocyclus nassatus

<400> SEQUENCE: 27
atgaacaaaa cgttaacatt tctcatcgtc gttagtgcca tagtcctggc ccaaagtgtt      60
atggactttt tcgatgaaga aggtcgtgag ggacatcgcc gtcatcatcg tcattcactt     120
ttaccaccat atctccacaa tatgagctgc gtggccaaat gggaatactt cgagattgtg     180
ggggacagga gtctgacgtt tgctgaaaag aaggaaaaaa tcggcgagtg ggctaaaaaa     240
tacaatgttg tggtaagatt ttgtaactcc atgttaggat acctccgcac gtcgccctgt     300
ttaggatgaa gttgcaagct acaatgctta tagagaaaaa ctaaagcagg agcacaggaa     360
aaacgttagc gagcttgtct ctggtcttcc caatgctgtg aagaaagtaa cgaacttttt     420
agacaatgaa atcagactg ttaggcaact ttatgttgct taagagaac ttggtaaaca       480
aaatccagca gtaagttaaa agaagtacaa ttttgagctc aactaatgag acaattttag     540
ctctaccgtg ttgtcgagta tatcaatgtg gttgtgagac ttagacgtga agattcggat     600
gagcaggaac aacgaagaac tctgtcaacc tcacctttcg gcgagaataa cgaagagcaa     660
gattttggtg aacaagattt tcactatatc tatggttttg agtgtgcaag attcatcctt     720
caaaatggaa gaatgtttgg actcaatacg gatagaagat at                        762

<210> SEQ ID NO 28
<211> LENGTH: 220
<212> TYPE: PRT
<213> ORGANISM: Cylicocyclus nassatus

<400> SEQUENCE: 28

Met Asn Lys Thr Leu Thr Phe Leu Ile Val Val Ser Ala Ile Val Leu
1               5                   10                  15

Ala Gln Ser Val Met Asp Phe Phe Asp Glu Glu Gly Arg Glu Gly His
            20                  25                  30

Arg Arg His His Arg His Ser Leu Leu Pro Pro Tyr Leu His Asn Met
        35                  40                  45

Ser Cys Val Ala Lys Trp Glu Tyr Phe Glu Ile Val Gly Asp Arg Ser
    50                  55                  60

Leu Thr Phe Ala Glu Lys Lys Glu Lys Ile Gly Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Gly Leu
            100                 105                 110

Pro Asn Ala Val Lys Lys Val Asn Glu Leu Leu Asp Asn Glu Asn Gln
        115                 120                 125

Thr Val Arg Gln Leu Tyr Val Ala Leu Arg Glu Leu Gly Lys Gln Asn
    130                 135                 140

Pro Ala Leu Tyr Arg Val Val Glu Tyr Ile Asn Val Val Arg Leu
145                 150                 155                 160

Arg Arg Glu Asp Ser Asp Glu Gln Glu Gln Arg Thr Leu Ser Thr
                165                 170                 175

Ser Pro Phe Gly Glu Asn Asn Glu Glu Gln Asp Phe Gly Glu Gln Asp
            180                 185                 190

Phe His Tyr Ile Tyr Gly Phe Glu Cys Ala Arg Phe Ile Leu Gln Asn
        195                 200                 205

Gly Arg Met Phe Gly Leu Asn Thr Asp Arg Arg Tyr
```

<210> SEQ ID NO 29
<211> LENGTH: 829
<212> TYPE: DNA
<213> ORGANISM: Cylicocyclus nassatus

<400> SEQUENCE: 29

```
atgaacaaaa cgttaacatt tctcatcgcc gttagtgcca tagtcctggc ccaaagtatg      60
gacttttcg atgaagacgg tcgtgaagaa catcgccgtc atcatcgtca ttcactttta     120
ccaccatatc tccacaatat gagctgcgcg gccaaatggg aatacttcga gattgtaggg     180
gacaggagtc tgacgtttgc tgaaaagaag gaaaaaatcg gcgagtgggc taaaaaatac     240
aatgttgtgg taagattttg taactccatg taaagatacc cctccatgtc gtcccgttta     300
ggatgaagtt gcaagctaca atgcttgcag agaaaaactg aagcaagagc acaggaaaaa     360
cgtcagcgag cttgtctctg gtcttcccaa tgctgtgaag aaagtaaacg aactttagaa     420
caatgaaaat cagactgtta ggcaacttta tgttgcttta agagaacttg gtaaacaaaa     480
tccagcagta agttgaaaga agtgcatttt gggcttaact aacgagacaa ttttagctct     540
accgtgttgt cgagtatatc aatgtggctg tgagacttag acgtgaagat tcggatgagc     600
aggaaaaacg aagaacgctg tcaacctcac ctttcggcga gaataacgaa gagcaggacc     660
ttggtgaaca agattttcac tatatctatg ctttgagtg tgcaagattc atccttcaaa     720
atggaagaat gtttggactt aacacggata gaagatatta gtaaaatttg actgcagctc     780
aaagtggtag agattgagct accaacccaa catgccatca tcacctcct                 829
```

<210> SEQ ID NO 30
<211> LENGTH: 219
<212> TYPE: PRT
<213> ORGANISM: Cylicocyclus nassatus

<400> SEQUENCE: 30

```
Met Asn Lys Thr Leu Thr Phe Leu Ile Ala Val Ser Ala Ile Val Leu
1               5                   10                  15

Ala Gln Ser Met Asp Phe Phe Asp Glu Asp Gly Arg Glu Glu His Arg
            20                  25                  30

Arg His His Arg His Ser Leu Leu Pro Pro Tyr Leu His Asn Met Ser
        35                  40                  45

Cys Ala Ala Lys Trp Glu Tyr Phe Glu Ile Val Gly Asp Arg Ser Leu
    50                  55                  60

Thr Phe Ala Glu Lys Lys Glu Lys Ile Gly Glu Trp Ala Lys Lys Tyr
65                  70                  75                  80

Asn Val Val Asp Glu Val Ala Ser Tyr Asn Ala Cys Arg Glu Lys Leu
                85                  90                  95

Lys Gln Glu His Arg Lys Asn Val Ser Glu Leu Val Ser Gly Leu Pro
            100                 105                 110

Asn Ala Val Lys Lys Val Asn Glu Leu Leu Asp Asn Glu Asn Gln Thr
        115                 120                 125

Val Arg Gln Leu Tyr Val Ala Leu Arg Glu Leu Gly Lys Gln Asn Pro
    130                 135                 140

Ala Leu Tyr Arg Val Val Glu Tyr Ile Asn Val Ala Val Arg Leu Arg
145                 150                 155                 160

Arg Glu Asp Ser Asp Glu Gln Glu Lys Arg Arg Thr Leu Ser Thr Ser
                165                 170                 175

Pro Phe Gly Glu Asn Asn Glu Glu Gln Asp Leu Gly Glu Gln Asp Phe
```

```
                180               185               190
His Tyr Ile Tyr Gly Phe Glu Cys Ala Arg Phe Ile Leu Gln Asn Gly
            195                 200                 205
Arg Met Phe Gly Leu Asn Thr Asp Arg Arg Tyr
        210                 215

<210> SEQ ID NO 31
<211> LENGTH: 840
<212> TYPE: DNA
<213> ORGANISM: Cyathostomum pateratum

<400> SEQUENCE: 31
atgaacaaaa cgttaacatt tctcacagtc gttagtgccg tagttctggc ccaaggtgtc    60
atggaccttt ttggtgaaga gggtcgtgaa gaacatcgtc gtcaccatcg tcattcactc   120
ttaccaccat atctccacaa tgtgagctgt gaggctaaat gggagtactt caaaattgtg   180
gggaacagga gtttgacgtt tgctgagaaa aaggagaaaa ttagcgagtg gcaaaaaaa    240 tacaatgttg tggtaagctt ttttgaattg atgtaaattc actcgcatgc tggcctttt    300 aggatgaagt tgcaagctac aatgcttaca gggaaaaact caagcaggag cacagaaaaa   360
acgttagcga acttgtttct gctcttccaa acgcagtaaa gaaagtcaac gatcttctag   420
acaatgaaaa tcagactctt aggcaacttt acgttgccct tagaaaactt ggtagacaaa   480
atccggcagt aagtcgaaag agctgcgtcc ttggacttaa gcggaaaaat tatttcagct   540
ttaccgtatt gtcgagtaca ttaatgtggc tgtaagacta agaagtgaag aagtggatga   600
gcaagaacaa cgaagaaggc tgtcagctct accttttggc gaccataacg ataatttgga   660
agagcaggac ttcggtgaac aagactttcg ctatgtctat ggctttgagt gtgcaagatt   720
tctccttcaa aatggaagaa tgttcggact caacacggga ggaagatatt agtaagaaac   780
aagtgtagct caaagtggta gagtttgagc tacgaactca acatgccatc atcacctcct   840

<210> SEQ ID NO 32
<211> LENGTH: 223
<212> TYPE: PRT
<213> ORGANISM: Cyathostomum pateratum

<400> SEQUENCE: 32

Met Asn Lys Thr Leu Thr Phe Leu Thr Val Val Ser Ala Val Leu
1               5                  10                  15

Ala Gln Gly Val Met Asp Leu Phe Gly Glu Glu Gly Arg Glu His
            20                  25                  30

Arg Arg His His Arg His Ser Leu Leu Pro Pro Tyr Leu His Asn Val
        35                  40                  45

Ser Cys Glu Ala Lys Trp Glu Tyr Phe Lys Ile Val Gly Asn Arg Ser
    50                  55                  60

Leu Thr Phe Ala Glu Lys Lys Glu Lys Ile Ser Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Ala Leu
            100                 105                 110

Pro Asn Ala Val Lys Lys Val Asn Asp Leu Leu Asp Asn Glu Asn Gln
        115                 120                 125

Thr Leu Arg Gln Leu Tyr Val Ala Leu Arg Lys Leu Gly Arg Gln Asn
    130                 135                 140

Pro Ala Leu Tyr Arg Ile Val Glu Tyr Ile Asn Val Ala Val Arg Leu
```

```
                    145                 150                 155                 160
Arg Ser Glu Glu Val Asp Glu Gln Glu Gln Arg Arg Arg Leu Ser Ala
                165                 170                 175

Leu Pro Phe Gly Asp His Asn Asp Asn Leu Glu Glu Gln Asp Phe Gly
                180                 185                 190

Glu Gln Asp Phe Arg Tyr Val Tyr Gly Phe Glu Cys Ala Arg Phe Leu
                195                 200                 205

Leu Gln Asn Gly Arg Met Phe Gly Leu Asn Thr Asp Gly Arg Tyr
                210                 215                 220
```

```
<210> SEQ ID NO 33
<211> LENGTH: 734
<212> TYPE: DNA
<213> ORGANISM: Cylicostephanus goldi

<400> SEQUENCE: 33
atgaacaaaa cgttaacatt tctcacagtc gttagtgccg ttgtcctggc ccaaggtgtc      60
atggccctat ttggtgaaga gagtcgtgaa gaacaccgcc gtcaccatcg tcattcactc     120
ttaccaccat atctccacaa cgtgagctgt gtggctaaat gggagtactt caaaattgtg     180
gggaacagga gtttgacgtt tgctgagaaa aagaaagaaa tcagcgagtg ggctaaaaaa     240
tacaatgttg tggatgaagt tgcaagctac aatgcttata gagaaaaact caagcaggaa     300
cacaggaaaa acgttagcga acttgtttct gatcttccca acgcagtaaa gaaagtcaac     360
gatcttttgg acaacgaaaa tcagacttct aggcaacttt atgttgcact cagagaactt     420
ggtagacaaa atccggcact ataccgtgtc gtcgagtata tcaatgtggc tgtgagatta     480
agacgaaaag aacaggatga caagaacga caaggaacgc tgtcagctct accttttggc     540
gagaataacg acaatttgga agagcaggac tttggtgaac aagactttcg ctatgtctat     600
ggctttgagt gtgcaagatt tctccttcaa aatggaagaa tgtttggact caacacggat     660
agaagatacc agtaagagtc aactgtagct caaagtgggt tgagctacg aacagcatgc     720
catcatcacc tcct                                                       734
```

```
<210> SEQ ID NO 34
<211> LENGTH: 223
<212> TYPE: PRT
<213> ORGANISM: Cylicostephanus goldi

<400> SEQUENCE: 34

Met Asn Lys Thr Leu Thr Phe Leu Thr Val Val Ser Ala Val Leu
1               5                   10                  15

Ala Gln Gly Val Met Ala Leu Phe Gly Glu Glu Ser Arg Glu His
                20                  25                  30

Arg Arg His His Arg His Ser Leu Leu Pro Pro Tyr Leu His Asn Val
                35                  40                  45

Ser Cys Val Ala Lys Trp Glu Tyr Phe Lys Ile Val Gly Asn Arg Ser
            50                  55                  60

Leu Thr Phe Ala Glu Lys Lys Lys Glu Ile Ser Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Asp Leu
                100                 105                 110

Pro Asn Ala Val Lys Lys Val Asn Asp Leu Leu Asp Asn Glu Asn Gln
                115                 120                 125
```

```
Thr Ser Arg Gln Leu Tyr Val Ala Leu Arg Glu Leu Gly Arg Gln Asn
        130                 135                 140

Pro Ala Leu Tyr Arg Val Val Glu Tyr Ile Asn Val Ala Val Arg Leu
145                 150                 155                 160

Arg Arg Lys Glu Gln Asp Glu Gln Glu Arg Gln Gly Thr Leu Ser Ala
                165                 170                 175

Leu Pro Phe Gly Glu Asn Asn Asp Asn Leu Glu Glu Gln Asp Phe Gly
                180                 185                 190

Glu Gln Asp Phe Arg Tyr Val Tyr Gly Phe Glu Cys Ala Arg Phe Leu
                195                 200                 205

Leu Gln Asn Gly Arg Met Phe Gly Leu Asn Thr Asp Arg Arg Tyr
        210                 215                 220

<210> SEQ ID NO 35
<211> LENGTH: 728
<212> TYPE: DNA
<213> ORGANISM: Cylicostephanus longibursatus

<400> SEQUENCE: 35
atgaacaaaa cgttaacatt tctcaccgtc gtctatgccg tagtcctggc ccaaggtgtc      60
atggaccttt ttggtgaaga gggtcgtgaa gaacatcgcc gtcaccatcg tcattcactc     120
ttaccaccat atctccacaa tgtgagctgt gtggctaaat gggaatactt caaaattctg     180
gggaacagga gtttgacgtt tgctgagaaa aaggaaaaaa tcagcgagtg ggcaaagaag     240
tacaatgttg tggatgaagt tgcaagctat aatgcttgca gggaaaagct taagcaggaa     300
cacaggaaaa acgttagcga aattgtttct aatcttccca atgcagtgaa gaaagtaaac     360 gatctttttgg acaatgaaaa tcagaccccc aggcaacttt acgttgccct cagaaaactt     420
ggtaaacaaa atccggcact ttatcgtgtt gtcgagtata tcaatgtgct tgtgagacta     480
agacgtgaag aatttgatga agatcaacga agatcgctgt cagctttacc ttttggcgac     540
aataacgacg atttggaaga gcaggacttt ggtgaacagg actttcgcta tatctatggc     600
tttgagtgtg caagatttat ccttcaaaat ggaagaatgt tcggaatcaa cacggataga     660
agatattagt aagagtcaac tgtagctcaa gggtttgagc tacgaactgc atgccatcat     720
cacctcct                                                              728

<210> SEQ ID NO 36
<211> LENGTH: 222
<212> TYPE: PRT
<213> ORGANISM: Cylicostephanus longibursatus

<400> SEQUENCE: 36

Met Asn Lys Thr Leu Thr Phe Leu Thr Val Val Tyr Ala Val Val Leu
1               5                   10                  15

Ala Gln Gly Val Met Asp Leu Phe Gly Glu Glu Gly Arg Glu Glu His
                20                  25                  30

Arg Arg His His Arg His Ser Leu Leu Pro Pro Tyr Leu His Asn Val
            35                  40                  45

Ser Cys Val Ala Lys Trp Glu Tyr Phe Lys Ile Leu Gly Asn Arg Ser
        50                  55                  60

Leu Thr Phe Ala Glu Lys Lys Glu Lys Ile Ser Glu Trp Ala Lys Lys
65                  70                  75                  80

Tyr Asn Val Val Asp Glu Val Ala Ser Tyr Asn Ala Cys Arg Glu Lys
                85                  90                  95

Leu Lys Gln Glu His Arg Lys Asn Val Ser Glu Ile Val Ser Asn Leu
                100                 105                 110
```

-continued

```
Pro Asn Ala Val Lys Lys Val Asn Asp Leu Leu Asp Asn Glu Asn Gln
        115                 120                 125

Thr Pro Arg Gln Leu Tyr Val Ala Leu Arg Lys Leu Gly Lys Gln Asn
    130                 135                 140

Pro Ala Leu Tyr Arg Val Val Glu Tyr Ile Asn Val Leu Val Arg Leu
145                 150                 155                 160

Arg Arg Glu Glu Phe Asp Glu Asp Gln Arg Arg Ser Leu Ser Ala Leu
                165                 170                 175

Pro Phe Gly Asp Asn Asn Asp Asp Leu Glu Glu Gln Asp Phe Gly Glu
            180                 185                 190

Gln Asp Phe Arg Tyr Ile Tyr Gly Phe Glu Cys Ala Arg Phe Ile Leu
        195                 200                 205

Gln Asn Gly Arg Met Phe Gly Ile Asn Thr Asp Arg Arg Tyr
    210                 215                 220

<210> SEQ ID NO 37
<211> LENGTH: 132
<212> TYPE: PRT
<213> ORGANISM: Cyathostomum sp.

<400> SEQUENCE: 37

Arg Glu Lys Ala Arg Ile Ile Gln Asp Glu Tyr Thr Lys Arg Met Gln
1               5                   10                  15

Gln Val Thr Pro Gln Ala Gln Glu Phe Leu Ala Lys Trp Glu Lys Thr
            20                  25                  30

Trp Phe Thr Asn Val Gln Gln Tyr Ser Gly Asp Lys Lys Ala Phe Phe
        35                  40                  45

Lys Gln Met Ile Glu Leu Ile Pro Gln Leu Met Glu Glu Val His Gly
    50                  55                  60

Phe Ser Glu Glu Thr Trp Lys Ser Leu Glu Glu Gln Phe Pro Glu Gln
65                  70                  75                  80

Thr Ala Ala Trp Lys Asp Asn Glu Asp Arg Leu Lys Gln Phe Tyr Glu
                85                  90                  95

Phe Ile Lys Ser Leu Pro Lys Gln Asp Leu Ala Glu Asp Pro Glu Ala
            100                 105                 110

Phe Arg Lys Phe Ala His Leu Gly Leu Gln Lys Leu Leu Pro Ile Glu
        115                 120                 125

Ala Leu Arg Ala
    130

<210> SEQ ID NO 38
<211> LENGTH: 396
<212> TYPE: DNA
<213> ORGANISM: Cyathostomum sp.

<400> SEQUENCE: 38
agggagaagg ctagaattat tcaagacgaa tacactaaac gtatgcagca ggtcacacca      60
caagctcagg aattcctggc aaaatgggag aagacatggt tcacgaatgt gcagcaatat     120
agcggagata agaaagcttt cttcaagcag atgattgagc taatccctca actaatggag     180
gaggttcatg ggttctcgga agagacttgg aagagccttg aggagcaatt cccagagcag     240
acagccgcat ggaaagataa tgaggatcgc ctaaagcaat tttatgagtt tatcaagagc     300
ctacccaagc aggacttagc tgaggatccg gaagcattca gaaagttcgc tcacctcgga     360
ctccagaaac ttcttccaat tgaagctctc agagct                               396
```

<210> SEQ ID NO 39
<211> LENGTH: 565
<212> TYPE: DNA
<213> ORGANISM: Cyathostomum catinatum.

<400> SEQUENCE: 39

```
tggtcacacc acaagctcag gagttcctgg ccaaggtaag ctattacctt accagggtga        60
ggggaaagaa gttggcagcg gtcggaaacc cggtaatcta ctgactttac caattatttt       120
cagtgggaga agacatggtt cacgaatata cagcaataca gtggagacaa gcaagccttc       180
tttaagcaga tgattgaact aattcctcaa cttatggagg aggttcaggt aagttagccg       240
caaaaatttt taaccaatgg ttgagctcga cattttttca gggattcaca gaggagactt       300
ggaatagcct gagggagcaa ttcccggagc agacagccgc atggaaggat cgtgagtatc       360
tttcataatt actgtacttg gaattatact ttacaatcat aatcctactc ttagacgagg       420
atcgcctgaa gcaattctat gagttcatta agagcctacc caaacaacaa ttagctgagg       480
tgattttcat tgattttcg aaaaatatat ttttgataca ttcttttca ggatccggaa        540
gctttcagaa agttcgctca cctcg                                            565
```

<210> SEQ ID NO 40
<211> LENGTH: 569
<212> TYPE: DNA
<213> ORGANISM: Cyathostomum catinatum.

<400> SEQUENCE: 40

```
ttgtcacacc acaagctcag gagttcctgg ctaaggtaag ctattacctt accagggtga        60
gggggaagaa gttgggagcg gtcggaaacc cggtaatcta ctgactttac caattatttt       120
cagtgggaga ggacatggtt cacgaatata cagcaataca gtggagacaa gcaagccttc       180
tttaagcaga tgattgaact aattcctcaa cttatggagg aggttcaggt aagttggccg       240
caaaaatttt taaccaatgg ttgagctcga cattttttca gggattcaca gaggagactt       300
ggaatagcct gagggagcaa ttcccggagc agacagccgc atggaaggat cgtaagtatc       360
tttcataatt actgtacttg gaattatact ttacaatcat aatcctactc ttagacgagg       420
atcgcctgaa gcaattctat gagttcatta agagcctacc caaacaacaa ttagctgagg       480
tgattttcat tgattttcg tacgaaaaat atttttga tacattcttt ttcaggatcc         540
ggaagctttc agaaagttcg ctcacctcg                                        569
```

<210> SEQ ID NO 41
<211> LENGTH: 561
<212> TYPE: DNA
<213> ORGANISM: Cylicostephanus longibursatus

<400> SEQUENCE: 41

```
aggtcacacc acaagctcag gaattcctgg caaaggtaag ctatcacctt accagggtga        60
ggggtagaag ttaggagcga gggaacccgg tgatctctta tacccattac ttcagtggga       120
gaagatatgg ttcacgaatg tacagcaata tagtggagac aagcaagcct tcttcaagca       180
gatgattgaa ctaattcctc aacttatgga ggaggtacag gtaagtcagc taaagtgatt       240
ttaagaaaaa attaagcctg attttccttt cagggattct cagaggagac ttggaatagc       300
cttaaggagc aattccctga gcagacagcc gcatggaagg atagtgagta tttttcataa       360
ttactgtact tggaattata ctttacaatc ataatcctac cctcagacga ggagcgcctg       420
aagcaattct atgagttcat taagagccta cccaaacaac aaatagctga ggtgattttc       480
attgattttt cgtacgaaaa gtatattttt aatacattct tttgcaggat ccggaagcct       540
```

```
tcagaaagtt cgctcacctc g                                              561
```

<210> SEQ ID NO 42
<211> LENGTH: 589
<212> TYPE: DNA
<213> ORGANISM: Cylicocyclus nassatus

<400> SEQUENCE: 42

```
aggtcacacc acaagctcag gaattcctgg caaaggtaag ctaccatatt tcgagggggga    60
gggcaattt  ggagcgaggg aggagaggaa agggagagaa acactggttg ggatcactaa   120
ctctacccgc cacttccagt gggagaagac atggttcacg aatgtgcagc aatatagcgg   180
agataagaaa gccttttca aacagatgat tgagctaatc cctcaactaa tggaagaggt   240
tcatgtaagt caaccaaagt ggcttttaag cggagattaa actcgaattt ttcttcaggg   300
gttctcggag gagacttgga agagccttga ggagcaattc ccagagcaga cagccgcatg   360
gaaggatagt aagcattctt catagctccc gcctttatca tttatcttca cgatagtaat   420
cttatttta gatgaggatc gcctgaagca attttatgag ttcatcaaga gcctacccaa   480
gcaggactta gctgaggtaa ctttcatggt tttttcctga gctgtaaaaa tgcttgcaac   540
taacaacttt tctaggatcc ggaagctttc agaaagttcg ctcacctcg              589
```

<210> SEQ ID NO 43
<211> LENGTH: 195
<212> TYPE: PRT
<213> ORGANISM: Cyathostomum sp.

<400> SEQUENCE: 43

```
Lys Lys Glu Ser Gln Gly Phe Phe Ser Ile Pro Val Asp Asn Leu Arg
  1               5                  10                  15

Ala Ser Pro Phe Leu Leu Gln Tyr Ile Lys Glu Tyr Ile Pro Asp Tyr
                 20                  25                  30

Lys Asn Ala Met Glu Lys Phe Glu Asp Ile Pro Lys Gln Tyr Arg Asp
             35                  40                  45

Leu Ile Pro Glu Glu Val Ala Thr His Leu Lys Ala Ile Thr Ala Glu
         50                  55                  60

Glu Lys Ala Val Leu Lys Glu Val Met Lys Asp Tyr Ala Lys Tyr Lys
 65                  70                  75                  80

Asp Glu Glu Glu Phe Leu Lys Ala Leu Lys Glu Lys Ser Glu Gly Leu
                 85                  90                  95

His Glu Lys Ala Ser Lys Leu His Asn Phe Ile Lys Gly Lys Val Asp
            100                 105                 110

Ala Leu Gly Asp Glu Ala Lys Ala Phe Val Lys Lys Val Ile Ala Ala
        115                 120                 125

Ala Arg Glu Val His Ala Lys Leu Leu Ala Gly Asp Lys Pro Ser Leu
    130                 135                 140

Glu Asp Ile Lys Lys Lys Ala Lys Glu His Met Gly Glu Phe Glu Lys
145                 150                 155                 160

Leu Ser Asp Asp Ala Lys Glu Asp Leu Lys Lys Asn Phe Pro Ile Leu
                165                 170                 175

Thr Ser Val Trp Thr Asn Glu Lys Thr Arg Ala Leu Ile Asp Lys Tyr
            180                 185                 190

Val Glu Asn
        195
```

<210> SEQ ID NO 44

```
<211> LENGTH: 573
<212> TYPE: DNA
<213> ORGANISM: Cyathostomum sp.

<400> SEQUENCE: 44
atgcttcgaa taactttctt ccttgctctc tttgttgtct acacttttc tgcaccctct      60 ggacccgctg aagagaagat agatgtggaa aaaatggaaa aatttgaaga tattccaaag    120
caatatcgag accttattcc ggaagaggta gctacacacc tcaaagccat caccgctgaa    180
gagaaagctg ttctaaaaga ggtaatgaag aattatgcaa agtacaagaa cgaggaggag    240
tttttggaag cgttgaaaga aaaatcagag agtttgcatg agaaagccag caaacttcac    300
aattttatca agggaaggt tgacgcactt ggagatgaag caaaggcatt tgtgaagaag     360
gttatcgcag ctgctcgaga agtgcatgcc aaacttcttg ccggggacaa accatcgctt    420
gaagatatca agaagaaagc caaggagcat atggctgaat cgagaaaact aagcgatgat    480
gccaaggagg atctcaaaaa gaatttccca atccttactt ccgtctggac aaatgagaaa    540
acaagagcgt tgattgacaa atatgtggag aac                                 573

<210> SEQ ID NO 45
<211> LENGTH: 145
<212> TYPE: PRT
<213> ORGANISM: Cyathostomum sp.

<400> SEQUENCE: 45

Gly Lys Met Ser Asp Leu Trp Thr Ala Ile Ser Glu Thr Asn Lys Val
1               5                   10                  15

Arg Leu Phe Asn Thr Leu Ser Leu Gly Ile Ala Gly Val Leu Cys Ile
            20                  25                  30

Thr Thr Ala Phe Ile Pro Val Glu Asn Gln Val Val Cys Ala Val Leu
        35                  40                  45

Ile Thr Leu Leu Gln Gly Val Ile Gly Phe Asn Ser Ala Gly Tyr Asn
    50                  55                  60

Lys Ala Ala Val Ile Val Ala Arg Gln His Ala His Leu Leu Leu Thr
65                  70                  75                  80

Cys Phe Gly Leu Ile Val Thr Phe Val Pro Leu Val Gln Pro Phe Ile
                85                  90                  95

Val Gln Leu Val Ala Pro Asp His Ser Trp Asp Gln Trp Phe Tyr Leu
            100                 105                 110

Phe Val Gly His Gly Leu Val Leu Val Ile Ala Asn Leu Phe Phe Cys
        115                 120                 125

Leu Thr Ile Glu Ala Lys Pro Ala Ala Phe Thr Gln Lys Thr Asp Ser
    130                 135                 140

Ser
145

<210> SEQ ID NO 46
<211> LENGTH: 435
<212> TYPE: DNA
<213> ORGANISM: Cyathostomum sp.

<400> SEQUENCE: 46
ggtaaaatgt cagatttatg gacggcaata agcgaaacaa ataaagtccg cttgttcaac     60
accttgtcgc tgggaattgc tggcgtactg tgtataacta ctgctttcat tcctgtggaa    120
aatcaggttg tttgcgctgt tttaatcacg ttattgcaag gagttatcgg attcaattca    180
gctggatata caaagctgc agtcattgtt gctaggcagc atgctcatct tctgttgacc    240
```

```
tgctttgggc tcattgtcac ttttgtcccc ttggtgcagc cattcatagt tcaacttgtg      300
gcccctgacc atagctggga ccaatggttt tatctgtttg ttgggcatgg tctcgtactt      360
gttatagcga atttattctt ttgtctcact atcgaggcga aaccggcagc gttcacacag      420
aaaactgatt catca                                                       435

<210> SEQ ID NO 47
<211> LENGTH: 173
<212> TYPE: DNA
<213> ORGANISM: Cyathostomum sp.

<400> SEQUENCE: 47
ggtttaatta cccaagtttg aggtactttc taaatctgac ccgatcaact gattgtggtc       60
tgattaaatt ttgaaaatct ctccctgaat agggagagta caagagtgca tatccaaaaa      120
aaaaaaaaaa aaaaaaaaaa aaaacatgt cggccgcctc ggcctctaga ata              173

<210> SEQ ID NO 48
<211> LENGTH: 287
<212> TYPE: DNA
<213> ORGANISM: Cyathostomum sp.

<400> SEQUENCE: 48
ggtttaatta cccaagtttg agtgtcatga agcttgcctg aaaaaagcag agaaaccaag       60
aggagatagt ttcacagttc cgccagacag gaaatgcgtg ccaagatgtt ttgcggaaga      120
ggagaaacgt cgttcactta gaatgagaag gcattgattc tgtttagtcg ttagatatt      180 taaaaattct ttgcagaaaa ccttttcaaa tcataaagtc gaagaccaca aaaaaaaaa      240 aaaaaaaaaa aaaaaaaaac atgtcggccg cctcggcctc tagaata                   287

<210> SEQ ID NO 49
<211> LENGTH: 620
<212> TYPE: DNA
<213> ORGANISM: Cyathostomum sp.

<400> SEQUENCE: 49
ggtttaatta cccaagtttg aggctgcttc aacagtaggt ttagaaatga catcgcggat       60
atggcgccgc acccagagcc ctccattatt gctactcctg ttgttgatca gtctaccagt      120
agctgagtgt agtattcgac tatgtggagt gcgactaaca cgaactctta tggctatctg      180
caggaatcaa ttatgcggtt attcgcaaag taaagatct gctatgtggg aagagcctcg      240
actggaaacc gtgcactcaa caatgaaacg atcagggatc gccaccgaat gctgcgagaa      300
tcggtgctca tttagctact aaagacata ctgctgcagc acttagcctt ggcatcttaa      360
gccgctttta tctcctctcc atgatctctc ttcgttatct gtataaccga atatagtcat      420
tccggaaatg cggatgctta ggccaatttg ttgacgtttg ccgcatgaat catttgctgt      480
tcgtcattat ctcacagacg tgtaaaagat ctctttttat gaaagtctat tttgtttgag      540
ctgcaccatt aaaccgttca caaaaaaaaa aaaaaaaaaa aaaaaaaaaa acatgtcggc      600
cgcctcggcc tctagaataa                                                  620

<210> SEQ ID NO 50
<211> LENGTH: 172
<212> TYPE: DNA
<213> ORGANISM: Cyathostomum sp.

<400> SEQUENCE: 50
ggtttaatta cccaagtttg aggtactttc tagatctgac ccgatcaact gattgtggtc       60
```

```
tgattaaatt ttggaaatct cttcctgaac agggagagta caagagtgta tatgaaaaaa    120
aaaaaaaaaa aaaaaaaaaa aaaacatgtc ggccgcctcg gcctctagaa ta            172

<210> SEQ ID NO 51
<211> LENGTH: 327
<212> TYPE: DNA
<213> ORGANISM: Cyathostomum sp.

<400> SEQUENCE: 51
ggtttaatta cccaagtttg aggatgctta gtttcaagct cgttcttctc ttcgtacttc    60
tcacagcttg tgtgctaaca gatccaagag tgttaatccg agaaaagcga atggactgga   120
gacgttacta tagcagatgg ggtcgcggaa gctctaattg gggaaaccgc ggaggtacct   180
tcggcggacg aaaatggagt tacccgactt ttggacaatg gggacattaa catctgatgt   240
atgaaaagat ctaatgaaat aaagcttcga aaaaaaaaaa aaaaaaaaaa aaaaaaaac    300 atgtcggccg cctcggcctc tagaata                                       327

<210> SEQ ID NO 52
<211> LENGTH: 324
<212> TYPE: DNA
<213> ORGANISM: Cyathostomum sp.

<400> SEQUENCE: 52
ggtttaatta cccaagtttg agaatgttcg aaaaattcct tctgctactg atcgttgtga    60
tcgccctcat ttctttggcg tctgcagatt tttcatgctt cttcggtgat accatctgca   120
agagcattac atgcaggggc tgcaccgtcg ccacttgcct taatggagac tgtatgtgca   180
cactatgtaa ctgatgatct tcacatgtcg cattaccatt tgtaacaaat acattttctc   240
ttgttcataa taaattttc actcaaaaaa aaaaaaaaaa aaaaaaaaaa aaaaacatg     300 tcggccgcct cggcctctag aata                                          324

<210> SEQ ID NO 53
<211> LENGTH: 328
<212> TYPE: DNA
<213> ORGANISM: Cyathostomum sp.

<400> SEQUENCE: 53
ggccgcggga ttttctagag gccgaggcgg gttttaggtt gttcctcaaa cttgggtaat    60
taaaccacga ggccgaggcg ggttttaggt tgttctcaaa cttgggtaat taaaccacga   120
tggcgaggcg ggttttaggt tgttctcaaa cttgggtaat taaaccacga tggcgaggcg   180
ggttttaggt tgttcctcaa acttgggtaa ttaaaccaag aggccgaggc gggttttagg   240
ttgttcctca acttgggta attaaaccac gatggcgagg cgggttttag gttgttctca    300
aacttgggta attaaaccaa tcactagt                                      328

<210> SEQ ID NO 54
<211> LENGTH: 154
<212> TYPE: DNA
<213> ORGANISM: Cyathostomum sp.

<400> SEQUENCE: 54
ggccgcggga ttattctaga ggccgaggca gtggtatcaa cgcagagtgg ccattacggc    60
cggggagagg gaaaagtttc ttttctctcg gataccaaaa aaaaaaaaaa aaaaaaaaaa   120
aaaaaacatg tcggccgcct cggcctctag aata                               154

<210> SEQ ID NO 55
```

```
<211> LENGTH: 387
<212> TYPE: DNA
<213> ORGANISM: Cyathostomum sp.

<400> SEQUENCE: 55
ggccgcggga ttttctagag gccgaggcgt cttacttggg tggctcaata actgaaagct      60
tagaattcat taaaccttaa cccacagggg ttatttgaca tgcttgactt gaaaatgatg     120
ctcttctgct tgtagttgtt ttattatgct agctgtaagt atactctggt agaccagaac     180
atcaatgtgc tagttgaatg tatcatgtta tcactttgtc acactctata cgaatctagg     240
tgtggcaggc cacacccctc tcctgaccct gttcaccatc aattagcttt tagctgttat     300
ttaataacat cacactgatt gcaaaaaaaa aaaaaaaaa aaaaaaaaaa acatgtcggc     360
cgcctcggcc tctaaaaaat cactagt                                         387

<210> SEQ ID NO 56
<211> LENGTH: 292
<212> TYPE: DNA
<213> ORGANISM: Cyathostomum sp.

<400> SEQUENCE: 56
ggccgcggga ttattctaga ggccgaggca gtggtatcaa cgcagagtgg ccattacggc      60
cgaagcagtg gtatcaacgc agagtggcca ttacggccgg tggtgacca cgggtgacgg     120 ggaattaggg ttcgattccg agagggagc ctgagaaacg gctaccacat ccaaggaagg     180
cagcaggcgc gcaaattacc cactcccgac ccggggaggt agtgacgaaa aaaaaaaaa     240 aaaaaaaaa aaaacatgt cggccgcctc ggcctctaga ataatcacta gt              292

<210> SEQ ID NO 57
<211> LENGTH: 199
<212> TYPE: DNA
<213> ORGANISM: Cyathostomum sp.

<400> SEQUENCE: 57
ggccgcggga ttttctagag gccgaggcgg gttttagctc aaacttgggt aattaaaccg      60
gtaggatggc gaggcgggtt tctcaaactt gggtaattaa accagtagga tggcgaggcg     120
ggtttctcaa acttgggtaa ttaaaccggt aggaggccga ggcgggtctc aaacttgggt     180
aattaaacca atcactagt                                                  199

<210> SEQ ID NO 58
<211> LENGTH: 167
<212> TYPE: DNA
<213> ORGANISM: Cyathostomum sp.

<400> SEQUENCE: 58
caagtttgag gtactttcta gatctgaccc gatcaactga ttgtggtctg attaaatttt      60
ggaaatctct tcctgaacag ggagagtaca agagtgtata ttaagaaaaa aaaaaaaaa     120 aaaaaaaaa catgtcggcc gcctcggcct ctagaataat cactagt                   167

<210> SEQ ID NO 59
<211> LENGTH: 22
<212> TYPE: DNA
<213> ORGANISM: Artificial
<220> FEATURE:
<223> OTHER INFORMATION: Primer

<400> SEQUENCE: 59
ggtttaatta cccaagtttg ag                                               22
```

```
<210> SEQ ID NO 60
<211> LENGTH: 17
<212> TYPE: DNA
<213> ORGANISM: Artificial
<220> FEATURE:
<223> OTHER INFORMATION: Primer

<400> SEQUENCE: 60
attctagagg ccgaggc                                                    17

<210> SEQ ID NO 61
<211> LENGTH: 17
<212> TYPE: DNA
<213> ORGANISM: Artificial
<220> FEATURE:
<223> OTHER INFORMATION: Primer

<400> SEQUENCE: 61
ttctagaggc cgaggcg                                                    17

<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62
aaaaaggagg tgtttggttc                                                 20

<210> SEQ ID NO 63
<211> LENGTH: 23
<212> TYPE: DNA
<213> ORGANISM: Artificial
<220> FEATURE:
<223> OTHER INFORMATION: Primer

<400> SEQUENCE: 63
cttgaatttg ataaaactac acc                                             23

<210> SEQ ID NO 64
<211> LENGTH: 18
<212> TYPE: DNA
<213> ORGANISM: Artificial
<220> FEATURE:
<223> OTHER INFORMATION: Primer

<400> SEQUENCE: 64
aattgtgggg aacaggag                                                   18

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
aatgaaaatc agactcctag g                                               21

<210> SEQ ID NO 66
<211> LENGTH: 34
<212> TYPE: DNA
<213> ORGANISM: Artificial
<220> FEATURE:
<223> OTHER INFORMATION: Primer
```

-continued

```
<400> SEQUENCE: 66
aattcggatc cgcaaggtgt catggacctt tttg                                34

<210> SEQ ID NO 67
<211> LENGTH: 38
<212> TYPE: DNA
<213> ORGANISM: Artificial
<220> FEATURE:
<223> OTHER INFORMATION: Primer

<400> SEQUENCE: 67
ccgcaagctt atatctttca tctgtgttga gtccaaac                            38

<210> SEQ ID NO 68
<211> LENGTH: 60
<212> TYPE: PRT
<213> ORGANISM: Cyclicoclyclus ashworthi
<220> FEATURE:
<221> NAME/KEY: MISC_FEATURE
<222> LOCATION: (43)..(43)
<223> OTHER INFORMATION: X is E or V
<220> FEATURE:
<221> NAME/KEY: MISC_FEATURE
<222> LOCATION: (50)..(50)
<223> OTHER INFORMATION: X is G or D
<220> FEATURE:
<221> NAME/KEY: MISC_FEATURE
<222> LOCATION: (57)..(57)
<223> OTHER INFORMATION: X is E or V

<400> SEQUENCE: 68

Leu Thr Phe Ala Glu Lys Lys Gly Lys Ile Ser Glu Trp Ala Lys Lys
1               5                   10                  15

Tyr Asn Val Val Asp Glu Val Ala Ser Tyr Asn Ala Tyr Arg Glu Lys
            20                  25                  30

Leu Lys Gln Glu His Arg Lys Asn Val Ser Xaa Leu Val Ser Gly Leu
        35                  40                  45

Pro Xaa Ala Val Lys Lys Val Asn Xaa Leu Leu Asp
    50                  55                  60

<210> SEQ ID NO 69
<211> LENGTH: 60
<212> TYPE: PRT
<213> ORGANISM: Cyathostomum catinatum
<220> FEATURE:
<221> NAME/KEY: misc_feature
<222> LOCATION: (8)..(8)
<223> OTHER INFORMATION: Xaa can be any naturally occurring amino acid

<400> SEQUENCE: 69

Leu Thr Phe Ala Glu Lys Lys Xaa Glu Ile Ser Glu Trp Ala Lys Lys
1               5                   10                  15

Tyr Asn Val Val Asp Glu Val Ala Ser Tyr Asn Ala Tyr Arg Glu Lys
            20                  25                  30

Leu Lys Gln Glu His Arg Lys Asn Val Ser Glu Leu Val Ser Ala Leu
        35                  40                  45

Pro Asn Ala Val Lys Lys Val Asn Asp Leu Leu Asp
    50                  55                  60

<210> SEQ ID NO 70
<211> LENGTH: 60
<212> TYPE: PRT
<213> ORGANISM: Coronocyclus coronatus

<400> SEQUENCE: 70
```

```
Leu Thr Phe Ala Glu Lys Lys Glu Ile Ser Glu Trp Ala Lys Lys
1               5                   10                  15

Tyr Lys Val Glu Asp Glu Val Ala Ser Tyr Asn Ala Tyr Arg Glu Lys
                20                  25                  30

Leu Lys Gln Glu His Arg Lys Asn Val Ser Glu Leu Val Ser Ala Leu
            35                  40                  45

Pro Gly Ala Val Lys Lys Val Asn Glu Leu Leu Asp
    50                  55                  60
```

<210> SEQ ID NO 71
<211> LENGTH: 60
<212> TYPE: PRT
<213> ORGANISM: Cylicostephanus goldi

<400> SEQUENCE: 71

```
Leu Thr Phe Ala Glu Lys Lys Glu Ile Ser Glu Trp Ala Lys Lys
1               5                   10                  15

Tyr Asn Val Val Asp Glu Val Ala Ser Tyr Asn Ala Tyr Arg Glu Lys
                20                  25                  30

Leu Lys Gln Glu His Arg Lys Asn Val Ser Glu Leu Val Ser Asp Leu
            35                  40                  45

Pro Ser Ala Val Lys Lys Val Asn Asp Leu Leu Asp
    50                  55                  60
```

<210> SEQ ID NO 72
<211> LENGTH: 60
<212> TYPE: PRT
<213> ORGANISM: Coronocyclus labiatus

<400> SEQUENCE: 72

```
Leu Thr Phe Ala Glu Lys Lys Glu Ile Ser Glu Trp Ala Lys Lys
1               5                   10                  15

Tyr Asn Val Val Asp Glu Val Ala Arg Tyr Asn Ala Tyr Arg Glu Lys
                20                  25                  30

Leu Lys Gln Glu Tyr Arg Lys Asn Val Ser Glu Leu Val Ser Gly Leu
            35                  40                  45

Pro Asn Ala Val Lys Lys Val Asn Asp Leu Leu Asp
    50                  55                  60
```

<210> SEQ ID NO 73
<211> LENGTH: 60
<212> TYPE: PRT
<213> ORGANISM: Cylicocyclus leptostomum

<400> SEQUENCE: 73

```
Leu Thr Phe Ala Glu Lys Lys Gly Lys Ile Ser Glu Trp Ala Lys Lys
1               5                   10                  15

Tyr Asn Val Val Asp Glu Val Ala Ser Tyr Asn Ala Tyr Arg Glu Lys
                20                  25                  30

Leu Lys Gln Glu His Arg Lys Asn Val Ser Glu Leu Val Ser Gly Leu
            35                  40                  45

Pro Gly Ala Val Lys Lys Val Asn Glu Leu Leu Asp
    50                  55                  60
```

<210> SEQ ID NO 74
<211> LENGTH: 60
<212> TYPE: PRT
<213> ORGANISM: Cylicostephanus longibursatus

<400> SEQUENCE: 74

```
Leu Thr Phe Ala Glu Lys Lys Glu Ile Ser Lys Trp Ala Lys Lys
1               5                   10                  15

Tyr Asn Val Val Asp Glu Val Ala Ser Tyr Asn Ala Tyr Arg Glu Lys
            20                  25                  30

Leu Lys Gln Glu His Arg Lys Asn Val Ser Glu Ile Val Ser Asp Leu
        35                  40                  45

Pro Asn Ala Val Lys Lys Val Asn Asp Leu Leu Asp
    50                  55                  60

<210> SEQ ID NO 75
<211> LENGTH: 60
<212> TYPE: PRT
<213> ORGANISM: Cylicostephanus minutus

<400> SEQUENCE: 75

Leu Thr Phe Ala Glu Lys Lys Glu Lys Ile Ser Glu Trp Ala Lys Lys
1               5                   10                  15

Tyr Asn Val Val Asp Glu Val Ala Ser Tyr Asn Ala Tyr Arg Glu Lys
            20                  25                  30

Leu Lys Gln Glu His Arg Lys Asn Val Ser Gln Leu Val Ser Ala Leu
        35                  40                  45

Pro Asn Ala Val Lys Lys Val Asn Asp Leu Leu Asp
    50                  55                  60

<210> SEQ ID NO 76
<211> LENGTH: 60
<212> TYPE: PRT
<213> ORGANISM: Cylicocyclus nassatus
<220> FEATURE:
<221> NAME/KEY: misc_feature
<222> LOCATION: (25)..(25)
<223> OTHER INFORMATION: Xaa can be any naturally occurring amino acid

<400> SEQUENCE: 76

Leu Thr Phe Ala Glu Lys Lys Glu Lys Ile Gly Glu Trp Ala Lys Lys
1               5                   10                  15

Tyr Asn Val Val Asp Glu Val Ala Xaa Tyr Asn Ala Tyr Arg Glu Lys
            20                  25                  30

Leu Lys Gln Glu His Arg Lys Asn Val Ser Glu Leu Val Ser Gly Leu
        35                  40                  45

Pro Asn Ala Val Lys Lys Val Asn Glu Leu Leu Asp
    50                  55                  60

<210> SEQ ID NO 77
<211> LENGTH: 60
<212> TYPE: PRT
<213> ORGANISM: Cyathostomum pateratum
<220> FEATURE:
<221> NAME/KEY: MISC_FEATURE
<222> LOCATION: (8)..(8)
<223> OTHER INFORMATION: X is K or E

<400> SEQUENCE: 77

Leu Thr Phe Ala Glu Lys Lys Xaa Glu Ile Ser Glu Trp Ala Lys Lys
1               5                   10                  15

Tyr Asn Val Val Asp Glu Val Ala Ser Tyr Asn Ala Tyr Arg Glu Lys
            20                  25                  30

Leu Lys Gln Glu His Arg Lys Asn Val Ser Glu Leu Val Ser Ala Leu
        35                  40                  45

Pro Asn Ala Val Lys Lys Val Asn Asp Leu Leu Asp
    50                  55                  60
```

<210> SEQ ID NO 78
<211> LENGTH: 223
<212> TYPE: PRT
<213> ORGANISM: Cyathostomum pateratum

<400> SEQUENCE: 78

Met Asn Lys Thr Leu Thr Phe Leu Thr Val Val Ser Ala Val Ala Leu
1               5                   10                  15

Ala Gln Gly Val Met Asp Leu Phe Gly Glu Glu Gly Arg Glu His
            20                  25                  30

Arg Arg His His Arg His Ser Leu Leu Pro Pro Tyr Leu His Asn Val
                35                  40                  45

Ser Cys Glu Ala Lys Trp Glu Tyr Phe Lys Ile Val Gly Asn Arg Ser
    50                  55                  60

Leu Thr Phe Ala Glu Lys Arg Lys Glu Ile Ser Glu Trp Ala Lys Lys
65                  70                  75                  80

Tyr Asn Val Val Asp Glu Val Ala Ser Tyr Asn Ala Tyr Arg Glu Lys
                85                  90                  95

Leu Lys Gln Glu His Arg Lys Asn Val Ser Glu Leu Val Ser Ala Leu
            100                 105                 110

Pro Asn Ala Val Lys Lys Val Asn Asp Leu Leu Asp Asn Glu Asn Gln
        115                 120                 125

Thr Pro Arg Gln Leu Tyr Val Ala Leu Arg Lys Leu Gly Arg Gln Asn
    130                 135                 140

Pro Ala Leu Tyr Arg Ile Val Glu Tyr Ile Asn Val Ala Val Arg Leu
145                 150                 155                 160

Arg Ser Glu Glu Val Asp Glu Gln Gln Arg Arg Arg Leu Ser Ala
                165                 170                 175

Leu Pro Phe Gly Asp His Asn Asp Asn Leu Glu Glu Gln Asp Phe Gly
            180                 185                 190

Glu Gln Asp Phe Arg Tyr Val Tyr Gly Phe Glu Cys Ala Arg Phe Leu
        195                 200                 205

Leu Gln Asn Gly Arg Met Phe Gly Leu Asn Thr Asp Glu Arg Tyr
    210                 215                 220

<210> SEQ ID NO 79
<211> LENGTH: 203
<212> TYPE: PRT
<213> ORGANISM: Nippostrongylus brasiliensis

<400> SEQUENCE: 79

Met Lys Ala Leu Leu Ile Ala Val Leu Ala Leu Thr Ala Ala His
1               5                   10                  15

Tyr Arg Gly Lys Glu Ser Glu Thr Gly His Gly Arg His His His
            20                  25                  30

Pro Pro Pro Pro Pro Phe Leu Lys Asp Val Asp Lys Ser Ala Arg Lys
        35                  40                  45

Glu Phe Phe Ala Ile Val Lys Asn Lys Thr Leu Thr Ile Ala Glu Gln
    50                  55                  60

Lys Ala Ala Val Leu Glu Trp Ala Glu Cys His Gly Ile Lys Asp Glu
65                  70                  75                  80

Val Glu Gln Phe Gln Lys Met Ala Ser Leu Gly Asp Glu Ile Lys
                85                  90                  95

Lys Asn Val Ala Glu Leu Ile Ser Lys Leu Pro Ala Ala Phe Gln Ser
            100                 105                 110

Phe Ser Ala Val Met Glu Ser Glu Asn Gln Thr Arg Arg Glu Gln Lys

```
                115                 120                 125
Asp Arg Leu Lys Ala Leu Lys Asp Glu Gln Pro Lys Val Phe Asn Val
            130                 135                 140

Leu Lys Ala Ala Phe His Gln Phe Lys Pro Met Asn Glu Gly Pro Gly
145                 150                 155                 160

Lys Phe Val Gly Gly Arg Arg His Arg Arg Gln Ala Gln Glu Asp Cys
                165                 170                 175

Pro Glu Ala Ile Phe Leu Phe Glu Ile Asp Glu Asn Glu Glu Glu Lys
            180                 185                 190

Pro Thr Pro Lys Pro Lys Arg Arg Asn Arg Phe
                195                 200

<210> SEQ ID NO 80
<211> LENGTH: 212
<212> TYPE: PRT
<213> ORGANISM: Teladorsagia circumcincta

<400> SEQUENCE: 80

Met Lys Leu Leu Leu Ser Ile Phe Leu Val Ala Cys Val Leu Ser
 1               5                  10                  15

Val Asp Gly Trp Asn Arg Val Arg Ala Leu Thr Lys Gly Glu Glu Arg
            20                  25                  30

Thr Thr Asp Asp Glu Ser Asp Ser Asn Cys Cys Pro Cys His His His
        35                  40                  45

Cys His Tyr His His His Lys Met Pro Pro Phe Leu Lys His Val Ser
    50                  55                  60

Ala Asp Ala Arg Trp Glu Tyr Tyr Ala Ile Ile Arg Asp Met Phe Ser
65                  70                  75                  80

Ser Met Ser Glu Lys Leu Lys Lys Leu Asp Glu Trp Ala Lys Lys Gln
                85                  90                  95

Asp Pro Glu Val Lys Lys Gly Met Glu Ala Tyr Phe Lys Asn Ile Asp
            100                 105                 110

Met Tyr Trp Lys Asp Val Asn Lys Asn Met Thr Met Thr Leu Glu Glu
        115                 120                 125

Leu Pro Lys Ile Tyr Pro Lys Val Tyr Glu Ile Met Ala Asp Leu Asp
    130                 135                 140

Leu Thr Pro Arg Glu Ile Tyr Lys Lys Ile Arg Asp Leu Gln Met Ser
145                 150                 155                 160

Lys Met Thr Ser His Ser Leu Tyr Ala Val Ala Met Ala Val Ile His
                165                 170                 175

Thr Gly Gly Ala Glu Tyr Pro Tyr Leu Met Asp Asn Asp Met Phe Phe
            180                 185                 190

Glu Thr Leu Ala Thr Pro Lys Ile Arg Asn Leu Phe Asn Asn Arg Asn
        195                 200                 205

Thr Cys Asn Asn
    210

<210> SEQ ID NO 81
<211> LENGTH: 201
<212> TYPE: PRT
<213> ORGANISM: Ostertagia ostertagi
<220> FEATURE:
<221> NAME/KEY: misc_feature
<222> LOCATION: (4)..(4)
<223> OTHER INFORMATION: Xaa can be any naturally occurring amino acid

<400> SEQUENCE: 81

Lys Ser Ala Xaa Phe Leu Leu Leu Ile Gly Ala Thr Val Leu Gly His
```

```
                1               5                   10                  15
Ala Arg His Asn Glu Gly Cys Pro Arg Glu Ser His Arg Ala Gln
                    20                  25                  30

Pro Arg Pro Lys Phe Leu His His Val Gly Ile Lys Ala Arg Arg Glu
            35                  40                  45

Tyr Phe His Ile Val Arg Ser Gly Glu Ile Ile Ala Lys Gln Asp Glu
        50                  55                  60

Gln Ile Leu Asp Trp Ala Lys Lys Tyr Gly Val Glu Glu Val Glu
65                      70                  75                      80

Glu Phe Asn Asn Lys Thr Ala Ser Tyr Val Glu Glu Leu Val Gln Asn
                    85                  90                  95

Val Thr Asn Leu Ile Ala Glu Leu Pro Thr Ala Leu Glu Ala Phe Leu
                    100                 105                 110

Asn Ile Thr Gln Asn Lys Asp Gln Thr Arg Met Glu Met Lys Lys Ala
                    115                 120                 125

Leu Arg Glu Met Arg Thr Glu Glu Phe Glu Val Phe Asp Ala Leu Lys
        130                 135                 140

Ala Ala Phe Lys Val Phe Lys Pro Asn His Cys Leu Tyr His Arg Cys
145                     150                 155                     160

Thr Asp Ser Gln Ser Ser Glu Glu Leu Val Asp Asp Trp Met Asp Phe
                    165                 170                 175

Gln Glu Lys Asp Asp Gln Ile Ser Lys Met Leu Asp Pro His Asp Glu
                    180                 185                 190

Phe Thr Met Met Gln Lys Ser Gly Val
        195                 200

<210> SEQ ID NO 82
<211> LENGTH: 241
<212> TYPE: PRT
<213> ORGANISM: Caenorhabditis elegans

<400> SEQUENCE: 82

Met Ala Leu Ser Tyr Ser Phe Ile Phe Thr Leu Phe Ala Phe Ser Ala
1               5                   10                  15

Val Val Leu Ala Gly Pro Gly Gly Arg His Gly His Gly Gly Gly
                    20                  25                  30

Phe Gly Gly Ala Pro Gln Leu Pro Pro Phe Leu Gln Asn Val Thr Ala
            35                  40                  45

Glu Gly Arg Gln Ala Phe Phe Ala Ile Val Ser Asn Thr Ser Leu Thr
        50                  55                  60

Ile Ser Glu Thr Glu Ser Gln Ile Ser Ser Trp Ala Gln Thr Tyr Gly
65                  70                  75                      80

Val Ser Ser Gln Val Thr Glu Phe Gln Thr Lys Val Glu Glu Lys Leu
                    85                  90                  95

Asn Glu Ile Lys Gln Asn Val Thr Ala Val Ile Asn Asn Leu Ser Thr
                    100                 105                 110

Val Glu Thr Gln Leu Glu Ala Ile Phe Ala Asn Lys Ser Gln Thr Ile
                    115                 120                 125

Arg Glu Gln Phe Gln Ala Leu Gly Gln Leu Lys Asp Gln Tyr Pro Gln
        130                 135                 140

Glu Val Gly Val Leu Leu Phe Leu Ala Lys Pro Lys Gly Glu His Gly
145                     150                 155                     160

Gly Gln Gly Pro Phe Gly Gly Phe Pro Gly Gly His Gln Gly Gly Phe
                    165                 170                 175

Pro Gly Gly Asn Gln Gly Gly Phe Gly Gly Asn Gln Gly Gly Phe Gly
```

```
                        180                 185                 190
Gly Asn Gln Gly Gly Phe Pro Phe Gly Asn Gln Gly Gly Asn Gln Gly
            195                 200                 205

Gly Phe Pro Phe Gly Asn Pro Gly Asn Gln Gly Gly Phe Gly Gly Asn
    210                 215                 220

Gln Gly Gly Asn Gln Gly Gly Phe Gly Gly Asn Arg Gly Gly Arg Gly
225                 230                 235                 240

Phe

<210> SEQ ID NO 83
<211> LENGTH: 235
<212> TYPE: PRT
<213> ORGANISM: Caenorhabditis elegans

<400> SEQUENCE: 83

Met Ser Tyr Tyr Ser Thr Ser Leu Tyr Ile Phe Ala Ile Thr Met Ala
1               5                   10                  15

Thr Met Val Leu Ala Gly Pro Arg Gly Gly Phe Gly Gly Gly Pro Gly
            20                  25                  30

Gly Pro Gly Gly Arg Gly Arg His Gly Pro Pro Met Pro Pro Phe Leu
        35                  40                  45

Gln Asn Val Thr Asp Glu Gly Arg Arg Ala Phe Phe Asp Ile Ala Arg
    50                  55                  60

Asn Gln Asn Leu Thr Ile Ala Glu Met Glu Ser Gln Thr Ser Thr Trp
65                  70                  75                  80

Ala Gln Thr Tyr Gly Val Ser Asp Val Tyr Ser Glu Phe Glu Ala Asn
            85                  90                  95

Ile Thr Ala His Arg Asn Glu Val Gln Gln Asn Val Thr Gln Val Val
        100                 105                 110

Ser Gln Leu Ser Ala Ala Gln Thr Ala Leu Glu Ala Val Met Asn Asn
    115                 120                 125

Lys Asn Gln Thr Arg Gln Gln Met Lys Glu Ala Ile Asp Asn Leu Lys
130                 135                 140

Thr Gln Tyr Pro Gln Glu Ile Pro Ala Leu Phe Phe Ile Ser Gly Ser
145                 150                 155                 160

Phe Arg Arg Gly Pro Gly Gly Arg His Gly Gly Pro Gly Gly Pro Gly
            165                 170                 175

Gly Arg Arg Met Gly Pro Gly Gly Arg Gly Gly Asp Ser Arg Glu Gly
            180                 185                 190

Pro Met Met Gly Gly Met Gly Arg Gly Gly Phe Gly Gly Gln Gly Met
            195                 200                 205

Gly Gly Met Gly Ala Gly Leu Gly Gln Gly Arg Arg Gly Gly Pro Asp
        210                 215                 220

Ser Met Asn Glu Ser Ser Asp Val Asn Asp Phe
225                 230                 235
```

EQUINE PARASITE DETECTION

CROSS-REFERENCE TO RELATED APPLICATIONS

This application is a U.S. national counterpart application of PCT nternational Application Serial No. PCT/GB2010/000616, filed Mar. 31, 2010, which claims priority to United Kingdom Patent Application Serial Number 0905511.2, filed Mar. 31, 2009, the disclosures of both which are hereby incorporated herein by reference.

FIELD OF THE INVENTION

The present invention provides a means of detecting infections caused by parasitic nematodes belonging to the Cyathostominae group in Equine subjects and in particular in horses.

BACKGROUND OF THE INVENTION

Members of the Cyathostominae group of nematodes infect almost all grazing horses. Most horses have burdens to the order of tens of thousands of cyathostomins and usually do not exhibit clinical disease, however, in some animals, infection leads to a severe inflammatory enteropathy [15]. This disease occurs following accumulation of *cyathostomin* larvae that encyst and undergo inhibited development as early third larvae (EL3) in the large intestinal wall. Vast numbers of encysted larvae can accumulate and these can reactivate simultaneously to cause an inflammatory enteropathy known as larval cyathostominosis. The principal effect of this syndrome is weight loss, but horses can exhibit other signs including diarrhoea, colic, subcutaneous oedema and/or pyrexia [25]. Up to 50% of animals with larval cyathostominosis die as a result of the condition [15]. This disease most commonly occurs in younger horses, however horses have a lifelong susceptibility to infection and disease may occur at any age [15, 35]. Encysted larvae can persist for prolonged periods (up to two years in some cases) and it has been proposed that encystment is favoured by a variety of factors including; negative feedback from mature worms in the large intestinal lumen, a large larval challenge or a 'trickle' infection [29]. *cyathostomin* EL3 have limited susceptibility to several currently available anthelmintics [12, 19] and drug resistance is common, particularly with regard to benzimidazole and pyrantel compounds [17]. Moxidectin is now only drug available that has high efficacy against EL3, but for which resistance is not yet widespread. It is therefore important that the high efficacy of this anthelmintic be maintained for as long as possible.

To reduce the spread of anthelmintic resistance, it is important that only animals with moderate to high *cyathostomin* burdens are targeted strategically for treatment [32]. Targeted treatments can be undertaken on the basis of faecal egg counts however the latter have no value in estimating burdens of mucosal larvae. Indeed, horses with high mucosal burdens often have low or negative faecal egg counts [31] and there is no specific, non-invasive method to diagnose pre-patent *cyathostomin* infection. A diagnostic test for mucosal larvae would allow veterinarians to identify horses that require larvicidal anthelmintic treatments. Recently, we identified two larval antigen complexes (observed to migrate at 20 and 25 kDa by 1-dimensional SDS PAGE) that have diagnostic potential [9-11]. Significant increases in serum IgG(T) specific to these antigen complexes were observed as early as 6 weeks post infection (PI) in experimentally-infected ponies [11]. Antigens present in both complexes appeared to be specific for mucosal larval cyathostomins, indicating their utility as markers of pre-patent infection [11]. When serum IgG(T) levels were compared amongst groups of naturally- and experimentally-infected horses, there was a strong significant correlation of anti-25 kDa serum IgG(T) responses with total mucosal burden, particularly EL3 burden [10]. In naturally infected horses, IgG(T) responses to both larval complexes were significantly greater than those in uninfected individuals [10] and IgG(T) levels to both complexes were significantly higher in larval cyathostominosis clinical cases than in helminth-naïve ponies and parasite-negative horses from an abattoir [10]. These results indicate that an immunoassay based on antigens present in these complexes could ultimately be used to differentially diagnose larval cyathostominosis, or used to target horses with high mucosal burdens for treatment. The native mucosal larval preparations are extremely time-consuming to prepare and rely on a continuous source of infected mucosa. Therefore, it would be advantageous if genes encoding proteins present in these complexes were isolated and cloned and the associated proteins expressed in recombinant form.

SUMMARY OF THE INVENTION

The present invention is based upon the finding that parasitic nematodes belonging to the Cyathostominae group express proteins which can be used to diagnose, detect or identify incidences of *cyathostomin* infection in animals, particularly horses. Although *cyathostomin* infections are treatable, the range of effective drugs is rapidly diminishing and at present only moxidectin exhibits a high efficacy against the encysted *cyathostomin* parasite.

In order to ensure that the development of resistance to moxidectin can be delayed for as long as possible, it is essential that only animals with moderate to high *cyathostomin* burdens are targeted for treatment. However, the encysted larval stages of this parasite can remain undetected for months or even years eventually emerging from the intestinal wall to cause severe pathology (including symptoms of diarrhoea, weight loss, colic, oedema and pyrexia); as such, it is often difficult to know whether or not a particular animal should be treated.

The inventors have identified a number of proteins that are expressed predominantly during the mucosal larval stages (i.e. the early third larval (EL3) and late third (LL3)/developing fourth (DL4) stages). These proteins are highly immunogenic and exhibit low cross-reactivity to proteins present in other helminth species.

Accordingly, a first aspect of this invention provides a method of diagnosing a *cyathostomin* infection, said method comprising the step of identifying a level of anti-*cyathostomin* larval antigen antibodies in a sample, wherein a level of anti-*cyathostomin* larval antigen antibodies is indicative of a *cyathostomin* infection.

Animals positively diagnosed as having a "*cyathostomin* infection" by the method provided by the first aspect of this invention may harbour high numbers of encysted *cyathostomin* in the gut mucosa, particularly the large intestinal wall, as such they may generate a significant immune response to *cyathostomin* antigens including any antigens produced by the EL3, LL3 and DL4 stages. Animals with infections of this type may otherwise be referred to as having high mucosal burdens. In other instances, positive diagnoses may indicate animals with larval cyathostominosis, an inflammatory enteropathy manifesting with symptoms of weight loss, diarrhoea, colic, subcutaneous oedema and/or pyrexia. Conditions of this type are often fatal if untreated.

In one embodiment, "a level" of anti-*cyathostomin* larval antigen antibodies may be evaluated relative to the "a level" of anti-*cyathostomin* larval antigen antibodies present in reference or control samples derived from healthy animals or animals not having high mucosal burdens of *cyathostomin* parasites or larval cyathostominosis. In this way levels and, in particular high levels, of anti-*cyathostomin* larval antigen antibodies, may easily be detected. Accordingly, the term "a level" may be taken to include levels of anti-*cyathostomin* larval antigen antibodies which are less or greater than levels of anti-*cyathostomin* larval antigen antibodies identified in reference or control samples.

It should be understood that in addition to providing methods in which levels of anti-*cyathostomin* larval antigen antibodies are detected in samples, the present invention might also be adapted to provide methods in which levels of *cyathostomin* larval antigens are detected in samples. Methods of this type, rather than "indirectly" diagnosing *cyathostomin* infections via immune responses, may provide a more direct means of diagnosing *cyathostomin* infections. As above, "a level" of *cyathostomin* larval antigens may be taken to include levels of anti-*cyathostomin* larval antigen which are less or greater than levels of anti-*cyathostomin* larval antigen identified in reference or control samples.

The *cyathostomin* larval antigens described/mentioned herein may be derived from larval antigen complexes having a molecular weight of about 20 to about 25 kDa. An exemplary larval antigen is obtained from the parasite *cyathostomin pateratum* and comprises or consists of the following amino acid sequence (designated SEQ ID NO: 1):

```
                                                    SEQ ID NO: 1
MNKTLTFLTVVSAVALAQGVMDLFGEEGREEHRRHHRHSLLPPYLHNVSCEAKWEYF

KIVGNRSLTFAEKRKEISEWAKKYNVVDEVASYNAYREKLKQEHRKNVSELVSALPN

AVKKVNDLLDNENQTPRQLYVALRKLGRQNPALYRIVEYINVAVRLRSEEVDEQEQR

RRLSALPFGDHNDNLEEQDFGEQDFRYVYGFECARFLLQNGRMFGLNTDERY
```

The nucleic acid sequence encoding the protein provided by SEQ ID NO: 1 has also been determined and is given as SEQ ID NO: 2 below.

```
                                                    SEQ ID NO: 2
Atgaacaaaacgttaacatttctcacagtcgttagtgccgtagctctggcccaaggt gtcatggaccttttggtgaagagggtcgtgaagaacatcgtcgtcaccatcgtcat tcacttttaccaccatatctccacaatgtgagctgtgaggctaaatgggagtacttc aaaattgtggggaacaggagtttgacctttgctgagaaaagaaaggaaattagcgag tgggcaaaaaaatacaatgttgtggatgaagttgcaagctacaatgcttacagggaa aaactcaagcaggagcacagaaaaaacgttagcgaacttgtttctgctcttccaaac gcagtgaagaaagtcaatgatcttctagacaatgaaaatcagactcctaggcaactt tacgttgcccttagaaaacttggtagacaaaatccggcactttaccgtattgtcgag tacattaatgtggctgtaagactaagaagtgaagaagtggatgagcaagaacaacga agaaggctgtcagctctaccttttggcgaccataacgataatttggaagagcaggac ttcggtgaacaagactttcgctatgtctatggctttgagtgtgcaagatttctcctt caaaatggaagaatgtttggacttaacacagatgaaagatat
```

One of skill in the art will appreciate that while SEQ ID NO: 1 represents the entire coding sequence of an exemplary *cyathostomin* larval antigen, after removal of the signal peptide the mature antigen may comprise 206 amino acids yielding a protein having a molecular weight of approximately 25.6 kDa.

In addition, the inventors have isolated homologous antigens from other *cyathostomin* spp., and the amino acid sequences of these are provided below as SEQ ID NOS: 3, 5 and 7 respectively. In addition, the nucleic acid sequences encoding each of the proteins encoded by SEQ ID NOS: 3, 5 and 7 have been designated SEQ ID NOS: 4, 6 and 8 respectively and each is detailed below.

```
                                                    SEQ ID NO: 3
HEELRRHHRHSLLPPYLHNVSCEAKWEYFKIVGNRSLTFAEKKGKSSEWAKKYNVVD

EVASYNAYREKLKQEHRKNVSELVSGLPGAVKKVNELLDNENQTPRQLYVALRKLGK

QNPVLYRVVEFVNLVVRFRREDSDEQEQREMLSTLPFSENNEEQDLGEQDFQYIYGF

ECARFIFQNGRMFGLNTDRRY
```

The antigen encoded by SEQ ID NO: 3 was isolated from *Cylicocyclus nassatus*.

SEQ ID NO: 4
Catgaagaacttcgtcgtcaccatcgtcattcacttttaccaccctatctccacaat gtgagctgtgaagccaaatgggaatacttcaagattgtggggaacaggagcttgact tttgctgaaaagaagggaaaaagtagcgagtgggcaaaaaaatacaatgttgtggat gaagttgcaagttacaatgcctatagagaaaaacttaagcaggagcacaggaaaaac gttagcgaacttgtttctggtcttcccggtgctgtgaagaaagtaaacgaactcttg gataatgagaatcagactcctaggcaactttacgttgctctaagaaagcttggtaaa caaaatccagtactctaccgtgttgtcgagtttgtcaatttggttgtgagatttaga cgtgaagattcggatgagcaagaacaacgagaaatgctgtcaactttacctttcagc gaaaataatgaagagcaggaccttggtgaacaagacttccagtacatctatggtttt gaatgtgcaagattcatctttcaaaatgggagaatgtttggactcaacacggataga agatat

SEQ ID NO: 5
SCVAKWEYFKIVINRSLTFAQRKEEISKWAKKYKVEDEVASYNAYREKLKQQHRKNV

SELVSNLPGAVERVNKLLDNENQTPKQLYLALRELGKQNPALYHVVEYVNVVVRLKR

EELDQQDQRRALSGSLFGENNDNLEEQDFGEEDFRYVYGFECARFILQNGRMFGLNM

DRNY

The antigen encoded by SEQ ID NO: 5 was isolated from *Coronocyclus coronatus*.

SEQ ID NO: 6
Agctgtgtggctaagtgggagtacttcaagatcgtgatgaacaggagtctgacgttt gctcaaagaaaggaagaaattagcaagtgggcgaaaaaatacaaagttgaggatgaa gttgcaagctacaatgcttatagagaaaaactcaagcagcagcacaggaaaaacgtt agcgaacttgtttctagtcttcccggtgcaatggaaagagtgaacaaacttttggac aatgaaaaccagacccctaagcaactttaccttgccctacgagaacttggcaaacaa aatccggcactttaccatgttgtcgagtatgtcaatgtggttgtgagacttaaacga gaagaattggatgaacaagatcaatgaagagcgctgtcgggttcacttttttggcgag aataacgacaatctagaagagcaggactttggtgaagaagactttcgctatgtctat gggtttgaatgtgcaagattcatccttcaaaatggaagaatgtttggtctaaacatg gataggaattat

SEQ ID NO: 7
GEEDREEHRRHHRHSLLPPYLHNVSCVAKWEYFRIVGNRSLTFAEKKKEISEWAKKY

NVLDEVASYNAYREKLKQEHRKNVSELVSDLPKAVKKVNDLLDNENQTPRQLYVALR

ELGRQNPTLYRIVEYINVAVRRRSEELDEQEQGRRLSALPFGDNNDNLEEQDFGEQD

FRYVYGFECARFLLQNGRMFGLNTDERD

The antigen encoded by SEQ ID NO: 7 was isolated from *Cyathostomum catinatum*.

SEQ ID NO: 8
Gaggatcgtgaagaacatcgccgtcaccatcgtcattcactcttgccaccatatctc cacaacgtgagctgtgtggccaaatgggaatactttagaattgtggggaacaggagt -continued ttaacgtttgctgagaaaagaaagaaattagcgagtgggcaaaaaaatacaatgtt ctggatgaagtagcaagctacaatgcttatagggaaaaactcaagcaggagcacaga aaaaacgttagcgaacttgtttctgatcttcccaaggcagtaaagaaagtcaacgat cttctagacaatgaaaatcagactcctaggcaactttatgttgcccttagagagctt ggtagacaaaatccgacactttaccgtattgtcgagtacatcaatgtggctgtaagg cgaagaagtgaagaactggatgagcaagaacaaggaagaaggctgtcagctttacct ttcggcgacaacaacgataatttggaagagcaggacttcggtgaacaagactttcgc tatgtctacggctttgagtgtgcaagatttctccttcaaaatggaagaatgttcgga ctcaacacagatgaaagagat SEQ ID NOS 9, 11, 13, 15, 17, 19, 21, 23, 25, 27, 29, 31, 33, and 35 have been translated into amino acid sequences by removing the non-coding regions (introns) identified by comparison with the coding sequence of Gala-1.

The antigen encoded by SEQ ID NO: 9 was isolated from *Cylicocyclus ashworthi*.

```
                                                SEQ ID NO: 9
ATGAACAAAACGTTAACATTTCTCACAGTCGTTAGTGCCGTAGTTCTGGCCCAAGGT

GTCATGGACCTTTTTGGTGAAGAGGGTCGTGAAGAACATCGCCGTCACCATCGTCAT

TCACTCTTACCACCATATCTCCACAACGTGAGCTGTGTGGCTAAATGGGAGTACTTC

AAAATTGTAGGGAACAGGAGTTTAACGTTTGCTGAGAAAAAGAAGAAATTAGCCAG

TGGGCAAAAAAATACAATGTTGTGGTAAGCTTTTCTGAATTAATGTAAATACACTCG

CATGCTGGCCTTTTTAGGATGAAGTTGCAAGCTACAATGCTTACAGGGAGAAACTCA

AGCAGGAGCACAGAAAAAACGTTAGCGAACTTGTTTCTGCTCTTCCAAACGCAGTAA

AGAAAGTCAACAATCTTCTAGACAATGAAAATCAGACTCTTAGGCAACTTTACGTTG

CCCTTAGAGAACTTGGTAGACAAAATCCGGCAGTAAGTAGAAAGAGCTGCACTCCTG

GGCTTAATAAAACAAATTATTTAAGCTTTACCGTATTGTCGAGTACATCAATGTGGC

TGTAAGACGAAGAAGTGAAGGACTGGATGAGCAAGAACAACGAAGAAAGCTATCAGC

TTTACCTTTCGGCGACAACAACGATAATATGGAAGAGCAGGACTTCGGTGAACAAGA

CTTTCGCTATGTCTACGGCTTTGAGTGTGCAAGATTTCTCCTTCAAAATGGAAGAAT

GTTTGGGCTCAACACAGATGAAAGAGATTAGCAAAGAATCAATTGTAGTTCAAAGCG

GTAGAGTTTGAGCTGCAAACTCAGCATGCCATCATCACCTCCT
```

```
                    SEQ ID NO: 10 (i.e., SEQ ID NO: 9 translated)
MNKTLTFLTVVSAVVLAQGVMDLFGEEGREEHRRHHRHSLLPPYLHNVSCVAKWEYF

KIVGNRSLTFAEKKEEISQWAKKYNVVDEVASYNAYREKLKQEHRKNVSELVSALPN

AVKKVNNLLDNENQTLRQLYVALRELGRQNPALYRIVEYINVAVRRRSEGLDEQEQR

RKLSALPFGDNNDNMEEQDFGEQDFRYVYGFECARFLLQNGRMFGLNTDERD
```

The antigen encoded by SEQ ID NO: 11 was isolated from *Cyathostomum catinatum*.

```
                                               SEQ ID NO: 11
ATGAACAAAACGTTAACATTTCTCACAGTCGTTAGTGCCGTAGTCCTGGCT

CAAGGTGTCATGGACCTTTTTGGTGAAGAAGGCCGTGAAGAACATCGCCG

TCACCGTCGTCATTCACTCTTGCCACCATATCTCCACAACGTGAGCTGTGT
```

-continued

```
GGCTAAATGGAATACTTCAGAATTGTGGGGAACAGGAGTTTGACGTTTG

CTGAGAAAAAGGAAGAGATTAGCGAGTGGGCAAAAAAGTACAATGTTGT

GGTAAGCTTTTCTGAATTGATGTAAATACACTCGCATGCTGGCCTTTTTAG

GATGAAGTTGCAAGCTACAATGCTTACAGGGAAAAACTCAAGCAGGAGC

ACAGAAAAAACGTTAGCGAACTTGTTTCTGCTCTTCCAAACGCAGTAAAG

AAAGTCAACGATCTTCTAGACAATGAAAATCAGACTCCTAGGCAACTTTA

CGTTGCCCTTAGAGAACTTGGTAGACAAAATCCGGCAGTAAGTCGAAAGA

GCTGCACTCTTGGGCATAAGTAAAAAAAGTATTTTAGCTTTACCGTATTG

TGGAGTACATCAATGTGGCTGTAAGACTAAGAAGTGAAGAAGTGGATGA

GCAAGAACAACGAAGAAGGCTATCAGCTTTACCTTTTGGTGACCATAACG

ATAATATGGAAGAGCAGGACTTTGGTGATCAAGACTTTCGCTATGTCTAC

GGCTTTGAGTGTGCAAGATTTCTCCTTCAAAATGGAAGAATGTTTGGACTT

AACACAGATGAAAGATATTAGTAAAAATTAACTGTAGCTCAAAGCGGTAG

AGTTTGAGCTGCAAACTCAGCATGCCATCATCACCTCCT
```

```
                      SEQ ID NO: 12 (i.e., SEQ ID NO: 11 translated)
MNKTLTFLTVVSAVVLAQGVMDLFGEEGREEHRRHRRHSLLPPYLHNVSCVAKWEYF

RIVGNRSLTFAEKKEEISEWAKKYNVVDEVASYNAYREKLKQEHRKNVSELVSALPN

AVKKVNDLLDNENQTPRQLYVALRELGRQNPALYRIVEYINVAVRLRSEEVDEQEQR

RRLSALPFGDHNDNMEEQDFGDQDFRYVYGFECARFLLQNGRMFGLNTDERY
```

The antigen encoded by SEQ ID NO: 13 was isolated from *Cylicostephanus goldi*.

```
                                                    SEQ ID NO: 13
ATGAACAAAACGTTAACATTTCTCACAGTCGTTAGTGCCGTAGTCCTGGCTCAAGGT

GTCGTGGACCTTTTTGGTGAAGAGGGTCGTGAAGAACATCGCCGTCACCATCGTCAT

TCACTCTTACCACCATATCTCCACAACGTCAGCTGTGTGGCTAAATGGAATACTTC

AAAATTGTGGGGAATAGGAGTTTGACATTTGCTGAGAAAAAGAAAGAAATTAGCGAG

TGGGCTAAAAAATACAATGTAGTGGTAAGCTTTTTTGACTTGATGTAAATGCACTCG

TATGCCGGCCCTTTTAGGATGAAGTTGCAAGGTACAATGCTTATAGAGAAAAACTTA

AGCAGGAACACAGGAAAAACGTCAGCGAACTTGTTTCTGATCTTCCCAACGCAGTAA

AGAAAGTGAATGATCTCCTGGACAATGAGAATCAAACTCCTAGGCAACTTTACATTG

CCCTCAGAGAACTTGGTAGACAAAATCCAGAAGTAAGTTGAAAGTGCTGCAATTTTA

GGCTTAGATAAAACAGTTGTTTAAGCTTTACCGTGTTGTCGAGTTTATCAATGTGGC

TGTAAGAATAAGACGTGAAGATTTGGATGAGCAAGAACAACGAACAAGGCTGTCAAC

TTTACCTTTTGGCGACAACAACGACAATTTCGAAGAGCAAGACTTCGGTGAACAAGA

CTTTCGCTATGTCTATGGCTTTGAGTGTGCAAGATTTCTCCTTCAAAATGGAAGAAT

GTTTGGACTTAACACGGATAGAAGATAC
```

```
                      SEQ ID NO: 14 (i.e., SEQ ID NO: 13 translated)
MNKTLTFLTVVSAVVLAQGVVDLFGEEGREEHRRHHRHSLLPPYLHNVSCVAKWEYF

KIVGNRSLTFAEKKKEISEWAKKYNVVDEVARYNAYREKLKQEHRKNVSELVSDLPN

AVKKVNDLLDNENQTPRQLYIALRELGRQNPELYRVVEFINVAVRIRREDLDEQEQR

TRLSTLPFGDNNDNFEEQDFGEQDFRYVYGFECARFLLQNGRMFGLNTDRRY
```

The antigen encoded by SEQ ID NO: 15 was isolated from *Cylicostephanus goldi*

SEQ ID NO: 15
ATGAACAAAACGTTAACATTTCTCACAGTCGTTAGTGCCGTAGTCC
TGGCCCAAGGTGTCATGGACCTTCTTGATGAAGAGGCTCGTGGAGA
GCATCGCCGTCACCATCGTCATTCACTCTTACCACCATATCTCCAC
AACGTGAGCTGTGTGGCTAAATGGGAATACTTCAAAATTGTGGGGA
ACAGGAGTTTGACGTTTGCTGAGAAAAAGAAAGAAATTAGCGAGTG
GGCAAAAAAATACAACGTTGTGGTAAGCTTTTGTGACTCGATGTAG
ATACCCCAGATATTCTAGATACCCATGCTGGCCTTTTTAGGATGAA
GTTGCAAGCTACAATGCTTATAGAGAAAAACTCAAGCAGGAACACA
GGAAAAACGTTAGCGAACTTGTATCTGATCTTCCCAATGCAGTGAA
GAAAGTGAATGATCTCCTGGACAATGAGAATCAAACTCCTAGGCAA
CTTTACGTTGCCCTCAGAGAACTTGGTAGACAAAATCCAGCAGTAA
GTTGAAAGTGCTGCAATTTCAGGCTTAGATAAAACAGTTGTTTAAG
CTTTACCGTGTTGTCGAGCTCATCAATGTGGCTGTAAGATTAAGAC
GTGAAGATTTGGATGAGCAAGAACAACGAACAAGGCTGTCAACCTT
ACCTTTTGGCGACAACAACAACAATTTCGATGAGCAGGACTTCGGT
GAACAAGACTTTCGCTATGTCTATGGCTTTGAGTGTGCAAGATTTC
TCCTTCAAAATGGAAGAATGTTTGGACTTAACACGGATAGAAGATA
CTAGTAAGAGTCAACTGTAGCTCAAAGTGGTTCGAGCTACGAACAG
CATGCCATCATCACCTCCT

SEQ ID NO: 16 (i.e., SEQ ID NO: 15 translated)
MNKTLTFLTVVSAVVLAQGVMDLLDEEARGEHRRHHRHSLLPPYLH
NVSCVAKWEYFKIVGNRSLTFAEKKKEISEWAKKYNVVDEVASYNA
YREKLKQEHRKNVSELVSDLPNAVKKVNDLLDNENQTPRQLYVALR
ELGRQNPALYRVVELINVAVRLRREDLDEQEQRTRLSTLPFGDNNN
NFDEQDFGEQDFRYVYGFECARFLLQNGRMFGLNTDRRY The antigen encoded by SEQ ID NO: 17 was isolated from *Cylicostephanus goldi*

SEQ ID NO: 17
ATGAACAAAACGTTAACATTTCTCACAGTCGTTAGTGCCGTTGTCC
TGGCGCAAGGTGTCATGGCCCTATTTGGTGAAGAGAGTCGTGAAGA
ACACCGCCGTCACCATCGTCATTCACTCTTACCACCATATCTCCAC
AACGTGAGCTGTGTGGCTAAATGGGAGTACTTCAAAATTGTGGGGA
ACAGGAGTTTGACGTTTGCTGAGAAAAAGAAAGAAATCAGCGAGTG
GGCTAAAAAATACAATGTTGTGGTAAGCTTTTTTGACTTGATGTAA
ATGCACTCGCATGCCGGCTTTATAGGATGAAGTTGCAACTGATAA
TGCTTATAGAGAAAAACTCAAGCAGGAACACAGGAAAAACGTTAGC
GAACTTGTTTCTGATCTTCCCAACGCAGTAAAGAAAGTCAGCGATC
TTTTGGACAACGAAATCAGACTTCTAGGCAACTTTATGTTGCACT
CAGAGAACTTGGTAGACAAAATCCGGCAGTAAGTTGAAGAGGCTCC
AATTTTGGGCTCAAGCAAAAATAATTTATTTTAGCTATACCGTGTCG
TCGAGTATATCAATGTGGCTGTGAGATTAAGACGAAAGAACAGGA
TGAACAAGAACGACAAGGAACGCTGTCAGCTCTACCTTTTGGCGAG
AATAACGACAATTTGGAAGAGCAGGACTTTGGTGAACAAGACTTTC
GCTATGTCTATGGCTTTGAGTGTGCAAGATTTCTCCTTCAAAATGG
AAGAATGTTTGGACTCAACACGGATAGAAGATACCAGTAAGAGTCA
ACTGTAGCTCAAAGTGGGTTTGAGCTACGAACAGCATGCCATCATC
ACCTCCT

SEQ ID NO: 18 (i.e., SEQ ID NO: 17 translated)
MNKTLTFLTVVSAVVLAQGVMALFGEESREEHRRHHRHSLLPPYLH
NVSCVAKWEYFKIVGNRSLTFAEKKKEISEWAKKYNVVDEVASYNA
YREKLKQEHRKNVSELVSDLPNAVKKVSDLLDNENQTSRQLYVALR
ELGRQNPAVYRVVEYINVAVRLRRKEQDEQERQGTLSALPFGENND
NLEEQDFGEQDFRYVYGFECARFLLQNGRMFGLNTDRRY The antigen encoded by SEQ ID NO: 19 was isolated from *Cylicostephanus longibursatus*

SEQ ID NO: 19
ATGAACAAAACGTTAACATTTCTCACCGTCGTCTATGCCGTAGTCC
TGGCCCAAGGTGTCATGGACCTTTTTGGTGAAGAGGGTCGTGAAGA
ACATCGCCGTCACCATCGTCATTCACTCTTACCACCATATCTCCAC
AATGTGAGCTGTGTGGCTAAATGGGAATACTTCAAAATTGTGGGGA
ACAGGAGTTTGACGTTTGCTGAGAAAAAGGAAGAAATTAGCAAGTG
GGCAAAAAAATACAATGTTGTGGTACGCTTTTGTAACCCGTATAA
TATACTCTCGCATACTGGCCGTTTCAGGATGAAGTTGCAAGCTACA
GTGCTTGCAGGGAAAAGCTTAAGCAGGAACACAGGAAAAACGTTAG
CGAAATTGTTTCTAATCTTCCCAATGCAGTGAAGAAAGTAAACGAT
CTTTTGGACAATGAAAATCAGACCCCCAGGCAACTTTACGTTGCCT
TCAGAAAACTTGGTAAACAAAATCCGGCAGTAAGTTGAAAGAGCTG
CAATTTTGGGTTGAGGAAAAAAAACTATTTTAGCTTTATCGTGTT
GTCGAGTATATCAATGTGCTTGTGAGACTAAGACGTGAAGAATTTG
ATGAAGATCAGCGAAGATCGCTGTCAGCTTTACCTTTTGGCGACAA
TAACGACGATTTGGAAGAGCAGGACTTTGGTGAACAGGACTTTCGC
TATATCTATGGCTTTGAGTGTGCAAGATTTATCCTTCAAAATGGAA
GAATGTTTCGGACTCAACACGGATAGAAGATATTAGTAAGAGTCAAC
TGTAGCTCGAGGGTTTGAGCTACGAACTGCATGCCATCATCACCTC
CT

SEQ ID NO: 20 (i.e., SEQ ID NO: 19 translated)
MNKTLTFLTVVYAVVLAQGVMDLFGEEGREEHRRHHRHSLLPPYLH
NVSCVAKWEYFKIVGNRSLTFAEKKEEISKWAKKYNVVDEVASYSA
CREKLKQEHRKNVSEIVSNLPNAVKKVNDLLDNENQTPRQLYVAFR
KLGKQNPALYRVVEYINVLVRLRREEFDEDQRRSLSALPFGDNNDD
LEEQDFGEQDFRYIYGFECARFILQNGRMFGLNTDRRY The antigen encoded by SEQ ID NO: 21 was isolated from *Cylicocyclus insigne*.

SEQ ID NO: 21
ATGAACAAAACGTTAACATTTCTCACCGTCGTCTGTGCCGTAGTCC
TGGCCCAAGGTGTCATGGACCTTTTTGGTGAAGAAGGTCGTGAAGA
ACATCGCCGTCACCATCGTCATTCACTCTTACCACCATATCTCCAC
AATGTGAGCTGTGTGGCTAAATGGGAATACTTCAAAATTCTGGGGA
ACAGAAGTTTGACGTTTGCTGAGAAAAAGGAAAAAATCAGCGAGTG
GGCAAAAAAGTACAATGTTGTGGTACGCTTTTGTAACTCCGTATAA
TATACCCTCGCATGCTGGCCGTTTCAGGATGAAGTTGCAAGCTACA
ATGCTTGCAGGGAAAAGCTTAAGCAGGAACACAGGAAAAACGTTAG
CGAAATTGTTTCTAATCTTCCCAATGCAGTAAAGAAAGTAAACGAT
CTTTTGGACAATGAAAATCAGACTCCCAGGCAACTTTACGTTGCCC
TCAGAAAACTCGGTAAACAAAATCCGCCAGTAAGTTGAAAGACTGC
AACTTTGGGTTTAAGGGAAAAAAACTATTTTAGCTTTACCGCGTTG
TCGAGTATATCAATGTGGTTGTGAGACTAAGACGTGAAGAATCTGA
TGAAGACAACGAAGACGCTGTCAGCTTTACCTTTTGGCGACAAT
AACGACAACTTGGAAGAGCAAGACTTTGGTGAAGAAGACTTTCGCT
ATATTTATGGCTTTGAGTGTGCAAGATTTATCCTTCAAAATGGGAG
AATGTTCGGACTCAACACGGATAGAAGATATCAGTAAGAGTCAACT
GTAGCTTAAAAGTTTGAGCTACGAACAGCATGCCATCATCACCTCC
T

SEQ ID NO: 22 (i.e., SEQ ID NO: 21 translated)
MNKTLTFLTVVCAVVLAQGVMDLFGEEGREEHRRHHRHSLLPPYLH
NVSCVAKWEYFKILGNRSLTFAEKKEKISEWAKKYNVVDEVASYNA
CREKLKQEHRKNVSEIVSNLPNAVKKVNDLLDNENQTPRQLYVALR
KLGKQNPLYRVVEYINVVRLRREESDEEQRRTLSALPFGDNNDN
LEEQDFGEEDFRYIYGFECARFILQNGRMFGLNTDRRY The antigen encoded by SEQ ID NO: 23 was isolated from *Cylicostephanus longibursatus*.

SEQ ID NO: 23
ATGAACAAAACGTTAACATTTCTCACCGTCGTCTATGCCGTAGTCC
TGGCCCAAGGTGTCATGGACCTTTTTGGTGAAGAGGGTCTTGAAGA
ACATCGCCGTCACCATCGTCATTCACTCTTACCACCATATCTCCAC
AATGTGAGCTGTGTGGCTAAATGGGAATACTTCAAAATTCTGGGGA
ACAGGAGTTTGACGTTTGCTGAGAAAAAGGAAAAAATCAGCGAGTG
GGCAAAAAAGTACAATGTTGTGGTACGCTTTTGTAACTCAGTATAA
TATATCCTCGCATACTGGCCGTTTCAGGATGAAGTTGCAAGCTACA
ATGCTTGCAGGGAAAAGCTTAAGCAGGAACACAGGAAAAACGTTAG
CGAAATTGTTTCTAATCTTCCCAATGCAGTGAAGAAAGTAAACGAT
CTTTTGGACAATGAAAATCAGACCCCCAGGCAACTTTACGTTGCCC
TCAGAAAACTTGGTAAACAAAATCCGGCAGTAAGTTGAAAGAGCTG
CAATTTTGGGTTTGAGGAAAAAAAACTATTTTAGCTTTATCGTGTT
GTCGAGTATATCAATGTGCTTGTGAGACTAAGACGTGAAGAATTTG
ATGAAGATCAGCGAAGATCGCTGTCAGCTTTACCTTTTGGCGACAA
TAACGACGATTTGGAAGAGCAGGACTTTGGTGAACAGGACTTTCGC
TATATCTATGGCTTTGAGTGTGCAAGATTTATCCTTCAAAATGGAA
GAATGTTCGGACTCAACACGGATAGAAGATATTAGTAAGAGTCAAC
TGTAGCTCAAGGGTTTGAGCTACGAACTGCATGCCATCATCACCTC
CT

SEQ ID NO: 24 (i.e., SEQ ID NO: 23 translated)
MNKTLTFLTVVYAVVLAQGVMDLFGEEGLEEHRRHHRHSLLPPYLH
NVSCVAKWEYFKILGNRSLTFAEKKEKISEWAKKYNVVDEVASYNA
CREKLKQEHRKNVSEIVSNLPNAVKKVNDLLDNENQTPRQLYVALR
KLGKQNPALYRVVEYINVLVRLRREEFDEDQRRSLSALPFGDNNDD
LEEQDFGEQDFRYIYGFECARFILQNGRMFGLNTDRRY The antigen encoded by SEQ ID NO: 25 was isolated from *Cylicocyclus nassatus*.

SEQ ID NO: 25
ATGAACAAAACGTTAACATTTCTCATCGTCGTTAGTGCCGTAGTCC
TGACCCAAAGTGTTATGGACTTTTTCGATGAAGACGGTCGTGAAGA
ACATCGCCGTCATCATCGTCATTCCCTTTTACCACCGTATCTCCAC
AATATGAGCTGCGTGGCCAAATGGGAATACTTCGAGATTGTGGGGG
ACAGGAGTCTGACGTTTGCTGAAAAGAAGGAAAAAATCGGCGAGTG
GGCTAAAAAATACAATGTTGTGGTAAGATTTTGTAACTCTATGTAA
AGATACCCCCGTACGTCGCCCTGTTTAGGATGAAGTTGCAAGCTAC
AATGCTTATAGAGAAAAACTAAAGCAGGAGCACAGGAAAAACGTTA
GCGAGCTTGTCTCTGGTCTTCCCAATGCTGTGAAGAAAATAAACGA
ACTTTTAGACAATGAAAATCAGACTGTTAGGCAACTTTATGTTGCT
TTAAGAGAACTTGGTAAACAAAATCCAGCAGTAAGTTAAAAGAAGT
GCAATTTTGGGCTTAACTAATGAGACAATTTTAGCTCTACCGTGTT
GTCGAGTATATCAATGTGGTTGTGAGACTTAGACGTGAAGATTTGG
ATGAGCAGGAACAACAGAGAACGCTGTCAACCCCACCTTTCGGCGA
GAATAACGAAGAGCAAGACTTTGGTGAACAAGACTTTCACTATATC
TATGGTTTTGAGTGTGCCAGATTCATCCTTCAAAATGGAAGAATGT
TTGGACTTAACACGGATAGAAGATATTAGTAAGAGTTAACTGCAGC
TCAATGTGATAGAGATTGAGCCACAACCCAACATGCCATCATCACC
TCCT

SEQ ID NO: 26 (i.e., SEQ ID NO: 25 translated)
MNKTLTFLIVVSAVVLTQSVMDFFDEDGREEHRRHHRHSLLPPYLH
NMSCVAKWEYFEIVGDRSLTFAEKKEKIGEWAKKYNVVDEVASYNA
YREKLKQEHRKNVSELVSGLPNAVKKINELLDNENQTVRQLYVALR
ELGKQNPALYRVVEYINVVVRLRREDLDEQEQQRTLSTPPFGENNE
EQDFGEQDFHYIYGFECARFILQNGRMFGLNTDRRY The antigen encoded by SEQ ID NO: 27 was isolated from *Cylicocyclus nassatus*.

SEQ ID NO: 27
ATGAACAAAACGTTAACATTTCTCATCGTCGTTAGTGCCATAGTCC
TGGCCCAAAGTGTTATGGACTTTTTCGATGAAGAAGGTCGTGAGGG
ACATCGCCGTCATCATCGTCATTCACTTTTTACCACCATATCTCCAC
AATATGAGCTGCGTGGCCAAATGGGAATACTTCGAGATTGTGGGGG
ACAGGAGTCTGACGTTTGCTGAAAAGAAGGAAAAAATCGGCGAGTG
GGCTAAAAAATACAATGTTGTGGTAAGATTTTGTAACTCCATGTTA
GGATACCTCCGCACGTCGCCCTGTTTAGGATGAAGTTGCAAGCTAC
AATGCTTATAGAGAAAAACTAAAGCAGGAGCACAGGAAAAACGTTA
GCGAGCTTGTCTCTGGTCTTCCCAATGCTGTGAAGAAAGTAAACGA
ACTTTTAGACAATGAAAATCAGACTGTTAGGCAACTTTATGTTGCT
TTAAGAGAACTTGGTAAACAAAATCCAGCAGTAAGTTAAAAGAAGT
ACAATTTTGAGCTCAACTAATGAGACAATTTTAGCTCTACCGTGTT
GTCGAGTATATCAATGTGGTTGTGAGACTTAGACGTGAAGATTCGG
ATGAGCAGGAACAACGAAGAACTCTGTCAACCTCACCTTTCGGCGA
GAATAACGAAGAGCAAGATTTTGGTGAACAAGATTTTCACTATATC
TATGGTTTTGAGTGTGCAAGATTCATCCTTCAAAATGGAAGAATGT
TTGGACTCAATACGGATAGAAGATAT

SEQ ID NO: 28 (i.e., SEQ ID NO: 27 translated)
MNKTLTFLIVVSAIVLAQSVMDFFDEEGREGHRRHHRHSLLPPYLH
NMSCVAKWEYFEIVGDRSLTFAEKKEKIGEWAKKYNVVDEVASYNA
YREKLKQEHRKNVSELVSGLPNAVKKVNELLDNENQTVRQLYVALR
ELGKQNPALYRVVEYINVVVRLRREDSDEQEQRRTLSTSPFGENNE
EQDFGEQDFHYIYGFECARFILQNGRMFGLNTDRRY The antigen encoded by SEQ ID NO: 29 was isolated from *Cylicocyclus nassatus*.

SEQ ID NO: 29
ATGAACAAAACGTTAACATTTCTCATCGCCGTTAGTGCCATAGTCC
TGGCCCAAAGTATGGACTTTTTCGATGAAGACGGTCGTGAAGAACA
TCGCCGTCATCATCGTCATTCACTTTTACCACCATATCTCCACAAT
ATGAGCTGCGCGGCCAAATGGGAATACTTCGAGATTGTAGGGGACA
GGAGTCTGACGTTTGCTGAAAAGAAGGAAAAAATCGGCGAGTGGGC
TAAAAAATACAATGTTGTGGTAAGATTTTGTAACTCCATGTAAAGA
TACCCCTCCATGTCGTCCCGTTTAGGATGAAGTTGCAAGCTACAAT
GCTTGCAGAGAAAAACTGAAGCAAGAGCACAGGAAAAACGTCAGCG
AGCTTGTCTCTGGTCTTCCCAATGCTGTGAAGAAGTAAACGAACT
TTTAGACAATGAAAATCAGACTGTTAGGCAACTTTATGTTGCTTTA
AGAGAACTTGGTAAACAAATCCAGCAGTAAGTTGAAAGAAGTGCA
TTTTGGGCTTAACTAACGAGACAATTTTAGCTCTACCGTGTTGTCG
AGTATATCAATGTGGCTGTGAGACTTAGACGTGAAGATTCGGATGA
GCAGGAAAAACGAAGAACGCTGTCAACCTCACCTTTCGGCGAGAAT
AACGAAGAGCAGGACCTTGGTGAACAAGATTTTCACTATATCTATG
GCTTTGAGTGTGCAAGATTCATCCTTCAAAATGGAAGAATGTTTGG
ACTTAACACGGATAGAAGATATTAGTAAAATTTGACTGCAGCTCAA
AGTGGTAGAGATTGAGCTACCAACCCAACATGCCATCATCACCTCC
T

SEQ ID NO: 30 (i.e., SEQ ID NO: 29 translated)
MNKTLTFLIAVSAIVLAQSMDFFDEDGREEHRRHHRHSLLPPYLHN
MSCAAKWEYFEIVGDRSLTFAEKKEKIGEWAKKYNVVDEVASYNAC
REKLKQEHRKNVSELVSGLPNAVKKVNELLDNENQTVRQLYVALRE
LGKQNPALYRVVEYINVAVRLRREDSDEQEKRRTLSTSPFGENNEE
QDLGEQDFHYIYGFECARFILQNGRMFGLNTDRRY The antigen encoded by SEQ ID NO: 31 was isolated from *Cyathostomum pateratum*.

SEQ ID NO: 31
ATGAACAAAACGTTAACATTTCTCACAGTCGTTAGTGCCGTAGTTCT
GGCCCAAGGTGTCATGGACCTTTTTGGTGAAGAGGGTCGTGAAGAAC
ATCGTCGTCACCATCGTCATTCACTCTTACCACCATATCTCCACAAT
GTGAGCTGTGAGGCTAAATGGGAGTACTTCAAAATTGTGGGGAACAG
GAGTTTGACGTTTGCTGAGAAAAAGGAGAAAATTAGCGAGTGGGCAA
AAAAATACAATGTTGTGGTAAGCTTTTTTGAATTGATGTAAATTCAC
TCGCATGCTGGCCTTTTTAGGATGAAGTTGCAAGCTACAATGCTTAC
AGGGAAAAACTCAAGCAGGAGCACAGAAAAAACGTTAGCGAACTTGT
TTCTGCTCTTCCAAACGCAGTAAAGAAAGTCAACGATCTTCTAGACA
ATGAAAATCAGACTCTTAGGCAACTTTACGTTGCCCTTAGAAAACTT
GGTAGACAAAATCCGGCAGTAAGTCGAAAGAGCTGCGTCCTTGGACT
TAAGCGGAAAAATTATTTCAGCTTTACCGTATTGTCGAGTACATTAA
TGTGGCTGTAAGACTAAGAAGTGAAGAAGTGGATGAGCAAGAACAAC
GAAGAAGGCTGTCAGCTCTACCTTTTGGCGACCATAACGATAATTTG
GAAGAGCAGGACTTCGGTGAACAAGACTTTCGCTATGTCTATGGCTT
TGAGTGTGCAAGATTTCTCCTTCAAAATGGAAGAATGTTCGGACTCA
ACACGGATGGAAGATATTAGTAAGAAACAAGTGTAGCTCAAAGTGGT
AGAGTTTGAGCTACGAACTCAACATGCCATCATCACCTCCT

SEQ ID NO: 32 (i.e., SEQ ID NO: 31 translated)
MNKTLTFLTVVSAVVLAQGVMDLFGEEGREEHRRHHRHSLLPPYLHN
VSCEAKWEYFKIVGNRSLTFAEKKEKISEWAKKYNVVDEVASYNAYR
EKLKQEHRKNVSELVSALPNAVKKVNDLLDNENQTLRQLYVALRKLG
RQNPALYRIVEYINVAVRLRSEEVDEQEQRRRLSALPFGDHNDNLEE
QDFGEQDFRYVYGFECARFLLQNGRMFGLNTDGRY The following sequences (SEQ ID NOS: 33 and 35) represent *Cyathostomin* GALA sequences obtained from cDNA clones.

The antigen encoded by SEQ ID NO: 33 was isolated from *Cylicostephanus goldi*.

SEQ ID NO: 33
ATGAACAAAACGTTAACATTTCTCACAGTCGTTAGTGCCGTTGTCCT
GGCCCAAGGTGTCATGGCCCTATTTGGTGAAGAGAGTCGTGAAGAAC
ACCGCCGTCACCATCGTCATTCACTCTTACCACCATATCTCCACAAC
GTGAGCTGTGTGGCTAAATGGGAGTACTTCAAAATTGTGGGGAACAG
GAGTTTGACGTTTGCTGAGAAAAAGAAAGAAATCAGCGAGTGGGCTA
AAAAATACAATGTTGTGGATGAAGTTGCAAGCTACAATGCTTATAGA
GAAAAACTCAAGCAGGAACACAGGAAAAACGTTAGCGAACTTGTTTC
TGATCTTCCCAACGCAGTAAAGAAAGTCAACGATCTTTTGGACAACG
AAAATCAGACTTCTAGGCAACTTTATGTTGCACTCAGAGAACTTGGT
AGACAAAATCCGGCACTATACCGTGTCGTCGAGTATATCAATGTGGC
TGTGAGATTAAGACGAAAAGAACAGGATGAACAAGACGACAAGGAA
CGCTGTCAGCTCTACCTTTTGGCGAGAATAACGACAATTTGGAAGAG
CAGGACTTTGGTGAACAAGACTTTCGCTATGTCTATGGCTTTGAGTG
TGCAAGATTTCTCCTTCAAAATGGAAGATGTTTGGACTCAACACGG
ATAGAAGATACCAGTAAGAGTCAACTGTAGCTCAAAGTGGGTTTGAG
CTACGAACAGCATGCCATCATCACCTCCT

SEQ ID NO: 34 (i.e., SEQ ID NO: 33 translated)
MNKTLTFLTVVSAVVLAQGVMALFGEESREEHRRHHRHSLLPPYLHN
VSCVAKWEYFKIVGNRSLTFAEKKKEISEWAKKYNVVDEVASYNAYR
EKLKQEHRKNVSELVSDLPNAVKKVNDLLDNENQTSRQLYVALRELG
RQNPALYRVVEYINVAVRLRRKEQDEQERQGTLSALPFGENNDNLEE
QDFGEQDFRYVYGFECARFLLQNGRMFGLNTDRRY The antigen encoded by SEQ ID NO: 35 was isolated from *Cylicostephanus longibursatus*.

SEQ ID NO: 35
C.lon91-GALA
ATGAACAAAACGTTAACATTTCTCACCGTCGTCTATGCCGTAGTCCT
GGCCCAAGGTGTCATGGACCTTTTTGGTGAAGAGGGTCGTGAAGAAC
ATCGCCGTCACCATCGTCATTCACTCTTACCACCATATCTCCACAAT
GTGAGCTGTGTGGCTAAATGGGAATACTTCAAAATTCTGGGGAACAG
GAGTTTGACGTTTGCTGAGAAAAAGGAAAAAATCAGCGAGTGGGCAA
AGAAGTACAATGTTGTGGATGAAGTTGCAAGCTATAATGCTTGCAGG
GAAAAGCTTAAGCAGGAACACAGGAAAAACGTTAGCGAAATTGTTTC
TAATCTTCCCAATGCAGTGAAGAAAGTAAACGATCTTTTGGACAATG
AAAATCAGACCCCCAGGCAACTTTACGTTGCCCTCAGAAAACTTGGT
AAACAAAATCCGGCACTTTATCGTGTTGTCGAGTATATCAATGTGCT
TGTGAGACTAAGACGTGAAGAATTTGATGAAGATCAACGAAGATCGC
TGTCAGCTTTACCTTTTGGCGACAATAACGACGATTTGGAAGAGCAG
GACTTTGGTGAACAGGACTTTCGCTATATCTATGGCTTTGAGTGTGC
AAGATTTATCCTTCAAAATGGAAGAATGTTCGGAATCAACACGGATA
GAAGATATTAGTAAGAGTCAACTGTAGCTCAAGGGTTTGAGCTACGA
ACTGCATGCCATCATCACCTCCT SEQ ID NO: 36 (i.e., SEQ ID NO: 35 translated)
MNKTLTFLTVVYAVVLAQGVMDLFGEEGREEHRRHHRHSLLPPYLHN
VSCVAKWEYFKILGNRSLTFAEKKEKISEWAKKYNVVDEVASYNACR
EKLKQEHRKNVSEIVSNLPNAVKKVNDLLDNENQTPRQLYVALRKLG
KQNPALYRVVEYINVLVRLRREEFDEDQRRSLSALPFGDNNDDLEEQ
DFGEQDFRYIYGFECARFILQNGRMFGINTDRRY Each of the proteins provided by SEQ ID NO: 1, 3, 5, 7, 10, 12, 14, 16, 18, 20, 22, 24, 26, 28, 30, 32, 34, and 36 (or encoded by the nucleic acid sequences of SEQ ID NOS: 2, 4, 6, 8, 9, 11, 13, 15, 17, 19, 21, 23, 25, 27, 29, 31, 33, and 35) may be classified as a member of the "keratin-like" proteins although, because they lack the glycine-rich domains characteristic of other KLP proteins and are localised to the gut of larval *cyathostomin*, the inventors have chosen to designate these proteins *cyathostomin* gut-associated larval antigens (Cy-GALA).

Using any of the Cy-GALA sequences described herein, one of skill in the art could readily identify related or homologous sequences in other species, such as, for example, other *cyathostomin* spp. etc. For example, the nucleic acid sequence encoding these proteins could be used to probe for homologous sequences in other *cyathostomin* species.

Other potentially useful *cyathostomin* larval antigens include those encoded by the following sequences, designated SEQ ID NOS: 37-58. (SEQ ID NOS: 37, 43, and 45 are amino acid sequences and SEQ ID NOS: 38-42, 44, 46-58 are nucleic acid sequences, SEQ ID NOS: 38, 44, and 46 encoding SEQ ID NOS: 37, 43, and 45 respectively). It should be understood that the invention further encompasses proteins, peptides and amino acids having sequences encoded by SEQ ID NOS: 39-42 and 46-58.

SEQ ID NO: 37 (CID-1):
REKARIIQDEYTKRMQQVTPQAQEFLAKWEKTWFTNVQQYSGDKKAF
FKQMIELIPQLMEEVHGFSEETWKSLEEQFPEQTAAWKDNEDRLKQF
YEFIKSLPKQDLAEDPEAFRKFAHLGLQKLLPIEALRA

SEQ ID NO: 38 (nucleic acid sequence encoding CID-1)
AGGGAGAAGGCTAGAATTATTCAAGACGAATACACTAAACGTATGCA
GCAGGTCACACCACAAGCTCAGGAATTCCTGGCAAAATGGGAGAAGA
CATGGTTCACGAATGTGCAGCAATATAGCGGAGATAAGAAAGCTTTC
TTCAAGCAGATGATTGAGCTAATCCCTCAACTAATGGAGGAGGTTCA
TGGGTTCTCGGAAGAGACTTGGAAGAGCCTTGAGGAGCAATTCCCAG
AGCAGACAGCCGCATGGAAAGATAATGAGGATCGCCTAAAGCAATTT
TATGAGTTTATCAAGAGCCTACCCAAGCAGGACTTAGCTGAGGATCC
GGAAGCATTCAGAAAGTTCGCTCACCTCGGACTCCAGAAACTTCTTC
CAATTGAAGCTCTCAGAGCT CID antigens from other *Cyathostomin* organisms may include those encoded by the genomic DNA sequences provided as SEQ ID NOS: 39-42 provided below.

SEQ ID NO: 39
C.cat01-CID
TGGTCACACCACAAGCTCAGGAGTTCCTGGCCAAGGTAAGCTATTAC
CTTACCAGGGTGAGGGGAAAGAAGTTGGCAGCGGTCGGAAACCCGGT
AATCTACTGACTTTACCAATTATTTTCAGTGGGAGAAGACATGGTTC
ACGAATATACAGCAATACAGTGGAGACAAGCAAGCCTTCTTTAAGCA
GATGATTGAACTAATTCCTCAACTTATGGAGGAGGTTCAGGTAAGTT
AGCCGCAAAAATTTTTAACCAATGGTTGAGCTCGACATTTTTTCAGG
GATTCACAGAGGAGACTTGGAATAGCCTGAGGGAGCAATTCCCGGAG
CAGACAGCCGCATGGAAGGATCGTGAGTATCTTTCATAATTACTGTA
CTTGGAATTATACTTTACAATCATAATCCTACTCTTAGACGAGGATC
GCCTGAAGCAATTCTATGAGTTCATTAAGAGCCTACCCAAACAACAA
TTAGCTGAGGTGATTTTCATTGATTTTTCGAAAAATATATTTTTGAT
ACATTCTTTTTCAGGATCCGGAAGCTTTCAGAAAGTTCGCTCACCTC
G SEQ ID NO: 40
C.cat02-CID
TTGTCACACCACAAGCTCAGGAGTTCCTGGCTAAGGTAAGCTATTAC
CTTACCAGGGTGAGGGGGAAGAAGTTGGGAGCGGTCGGAAACCCGGT
AATCTACTGACTTTACCAATTATTTTCAGTGGGAGAGGACATGGTTC
ACGAATATACAGCAATACAGTGGAGACAAGCAAGCCTTCTTTAAGCA
GATGATTGAACTAATTCCTCAACTTATGGAGGAGGTTCAGGTAAGTT
GGCCGCAAAAATTTTTAACCAATGGTTGAGCTCGACATTTTTTCAGG
GATTCACAGAGGAGACTTGGAATAGCCTGAGGGAGCAATTCCCGGAG
CAGACAGCCGCATGGAAGGATCGTAAGTATCTTTCATAATTACTGTA
CTTGGAATTATACTTTACAATCATAATCCTACTCTTAGACGAGGATC
GCCTGAAGCAATTCTATGAGTTCATTAAGAGCCTACCCAAACAACAA
TTAGCTGAGGTGATTTTCATTGATTTTTCGTACGAAAAATATATTTT
TGATACATTCTTTTTCAGGATCCGGAAGCTTTCAGAAAGTTCGCTCA
CCTCG SEQ ID NO: 41
C.lon91-CID
AGGTCACACCACAAGCTCAGGAATTCCTGGCAAAGGTAAGCTATCAC
CTTACCAGGGTGAGGGGTAGAAGTTAGGAGCGAGGGAACCCGGTGAT
CTCTTATACCCATTACTTCAGTGGGAGAAGATATGGTTCACGAATGT
ACAGCAATATAGTGGAGACAAGCAAGCCTTCTTCAAGCAGATGATTG
AACTAATTCCTCAACTTATGGAGGAGGTACAGGTAAGTCAGCTAAAG
TGATTTTAAGAAAAAATTAAGCCTGATTTTCCTTTCAGGGATTCTCA
GAGGAGACTTGGAATAGCCTTAAGGAGCAATTCCCTGAGCAGACAGC
CGCATGGAAGGATAGTGAGTATTTTTCATAATTACTGTACTTGGAAT
TATACTTTACAATCATAATCCTACCCTCAGACGAGGAGCGCCTGAAG
CAATTCTATGAGTTCATTAAGAGCCTACCCAAACAACAAATAGCTGA
GGTGATTTTCATTGATTTTTCGTACGAAAAGTATATTTTTAATACAT
TCTTTTGCAGGATCCGGAAGCCTTCAGAAAGTTCGCTCACCTCG SEQ ID NO: 42
C.nas07-CID
AGGTCACACCACAAGCTCAGGAATTCCTGGCAAAGGTAAGCTACCAT
ATTTCGAGGGGGAGGGCAATTTTGGAGCGAGGGAGGAGAGGAAAGGG
AGAGAAACACTGGTTGGGATCACTAACTCTACCCGCCACTTCCAGTG
GGAGAAGACATGGTTCACGAATGTGCAGCAATATAGCGGAGATAAGA
AAGCCTTTTTCAAACAGATGATTGAGCTAATCCCTCAACTAATGGAA
GAGGTTCATGTAAGTCAACCAAAGTGGCTTTTAAGCGGAGATTAAAC
TCGAATTTTTCTTCAGGGGTTCTCGGAGGAGACTTGGAAGAGCCTTG
AGGAGCAATTCCCAGAGCAGACAGCCGCATGGAAGGATAGTAAGCAT
TCTTCATAGCTCCCGCCTTTATCATTTATCTTCACGATAGTAATCTT
ATTTTTAGATGAGGATCGCCTGAAGCAATTTTATGAGTTCATCAAGA
GCCTACCCAAGCAGGACTTAGCTGAGGTAACTTTCATGGTTTTTTCC
TGAGCTGTAAAAATGCTTGCAACTAACAACTTTTCTAGGATCCGGAA
GCTTTCAGAAAGTTCGCTCACCTCG SEQ ID NO: 43 (FAR-2):
KKESQGFFSIPVDNLRASPFLLQYIKEYIPDYKNAMEKFEDIPKQYR
DLIPEEVATHLKAITAEEKAVLKEVMKDYAKYKDEEEFLKALKEKSE
GLHEKASKLHNFIKGKVDALGDEAKAFVKKVIAAAREVHAKLLAGDK
PSLEDIKKKAKEHMGEFEKLSDDAKEDLKKNFPILTSVWTNEKTRAL
IDKYVEN SEQ ID NO: 44 (nucleic acid sequence encoding (FAR-2)
ATGCTTCGAATAACTTTCTTCCTTGCTCTCTTTGTTGTCTACACTTT
TTCTGCACCCTCTGGACCCGCTGAAGAGAAGATAGATGTGGAAAAAA
TGGAAAAATTTGAAGATATTCCAAAGCAATATCGAGACCTTATTCCG
GAAGAGGTAGCTACACACCTCAAAGCCATCACCGCTGAAGAGAAAGC
TGTTCTAAAAGAGGTAATGAAGAATTATGCAAAGTACAAGAACGAGG
AGGAGTTTTTGGAAGCGTTGAAAGAAAAATCAGAGAGTTTGCATGAG
AAAGCCAGCAAACTTCACAATTTTATCAAAGGGAAGGTTGACGCACT
TGGAGATGAAGCAAAGGCATTTGTGAAGAAGGTTATCGCAGCTGCTC
GAGAAGTGCATGCCAAACTTCTTGCCGGGGACAAACCATCGCTTGAA

```
GATATCAAGAAGAAAGCCAAGGAGCATATGGCTGAATTCGAGAAACT
AAGCGATGATGCCAAGGAGGATCTCAAAAAGAATTTCCCAATCCTTA
CTTCCGTCTGGACAAATGAGAAAACAAGAGCGTTGATTGACAAATAT
GTGGAGAAC

SEQ ID NO: 45 (UNK-50a):
GKMSDLWTAISETNKVRLFNTLSLGIAGVLCITTAFIPVENQVVCAV
LITLLQGVIGFNSAGYNKAAVIVARQHAHLLLTCFGLIVTFVPLVQP
FIVQLVAPDHSWDQWFYLFVGHGLVLVIANLFFCLTIEAKPAAFTQK
TDSS

SEQ ID NO: 46 (nucleic acid sequence encoding
UNK-50a)
GGTAAAATGTCAGATTTATGGACGGCAATAAGCGAAACAAATAAGT
CCGCTTGTTCAACACCTTGTCGCTGGGAATTGCTGGCGTACTGTGTA
TAACTACTGCTTTCATTCCTGTGGAAAATCAGGTTGTTTGCGCTGTT
TTAATCACGTTATTGCAAGGAGTTATCGGATTCAATTCAGCTGGATA
TAACAAAGCTGCAGTCATTGTTGCTAGGCAGCATGCTCATCTTCTGT
TGACCTGCTTTGGGCTCATTGTCACTTTTGTCCCCTTGGTGCAGCCA
TTCATAGTTCAACTTGTGGCCCCTGACCATAGCTGGGACCAATGGTT
TTATCTGTTTGTTGGGCATGGTCTCGTACTTGTTATAGCGAATTTAT
TCTTTTGTCTCACTATCGAGGCGAAACCGGCAGCGTTCACACAGAAA
ACTGATTCATCA
```

The following sequences represent nucleic acid sequences encoding potentially useful EL3 antigens (or fragments or portions thereof). As above, it should be understood that the in addition to these nucleic acid sequences, the present invention relates to amino acid sequences comprising sequences encoded by SEQ ID NOS: 47-58 or derivatives, variants or homologues thereof.

```
                                     SEQ ID NO: 47
EL3sequence1
GGTTTAATTACCCAAGTTTGAGGTACTTTCTAAATCTGACCCGATCAA
CTGATTGTGGTCTGATTAAATTTTGAAAATCTCTCCCTGAATAGGGAG
AGTACAAGAGTGCATATCCAAAAAAAAAAAAAAAAAAAAAAAAAAAA
ACATGTCGGCCGCCTCGGCCTCTAGAATA SEQ ID NO: 48
EL3sequence2
GGTTTAATTACCCAAGTTTGAGTGTCATGAAGCTTGCCTGAAAAAGCA
GAGAAACCAAGAGGAGATAGTTTCACAGTTCCGCCAGACAGGAAATGCG
TGCCAAGATGTTTTGCGGAAGAGGAGAAACGTCGTTCACTTAGAATGAG
AAGGCATTGATTCTGTTTAGTCGTTGAGATATTTAAAAATTCTTTGCAG
AAAACCTTTTCAAATCATAAAGTCGAAGACCACAAAAAAAAAAAAAAA
AAAAAAAAAAAAAACATGTCGGCCGCCTCGGCCTCTAGAATA SEQ ID NO: 49
EL3sequence3 (Cy-Ins-1)
GGTTTAATTACCCAAGTTTGAGGCTGCTTCAACAGTAGGTTTAGAAATGA
CATCGCGGATATGGCGCCGCACCCAGAGCCCTCCATTATTGCTACTCCTG
TTGTTGATCAGTCTACCAGTAGCTGAGTGTAGTATTCGACTATGTGGAGT
GCGACTAACACGAACTCTTATGGCTATCTGCAGGAATCAATTATGCGGTT
ATTCGCAAAGTAAAAGATCTGCTATGTGGGAAGAGCCTCGACTGGAAACC
GTGCACTCAACAATGAAACGATCAGGGATCGCCACCGAATGCTGCGAGAA
TCGGTGCTCATTTAGCTACTTAAAGACATACTGCTGCAGCACTTAGCCTT
GGCATCTTAAGCCGCTTTTATCTCCTCTCCATGATCTCTCTTCGTTATCT
GTATAACCGAATATAGTCATTCCGGAAATGCGGATGCTTAGGCCAATTTG
TTGACGTTTGCCGCATGAATCATTTGCTGTTCGTCATTATCTCACAGACG
TGTAAAAGATCTCTTTTTATGAAAGTCTATTTTGTTTGAGCTGCACCATT
AAACCGTTCACAAAAAAAAAAAAAAAAAAAAAAAAAAAACATGTCGGC
CGCCTCGGCCTCTAGAATAA SEQ ID NO: 50
EL3sequence4
GGTTTAATTACCCAAGTTTGAGGTACTTTCTAGATCTGACCCGATCAACT
GATTGTGGTCTGATTAAATTTTGGAAATCTCTTCCTGAACAGGGAGAGTA
CAAGAGTGTATATGAAAAAAAAAAAAAAAAAAAAAAAAAAAACATGTC
GGCCGCCTCGGCCTCTAGAATA SEQ ID NO: 51
EL3sequence5
GGTTTAATTACCCAAGTTTGAGGATGCTTAGTTTCAAGCTCGTTCTTCTC
TTCGTACTTCTCACAGCTTGTGTGCTAACAGATCCAAGAGTGTTAATCCG
AGAAAAGCGAATGGACTGGAGACGTTACTATAGCAGATGGGGTCGCGGAA
GCTCTAATTGGGGAAACCGCGGAGGTACCTTCGGCGGACGAAAATGGAGT
TACCCGACTTTTGGACAATGGGGACATTAACATCTGATGTATGAAAAGAT
CTAATGAAATAAAGCTTCGAAAAAAAAAAAAAAAAAAAAAAAAAAAAAC
ATGTCGGCCGCCTCGGCCTCTAGAATA SEQ ID NO: 52
EL3sequence6 (Cy-Cbg-1)
GGTTTAATTACCCAAGTTTGAGAATGTTCGAAAAATTCCTTCTGCTACTG
ATCGTTGTGATCGCCCTCATTTCTTTGGCGTCTGCAGATTTTTCATGCTT
CTTCGGTGATACCATCTGCAAGAGCATTACATGCAGGGGCTGCACCGTCG
CCACTTGCCTTAATGGAGACTGTATGTGCACACTATGTAACTGATGATCT
TCACATGTCGCATTACCATTTGTAACAAATACATTTTCTCTTGTTCATAA
TAAATTTTTCACTCAAAAAAAAAAAAAAAAAAAAAAAAAAAACATGTC
GGCCGCCTCGGCCTCTAGAATA SEQ ID NO: 53
EL3sequence7
GGCCGCGGGATTTTCTAGAGGCCGAGGCGGGTTTTAGGTTGTTCCTCAAA
CTTGGGTAATTAAACCACGAGGCCGAGGCGGGTTTTAGGTTGTTCTCAAA
CTTGGGTAATTAAACCACGATGGCGAGGCGGGTTTTAGGTTGTTCTCAAA
CTTGGGTAATTAAACCACGATGGCGAGGCGGGTTTTAGGTTGTTCCTCAA
ACTTGGGTAATTAAACCAAGAGGCCGAGGCGGGTTTTAGGTTGTTCCTCA
AACTTGGGTAATTAAACCACGATGGCGAGGCGGGTTTTAGGTTGTTCTCA
AACTTGGGTAATTAAACCAATCACTAGT SEQ ID NO: 54
EL3sequence8
GGCCGCGGGATTATTCTAGAGGCCGAGGCAGTGGTATCAACGCAGAGTGG
CCATTACGGCCGGGGAGAGGGAAAAGTTTCTTTTCTCTCGGATACCCATG
TCGGCCGCCTCGGCCTCTAGAATA SEQ ID NO: 55
EL3sequence9
GGCCGCGGGATTTTCTAGAGGCCGAGGCGTCTTACTTGGGTGGCTCAATA
ACTGAAAGCTTAGAATTCATTAAACCTTAACCCACAGGGGTTATTTGACA
TGCTTGACTTGAAAATGATGCTCTTCTGCTTGTAGTTGTTTTATTATGCT
AGCTGTAAGTATACTCTGGTAGACCAGAACATCAATGTGCTAGTTGAATG
TATCATGTTATCACTTTGTCACACTCTATACGAATCTAGGTGTGGCAGGC
CACACCCCTCTCCTGACCCTGTTCACCATCAATTAGCTTTTAGCTGTTAT
TTAATAACATCACACTGATTGCAAAAAAAAAAAAAAAAAAAAAAAAAAA
AACATGTCGGCCGCCTCGGCCTCTAAAAAATCACTAGT SEQ ID NO: 56
EL3sequence10
GGCCGCGGGATTATTCTAGAGGCCGAGGCAGTGGTATCAACGCAGAGTGG
CCATTACGGCCGAAGCAGTGGTATCAACGCAGAGTGGCCATTACGGCCGG
GTGGTGACCACGGGTGACGGGGAATTAGGGTTCGATTCCGGAGAGGGAGC
CTGAGAAACGGCTACCCATCCAAGGAAGGCAGCAGGCGGCAAATTACC
CACTCCCGACCCGGGGAGGTAGTGACGAAAAAAAAAAAAAAAAAAAAA
AAAAAAAACATGTCGGCCGCCTCGGCCTCTAGAATAATCACTAGT SEQ ID NO: 57
EL3sequence11
GGCCGCGGGATTTTCTAGAGGCCGAGGCGGGTTTTAGCTCAAACTTGGGT
AATTAAACCGGTAGGATGGCGAGGCGGGTTTCTCAAACTTGGGTAATTAA
ACCAGTAGGATGGCGAGGCGGGTTTCTCAAACTTGGGTAATTAAACCGGT
AGGAGGCCGAGGCGGGTCTCAAACTTGGGTAATTAAACCAATCACTAGT SEQ ID NO: 58
EL3sequence12
CAAGTTTGAGGTACTTTCTAGATCTGACCCGATCAACTGATTGTGGTCTG
ATTAAATTTTGGAAATCTCTTCCTGAACAGGGAGAGTACAAGAGTGTATA
TTAAGAAAAAAAAAAAAAAAAAAAAAAAAAAAAAAACATGTCGGCCGCCTC
GGCCTCTAGAATAATCACTAGT
```

As such, the present invention relates to the proteins encoded by the sequences designated as SEQ ID NOS: 1, 3, 5, 7, 37, 43 and 45, the corresponding gene sequences (such as, for example, those given as SEQ ID NOS: 2, 4, 6, 8, 38, 44, 46) and proteins, peptides and/or amino acids comprising sequences encoded by SEQ ID NOS 9, 11, 13, 15, 17, 19, 21, 23, 25, 27, 29, 31, 33, 35, 39-42, and 47-58, as well as any fragments, portions, mutants, variants, derivatives, analogues and/or homologoues/orthologues thereof. Furthermore, the methods described herein may provide means for detecting levels of antibodies which bind to proteins comprising (or encode by) any of SEQ ID NOS: 1-58 (or fragments, portions, mutants, derivatives, analogues or variants thereof).

Typically the fragments, portions, mutants, variants, derivatives, analogues and/or homogoues/orthologues mentioned in this invention are immunogenic or encode immunogenic *cyathostomin* larval antigens—that is, they are capable of generating immune, preferably humoral, responses.

The term "mutants" may encompass naturally occurring mutants or those artificially created by the introduction of one or more amino acid/nucleic acid additions, deletions, substitutions or inversions.

One of skill in this field will readily understand that proteins or nucleic acids homologous to the proteins encoded by SEQ ID NOS: 1, 3, 5, 7, 37, 43 and 45 or nucleic acid sequences of SEQ ID NOS: 2, 4, 6, 8, 38, 39-42, 44, 46, and 47-58, may exhibit as little as 20 or 30% sequence homology or identity thereto (or to a portion thereof). In other instances however, homologous proteins or nucleic acid sequences may exhibit at least 40, 50, 60, 65 70, 75, 80, 85, 90, 91, 92, 93, 94, 95, 96, 97, 98, 99% homologly or identity the whole or part of SEQ ID NOS: 1-9, 11, 13, 15, 17, and 19 detailed above. As such, proteins or nucleic acids homolous to (or partially identical with) the proteins and/or nucleic acid sequences provided by SEQ ID NO: 1-9, 11, 13, 15, 17, and 19 are also included within the scope of this invention.

It should also be understood that natural variations due to, for example, polymorphisms, may exist between related (or homologous) proteins/genes from any given *cyathostomin* species. These variants may manifest as proteins/genes which exhibit one or more amino/nucleic acid substitutions, additions, deletions and/or inversions relative to a reference sequence (for example any of the sequences provided by SEQ ID NOS: 1-58 described above). All such variants, especially those which are functional and/or are immunogenic (or encode functional/immunogenic proteins or peptides) are to be included within the scope of this invention.

Additionally, or alternatively, analogues of the various peptides described herein may be made by introducing one or more amino acid substitutions into the primary sequence. In certain embodiments, one or more of these substitutions may represent a "conservative substitution". One of skill in this field will undertsand that the term "conservative substitution" is intended to embrace the act of replacing one or more amino acids of a protein or peptide sequence with an alternate amino acid with similar properties and which does not substantially alter the physio-chemical properties and/or structure or function of the native (or wild type) protein.

As is well known in the art, the degeneracy of the genetic code permits substitution of one or more bases in a codon without changing the primary amino acid sequence. Consequently, although the nucleic acid sequences described in this application are known to encode potentially useful *cyathostomin* larval antigens, the degeneracy of the code may be exploited to yield variant nucleic acid sequences which encode the same primary amino acid sequences.

Also encompassed by this invention are splice variants of the primary gene transcripts encoded by any of the gene sequences described herein, as well as and the translated *Cyathostomin* larval antigen splice variant proteins which are encoded thereby. By way of example, splice variants of the Cy-GALA proteins described herein, including, for example, variants encoded by transcripts having 115 bp segment deletions, are within the scope of this invention. Furthermore, one of skill in this field will readily appreciate that polyadenylation variants and start codon variants, including cDNA sequences encoding the same, may also be included within the scope of this invention.

As stated, this invention finds particular application in the identification or diagnosis of *cyathostomin* infections in horses but may be more generally be used to diagnose or identify *cyathostomin* infections present in other species of the Equidae family including, for example, donkeys and zebra The term "sample" should be understood as including any samples comprising antibodies and/or *cyathostomin* larval antigens. For example, suitable samples may include fluids such as whole blood, plasma, serum, saliva, sweat and/or semen. In other instances "samples" such as tissue biopsies and/or scrapings may be used. In particular biopsies or scrapings from the gut may be used. In addition, a sample may comprise a tissue or gland secretion and washing protocols may be used to obtain samples of fluid secreted into, for example, the gut. In other embodiments, faecal samples may be used. One of skill will understand that in order to prepare a faecal sample for use, it may be necessary to add buffers and various protease inhibitors and subject the sample to procedures such as centrifugation, to remove particulate material. As such, "faecal samples" may represent suitable samples for use in the methods provided by this invention. As stated, a "reference" or "control" sample may be derived from healthy animals or from animals not having high mucosal burdens of *cyathostomin* parasites or larval cyathostominosis.

In order to identify a level of anti-*cyathostomin* larval antigen antibodies present in a sample, the sample may be contacted with one or more *cyathostomin* larval antigen(s) (such as those provided, comprising or encoded by SEQ ID NOS: 1-58) under conditions which permit binding between any anti-*cyathostomin* larval antigen antibodies present in the sample and the *cyathostomin* larval antigen(s). Anti-*cyathostomin* larval antigen antibodies bound to *cyathostomin* larval antigen may easily be detected with the use of agents capable of binding anti-*cyathostomin* larval antigen antibodies. In one embodiment, the agents capable of binding anti-*cyathostomin* larval antigen antibodies may be conjugated or linked to a detectable moiety.

One of skill will appreciate that while the methods provided by this invention may provide a means of detecting antibodies having affinity for, or specificity/selectivity to a single *cyathostomin* antigen (such as any described herein), in certain embodiments, the methods may exploit the use of one or more of the *cyathostomin* antigens. Since, for example, horses tend to be infected with one or more different *Cyathostomin* species, assays/methods which utilise cocktails of *cyathostomin* antigens provide a means of increasing the likelihood of a positive diagnosis. Accordingly, it should be understood that the methods described herein may use one or more of the *cyathostomin* antigens described herein.

In one embodiment, the methods provided by this invention may utilise substrates to which one or more *cyathostomin* larval antigens have been bound, conjugated or immobilised. One of skill in that art will appreciate that in addition to techniques which allow antigens to be bound, conjugated or immobilised "directly" on to the surface of substrates, other techniques may involve the use of substrates which have been coated with agents capable of binding *cyathostomin* larval antigens.

It is to be understood that the term "agents capable of binding *cyathostomin* larval antigens" may include, for example, antibodies such as monoclonal or polyclonal antibodies and/or other types of peptide or small molecule capable of binding to *cyathostomin* larval antigens. It should be noted that this definition applies to all types of binding agent mentioned herein. Furthermore, references to "antibodies" herein are indented to encompass "anti-*cyathostomin* larval antigen antibodies".

The techniques used to generate antibodies (either monoclonal or polyclonal) are well known to one of skill and may involve the use of *cyathostomin* antigens (or fragments or portions thereof) either isolated or purified from *cyathostomin* parasites or recombinantly generated as described herein.

Suitable substrates may include, for example, glass, nitrocellulose, paper, agarose and/or plastics. A substrate such as, for example, a plastic material, may take the form of a microtitre plate.

In order to detect a level of antibody present in a sample, immunological detection techniques such as, for example, enzyme-linked immunosorbent assays (ELISA) may be used. One of skill in this field will appreciate that ELISAs may use substrates to which *cyathostomin* larval antigens have been "captured" or bound by binding agents (capable of binding *cyathostomin* larval antigens) bound or immobilised to the substrate. Alternatively, substrates may comprise *cyathostomin* larval antigens, which have been directly bound or immobilised to the substrate.

An ELISA may involve contacting the sample to be tested with a substrate under conditions which permit binding between any antibodies present in the sample and the *cyathostomin* larval antigens bound or immobilised to the substrate as described above. One familiar with these techniques will appreciate that prior to contacting the sample to be tested with the substrate, a blocking step may be introduced to reduce incidences of non-specific binding.

An ELISA may comprise the further step of contacting the substrate with a further binding agent capable of binding one or more of the antibodies present in the sample. Such agents may otherwise be known as "secondary antibodies" and may take the form of rodent or ruminant antibodies specific to particular forms of equine antibody.

Secondary antibodies useful in the present invention may be conjugated to moieties which permit them to be detected (referred to hereinafter as "detectable moieties"). For example, the secondary antibodies may be conjugated to an enzyme capable of reporting a level via a colourmetric chemi-luminescent reaction. Such conjugated enzymes may include but are not limited to Horse Radish Peroxidase (HRP) and Alkaline Phosphatase (AlkP). Additionally, or alternatively, the secondary antibodies may be conjugated to a fluorescent molecule such as, for example a fluorophore, such as FITC, rhodamine or Texas Red. Other types of molecule which may be conjugated to binding agents include radiolabelled moieties.

The amount of secondary antibody (identifiable by means of the detectable moiety) bound to the anti-*cyathostomin* larval antibodies, may be representative of the anti-*cyathostomin* larval antibodies present in the sample tested.

Alternatively, in order to identify a level of *cyathostomin* larval antigen present in a sample, a substrate or substrate comprising one or more agents capable of binding one or more *cyathostomin* larval antigens, may first be contacted with a sample to be tested. Any *cyathostomin* larval antigen bound to the substrate or to the agents capable of binding the *cyathostomin* larval antigen, may be detected with the use of a further agent capable of binding the *cyathostomin* larval antigen (referred to hereinafter as the "primary binding agent"). Additionally, or alternatively, the primary binding agents may have affinity for, or bind to *cyathostomin* larval antigen::substrate complexes or complexes comprising *cyathostomin* larval antigen and the abovementioned agents capable of binding the *cyathostomin* larval antigen. In one embodiment, the primary binding agent may be an antibody conjugated to a detectable moiety as described above.

Alternatively, any *cyathostomin* larval antigen bound to the substrate or agents capable of binding the *cyathostomin* larval antigen, may be detected by means of a yet further binding agent having affinity for the primary binding agents. In certain embodiments, the further binding agents may be conjugated to detectable moieties.

In one embodiment, the methods for identifying a level of *cyathostomin* larval antigen or a level of anti-*cyathostomin* larval antigen antibodies, may take the form of "dip-stick" test, wherein a substrate (or portion thereof) is contacted with a sample to be tested under conditions which permit the binding of any *cyathostomin* larval antigen or anti *cyathostomin* larval antigen antibodies present in the sample, to the substrate or a binding agent bound or immobilised thereto.

Other techniques which exploit the use of agents capable of binding the *cyathostomin* larval antigen or antibodies which bind thereto include, for example, techniques such as western blot or dot blot. A western blot may involve subjecting a sample to electrophoresis so as to separate or resolve the components, for example the proteinaceous components, of the sample. In other embodiments, electrophoresis techniques may be used to separate proteins purified from *cyathostomin* parasites and/or proteins generated in a recombinant form. The resolved components/proteins may then be transferred to a substrate, such as nitrocellulose.

In order to identify any *cyathostomin* larval antigen present in a sample, the substrate (for example nitrocellulose substrate) to which the resolved components and/or proteins have been transferred, may be contacted with a binding agent capable of binding *cyathostomin* larval antigens under conditions which permit binding between any *cyathostomin* larval antigen in the sample (or transferred to the substrate) and the agents capable of binding the *cyathostomin* larval antigen.

Advantageously, the agents capable of binding the *cyathostomin* larval antigen may be conjugated to a detectable moiety.

Additionally, the substrate may be contacted with a further binding agent having affinity for the binding agent(s) capable of binding the *cyathostomin* larval antigen. Advantageously, the further binding agent may be conjugated to a detectable moiety.

Similar techniques may also be used to detect levels of anti-*cyathostomin* larval antigen antibodies present in samples. Techniques of this type may be known as "immunoblots" or "dotblots" or 'dipsticks' where *cyathostomin* antigen(s) is/are immobilised onto suitable substrates (for example a nitrocellulose substrate) and contacted with agents capable of binding *cyathostomin* antigen(s). In certain embodiments any of the samples described above may be used a source of *cyathostomin* antigen. Additionally or alternatively, the *cyathostomin* larval antigen may be isolated or purified from the parasite, or produced in recombinant form.

Other immunological techniques which may be used to identify a level of *cyathostomin* larval antigen in a sample include, for example, immunohistochemistry wherein binding agents, such as antibodies capable of binding *cyathostomin* larval antigens, are contacted with a sample such as those described above, under conditions which permit binding between any *cyathostomin* larval antigen present in the sample and the *cyathostomin* larval antigen binding agent. Typically, prior to contacting the sample with the binding agent, the sample is treated with, for example a detergent such as Triton X100. Such a technique may be referred to as "direct" immunohistochemical staining.

Alternatively, the sample to be tested may be subjected to an indirect immunohistochemical staining protocol wherein, after the sample has been contacted with a *cyathostomin* larval antigen binding agent, a further binding agent (a secondary binding agent) which is specific for, has affinity for, or is capable of binding the *cyathostomin* larval antigen binding agent, is used to detect *cyathostomin* larval antigen/binding agent complexes.

The skilled person will understand that in both direct and indirect immunohistochemical techniques, the binding agent or secondary binding agent may be conjugated to a detectable moiety. Preferably, the binding agent or secondary binding agent is conjugated to a moiety capable of reporting a level of bound binding agent or secondary binding agent, via a colourmetric chemiluminescent reaction.

In order to identify the levels of *cyathostomin* larval antigen present in the sample, one may compare the results of an immunohistochemical stain with the results of an immunohistochemical stain conducted on a reference sample. By way of example, a sample revealing more bound *cyathostomin* larval antigen binding agent (or secondary binding agent) than in a reference sample, may have been provided by a subject with a *cyathostomin* infection.

In addition to the methods and techniques described above, the present invention also contemplates the use of a range of PCR based techniques which may be used to detect levels of *cyathostomin* antigen gene expression or gene quantity in a given sample. Useful techniques may include, for example, polymerase chain reaction (PCR) using genomic DNA as template or reverse transcriptase (RT)-PCR (see below) based techniques in combination with real-time PCR (otherwise known as quantitative PCR). In the present case, real time-PCR may used to determine the level of expression of the genes encoding any of the *cyathostomin* larval antigens described herein. Typically, and in order to quantify the level of expression of a particular nucleic acid sequence, RT-PCR may be used to reverse transcribe the relevant mRNA to complementary DNA (cDNA). Preferably, the reverse transcriptase protocol may use primers designed to specifically amplify an mRNA sequence of interest (in this case a *cyathostomin* mRNA encoding a *cyathostomin* larval antigen). Thereafter, PCR may be used to amplify the cDNA generated by reverse transcription. Typically, the cDNA is amplified using primers designed to specifically hybridise with a certain sequence and the nucleotides used for PCR may be labelled with fluorescent or radiolabelled compounds.

One of skill in the art will be familiar with the technique of using labelled nucleotides to allow quantification of the amount of DNA produced during a PCR. Briefly, and by way of example, the amount of labelled amplified nucleic acid may be determined by monitoring the amount of incorporated labelled nucleotide during the cycling of the PCR.

Further information regarding the PCR based techniques described herein may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

Other techniques that may be used to determine the level of *cyathostomin* larval antigen gene expression in a sample, include, for example, northern and/or Southern blot techniques. A northern blot may be used to determine the amount of a particular mRNA present in a sample and as such, could be used to determine the amount of *cyathostomin* larval antigen gene expression. Briefly, total or messesnger (m)RNA may be extracted from any of the samples described above using techniques known to the skilled artisan. The extracted RNA may then be subjected to electrophoresis. A nucleic acid probe, designed to hybridise (i.e. complementary to) an RNA sequence of interest—in this case the mRNA encoding a *cyathostomin* larval antigen, may then be used to detect and quantify the amount of a particular mRNA present in a sample.

Additionally, or alternatively, a level of *cyathostomin* larval antigen gene expression may be identified by way of microarray analysis. Such a method would involve the use of a DNA micro-array which comprises nucleic acid derived from *cyathostomin* larval antigen genes. To identify a level of *cyathostomin* larval antigen gene expression, one of skill in the art may extract the nucleic acid, preferably the mRNA, from a sample and subject it to an amplification protocol such as, RT-PCR to generate cDNA. Preferably, primers specific for a certain mRNA sequence—in this case sequences encoding *cyathostomin* larval antigen genes may be used.

The amplified *cyathostomin* larval antigen cDNA may be subjected to a further amplification step, optionally in the presence of labelled nucleotides (as described above). Thereafter, the optionally labelled amplified cDNA may be contacted with the microarray under conditions which permit binding with the DNA of the microarray. In this way, it may be possible to identify a level of *cyathostomin* larval antigen gene expression.

In addition, other techniques such as deep sequencing and/or pyrosequencing may be used to detect *cyathostomin* larval antigen sequences in any of the samples described above, particularly faecal matter extracts. Further information on these techniques may be found in "Applications of next-generation sequencing technologies in functional genomics", Olena Morozovaa and Marco A. Marra, Genomics Volume 92, Issue 5, November 2008, Pages 255-264 and "Pyrosequencing sheds light on DNA sequencing", Ronaghi, Genome Research, Vol. 11, 2001, pages 3-11.

The present invention also extends to kits comprising reagents and compositions suitable for diagnosing *cyathostomin* infections. For example, depending on whether or not the kits are intended to be used to identify levels of *cyathostomin* larval antigen or antibodies thereto in samples, the kits may comprise substrates having *cyathostomin* larval antigens or agents capable of binding *cyathostomin* larval antigens, bound thereto. In addition, the kits may comprise agents capable of binding *cyathostomin* larval antigens—particularly where the kit is to be used to identify levels of *cyathostomin* larval antigens in samples. In other embodiments, the kit may comprise agents capable of binding the *cyathostomin* larval antigens, for example specifically raised polyclonal antibodies or monoclonal antibodies. Where the kits are intended to diagnose equine *cyathostomin* larval infections, these binding agents may take the form of antibodies capable of binding equine antibodies. The antibodies may be conjugated to detectable moieties. Kits for use in detecting the expression of genes encoding *cyathostomin* larval antigen gene may comprise one or more oligonucleotides/primers for detecting/amplifying/probing *cyathostomin* larval antigen encoding sequences. The kits may also comprise other reagents to facilitate, for example, sequencing, PCR and/or RFLP analysis. All kits described herein may further comprise instructions for use.

It will be appreciated that the uses, medicaments and methods of treatment described herein may require the generation of recombinant *cyathostomin* larval antigens (or genes encoding the same) and as such, the present invention further contemplates methods of generating and/or expressing recombinant *cyathostomin* larval antigen genes and/or proteins (such as for example those described above as SEQ ID NOS: 1-58). One of skill in this field will appreciate that PCR techniques may be exploited to selectively obtain *cyathostomin* larval antigen gene sequences from a variety of sources including, for example, equine gut tissue, faecal matter or extracts prepared from *cyathostomin* nematodes. In one embodiment, molecular cloned *cyathostomin* larval antigen gene sequences may be introduced into a vector (such as a plasmid or expression cassette). In one embodiment, the vector may further comprise a nucleotide sequence of a tag or label to assist in protein purification procedures.

A host cell may be transformed with the vector and maintained under conditions suitable to induce expression of the *cyathostomin* larval antigen gene sequence and production of recombinant *cyathostomin* larval antigen. Techniques used to purify recombinant proteins generated in this way are known and, where the recombinant protein is tagged or labelled, these may include the use of, for example, affinity chromatography techniques.

In view of the above, further aspects of this invention provide an expression vector comprising a *cyathostomin* larval antigen gene sequence and a host cell transformed therewith, respectively.

In a further aspect, the present invention provides a method for determining whether or not an equine subject should be treated with anthelmintic drug, said method comprising the step of detecting a level of anti-*cyathostomin* larval antigen antibodies in a sample as per the first aspect of this invention and/or a level of *cyathostomin* larval antigen in a sample, wherein a level of anti-*cyathostomin* larval antigen antibodies and/or antigen, is indicative of an equine subject that should be administered a anthelminitc drug. In one embodiment, the anthelminitc drug may be Moxidectin.

DETAILED DESCRIPTION

The present invention will now be described in detail and with reference to the following Figures which show:

FIG. 1. ClustalW alignment of Cy-GALA-1 with its orthologues in other nematode species. *Cyathostomin* (Cy) GALA-1 is compared to *N. brasiliensis* keratin-like protein (Nb-KLP) (accession number: BAB68205); *T. circumcincta* (Tc) (AAM45145); *O. ostertagi* (Oo) (CAD22110); *C. elegans* (Ce) KLP-1 (NP_502026) and Ce-KLP-2 (NP_501448). The signal peptide for each sequence is underlined and the domain of unknown function (DUF148) is boxed. The histidine-rich region is highlighted in grey and the glycine-rich regions of the *C. elegans* sequences are shown in bold.

FIG. 2: Development transcription pattern of Cy-gala-1. RT-PCR was performed using gene-specific primers for Cy-gala-1 and the housekeeping gene cytochrome oxidase c subunit I (coxI), from mixed-species pools of EL3 (lane 1), DL (lane 2) and LP (lane 3) cDNA. For each reaction no-template controls were performed (N). Sizes in base pairs (bp) are labelled on the left-hand side.

Figure 3A:
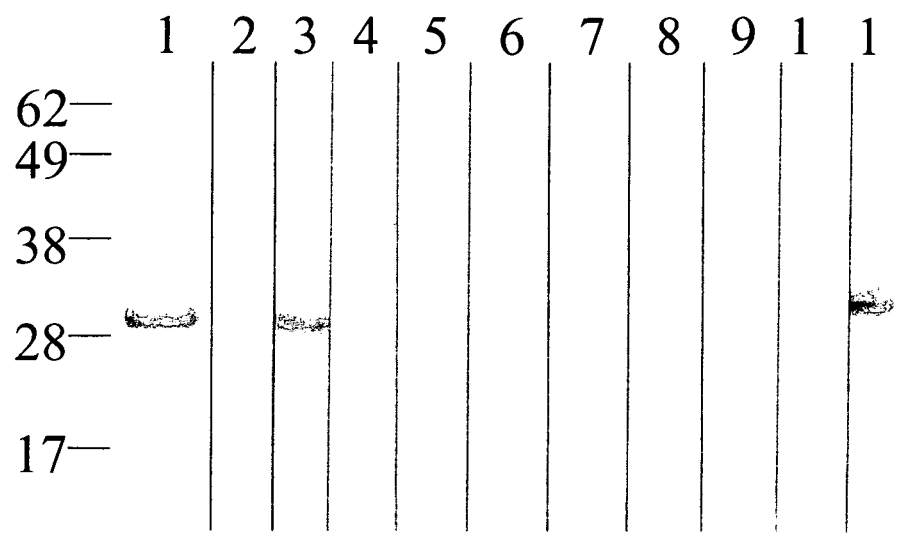
Figure 3B:
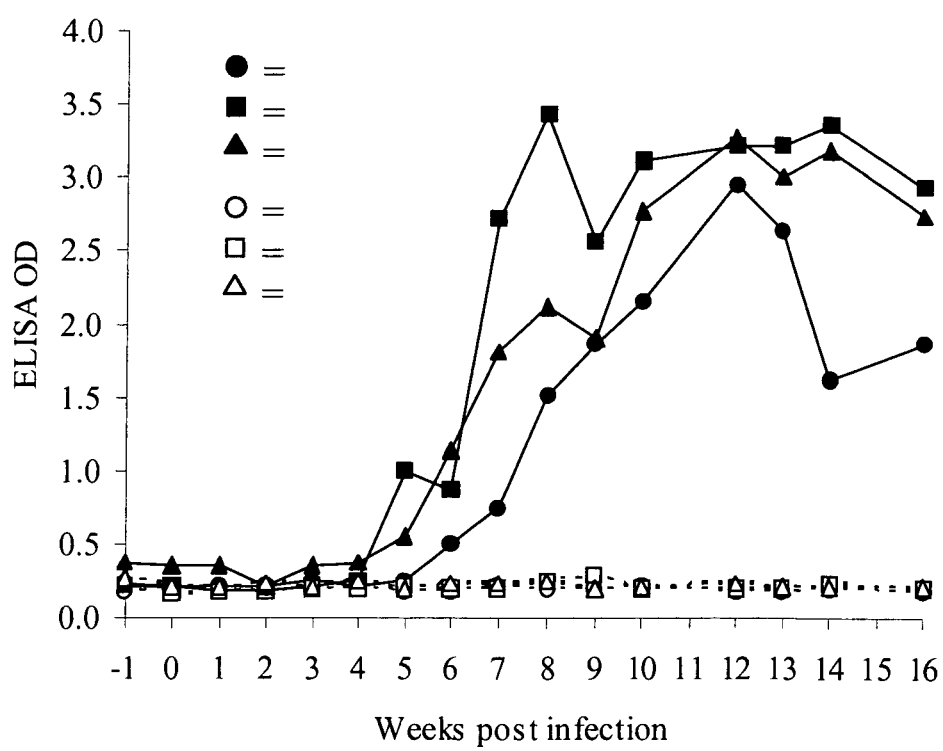

FIG. 3. Immunoreactivity of rCy-GALA-1. IgG(T) reactivity to rCy-GALA-1 in horses infected with cyathostomins or other helminths as assessed by (A) immunoblot and (B) ELISA. FIG. 3A. Lane 1: Coomassie blue. Lanes 2-11: IgG (T) reactivity of specific equine sera: HF (2); CI (3); a pool of sera from *cyathostomin*-free horses (n=5) from an abattoir (4); a pool of sera from *cyathostomin*-infected horses which harboured total mucosal larval burdens of >100,000 (n=6) from an abattoir (5); horses mono-specifically infected with *P. equorum* (6), *S. edentatus* (7), *S. westeri* (8) or *S. vulgaris* (9). Also shown is IgG reactivity in sera from a rabbit before (lane 10) and after two immunisations (lane 11) with a 20 kDa complex purified from EL3/DL somatic extracts [11]. FIG. 3B. ELISA indicating IgG(T) reactivity to rCy-GALA-1 antigen in equine sera over an experimental infection [29]. Responses in the CI group are depicted by the solid lines and black shapes and in the HF group by dashed lines and white shapes.

Figure 4A:
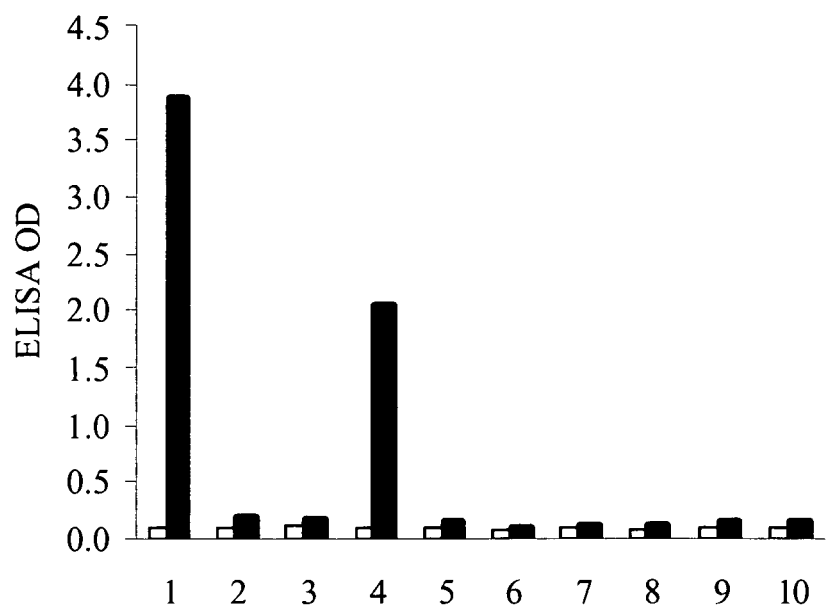
Figure 4B:
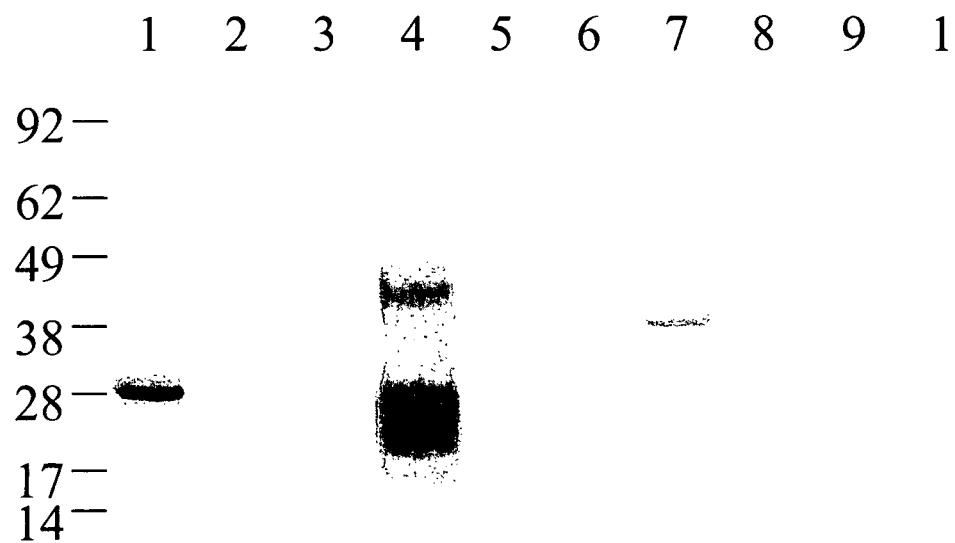

FIG. 4: Reactivity of anti-rCy-GALA-1 antiserum to cyathostomins and other equine helminths. IgG(T) responses were assessed by (A) ELISA and (B) immunoblot. ELISA results depict binding of anti-rCy-KLP-1 anti-sera (black) and pre-immunisation serum (white). For both assays, the antigens were as follows: 1=rCy-GALA-1; 2=*cyathostomin* IL3; 3=*cyathostomin* EL3; 4=*cyathostomin* DL; 5=*cyathostomin* LP; 6=adult *A. perfoliata;* 7=adult *P. equorum;* 8=adult *S. edentatus;* 9=adult *S. vulgaris;* 10=adult *S. equinus.*

Figure 5:
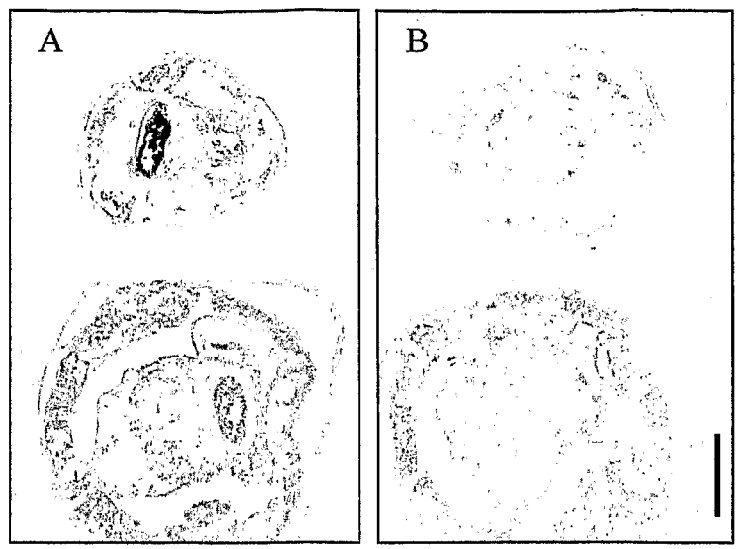

FIG. 5: Immunolocalisation of Cy-GALA. Transverse sections of DL cyathostomins were probed with anti-rCy-GALA-1 antiserum (A) and pre-immunization serum (B). Specific binding of antiserum in the parasite gut is indicated by the black arrows. The vertical bar represents 40 µm.

Figure 6:
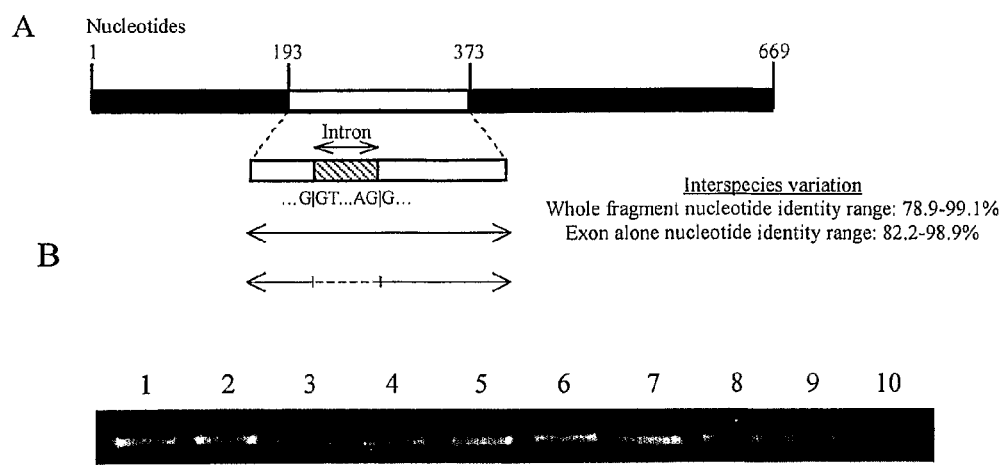
Figure 8A:
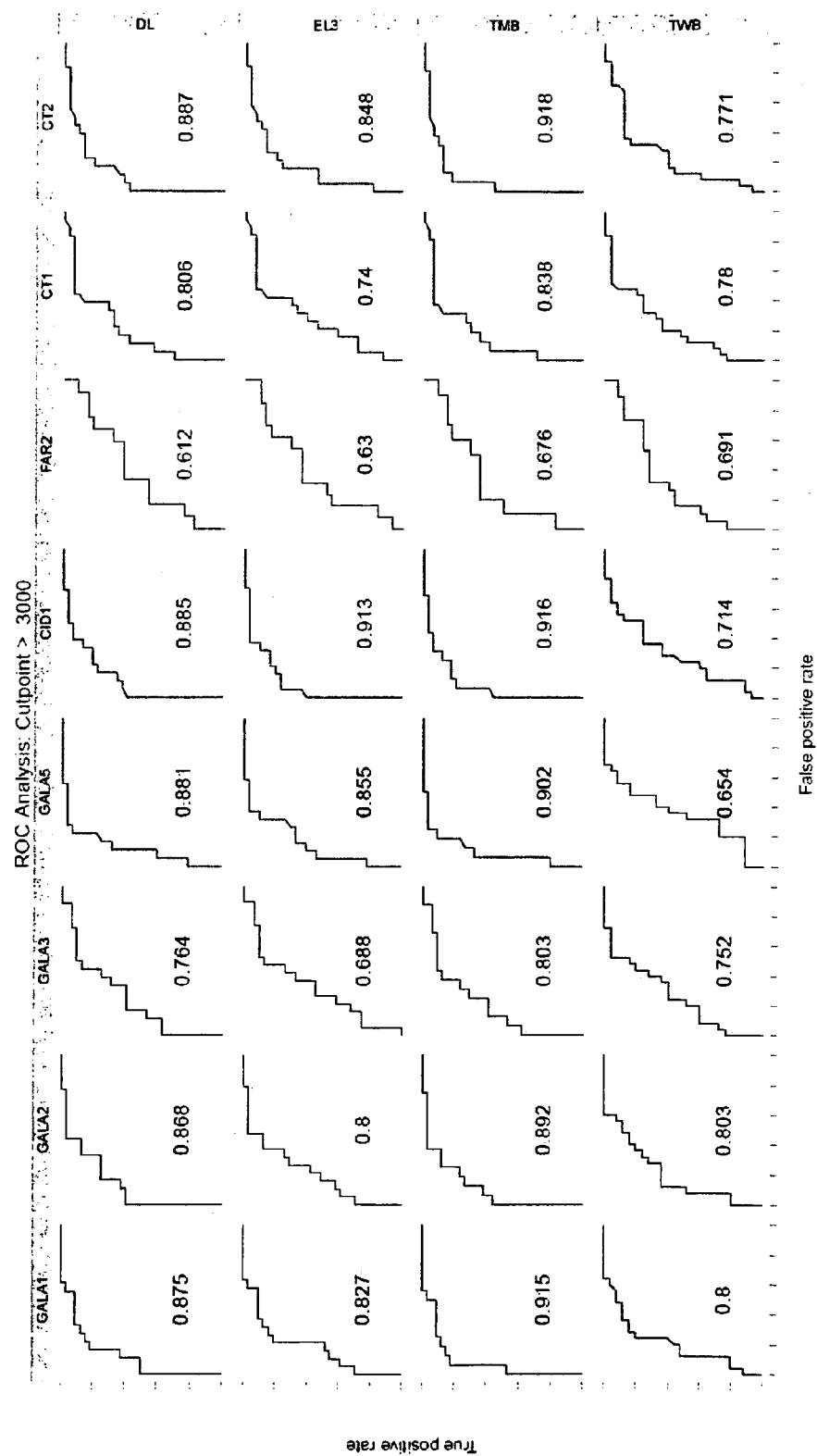
Figure 8B:
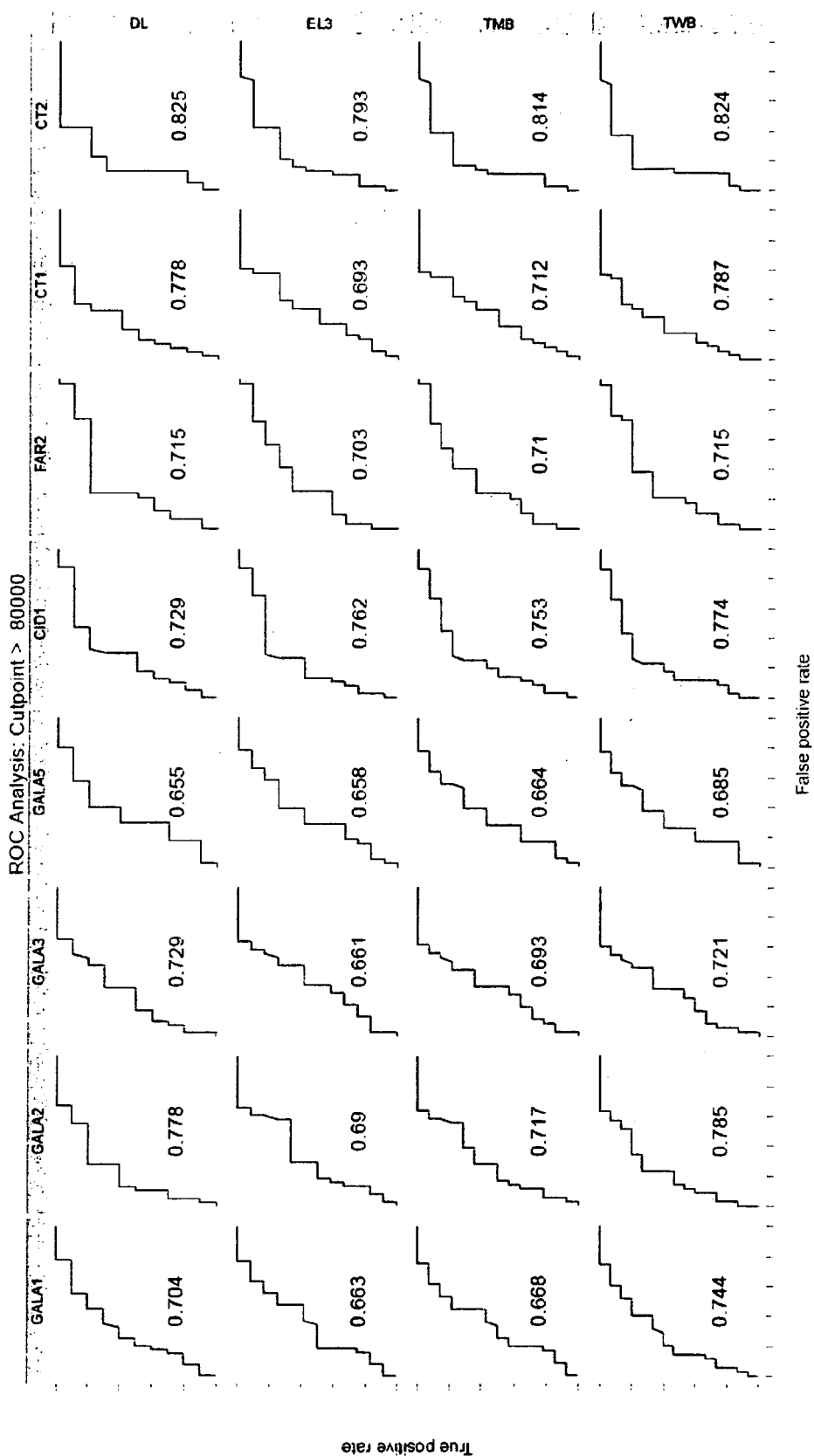
Figure 8C:
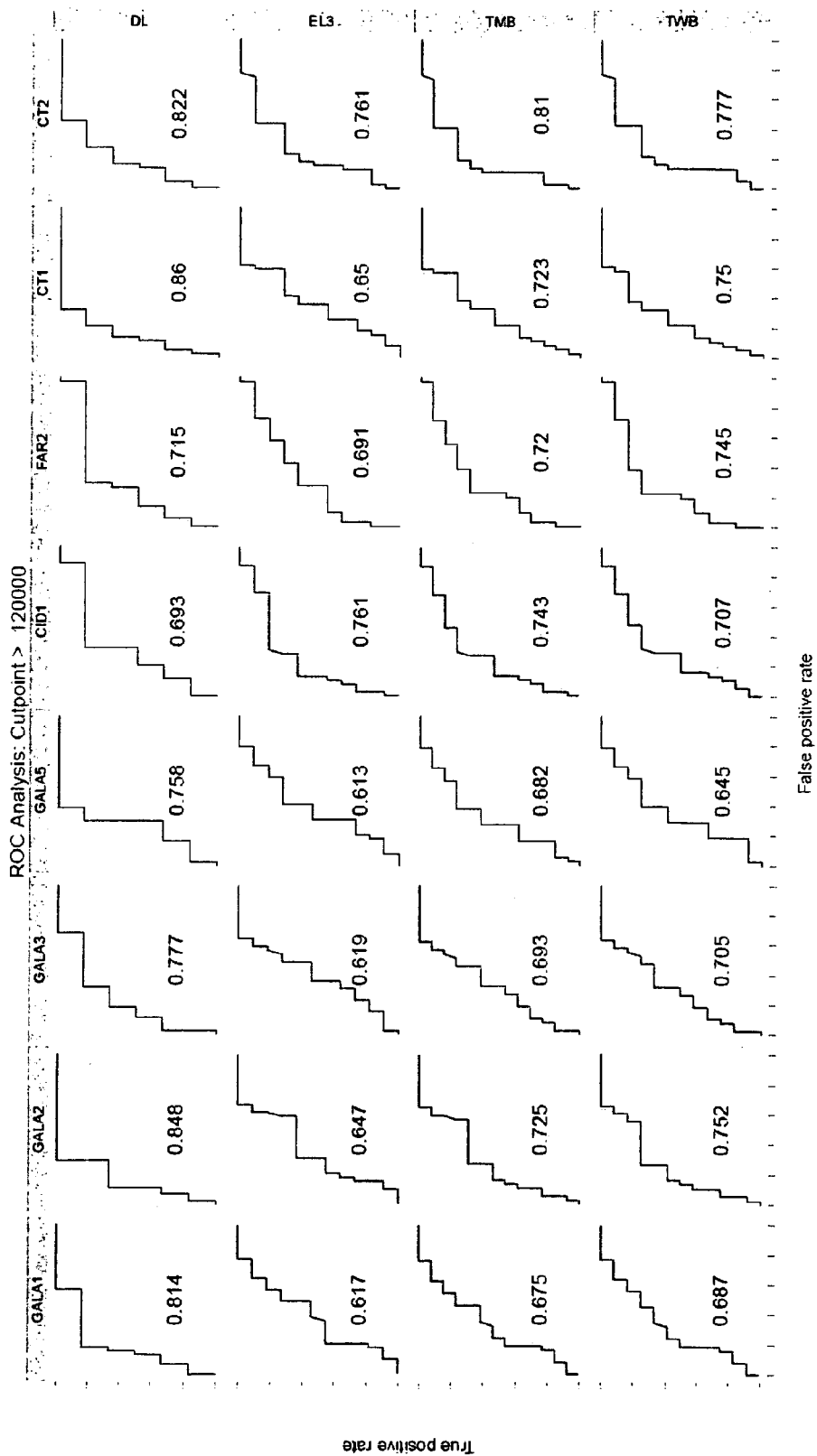
Figure 8D:
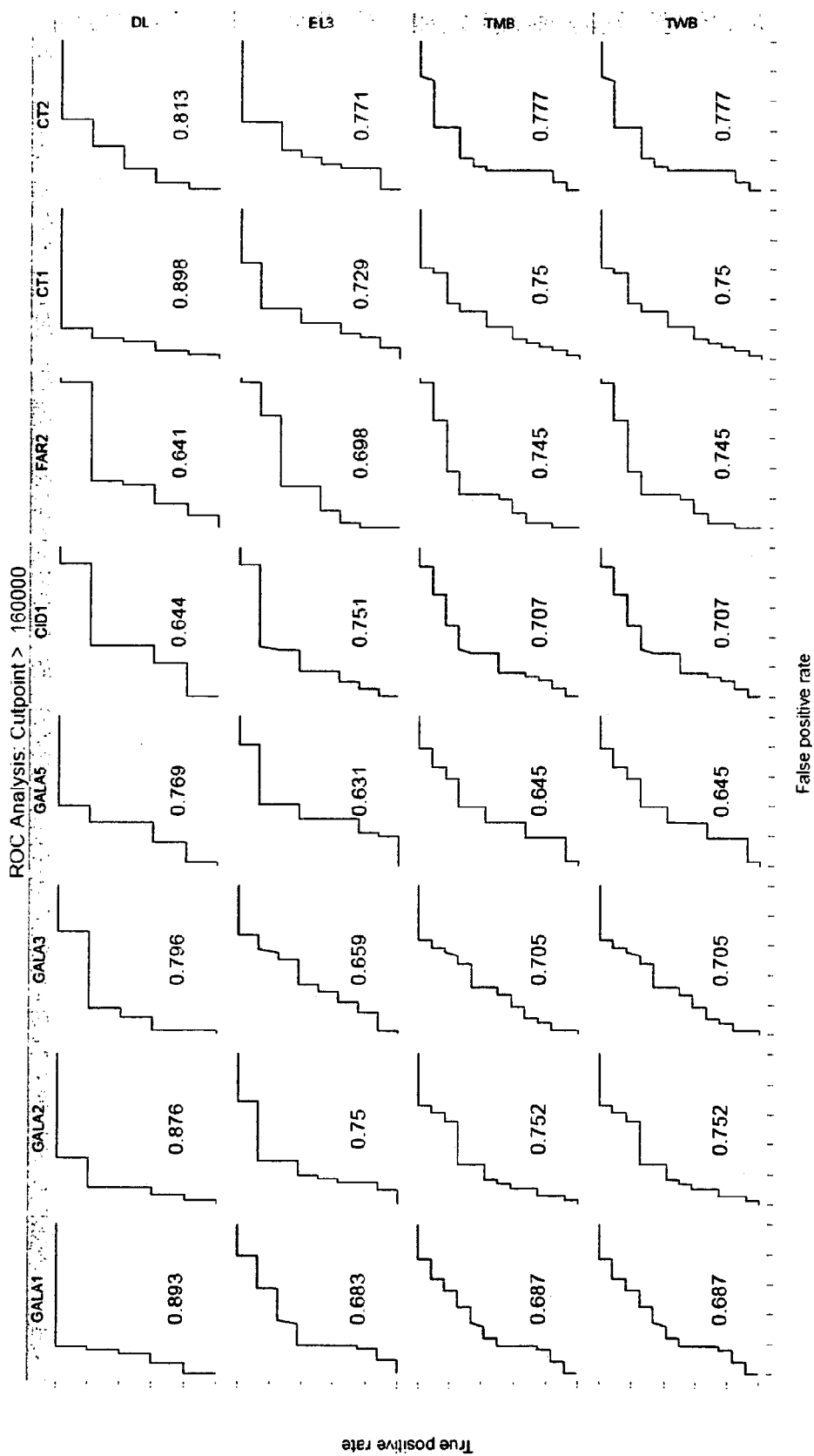
Figure 8E:
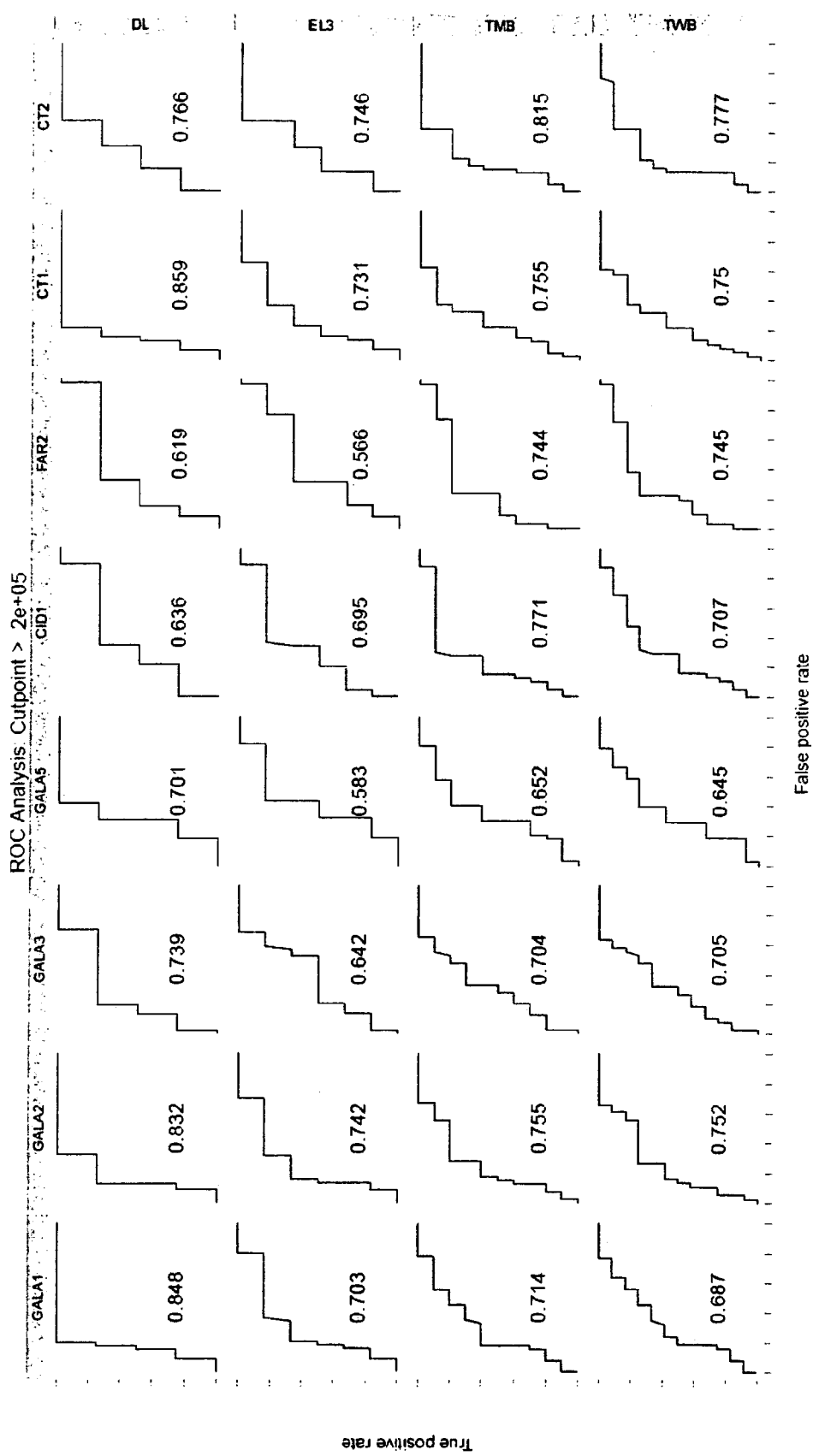

FIG. 6: Schematic representation of Cy-gala-1 and the 220 bp fragment of the gene amplified from 10 *cyathostomin* species. Cy-gala-1 cDNA sequence is represented by black boxes (A). The 220 bp region PCR amplified from genomic DNA samples from 10 *cyathostomin* species is represented by the white box. The latter is expanded to indicate the position of the intron (hatched box). The range in interspecies variation for the whole gene fragment (and also without the intron sequence) are depicted. A representative PCR product of Cy-gala-1 is shown for each species (B): *C. catinatum* (1); *C. nassatus* (2); *C. goldi* (3); *C. longibursatus* (4); *C. coronatum* (5); *C. pateratum* (6); *C. ashworthi* (7); *C. leptosomum* (8); *C. minutus* (9) and *C. labiatus* (10).

FIG. 7 A: Optimisation of antigen cocktails. The antibody response of encysted *cyathostomin* infected (positive) and non-infected (negative) animals is shown for varying concentrations of antigen and two different cocktails of antigen (CT1 and CT2). CT1 contains Gala 1, Gala 2, Gala 3. CT2 contains Gala 1, Gala 2, Gala 3 and CID 1. Individual antigen concentration is shown on the x axis and optical density (O.D) on the y axis. 7B: Ratio of signal for encysted *cyathostomin* infected (positive) to uninfected (negative) animals in an ELISA. Individual antigen concentration is on the x axis and ratio of positive to negative optical density on the y axis. C: shows mean serum antibody response to cocktail 1 (CT1) in groups of horses with varying infection levels. CT1 contains Gala 1, Gala 2, Gala 3. Horses were grouped as follows according to total mucosal parasite burden (TMB). Neg; uninfected horses TMB=0 (n=5), Low; TMB=0-20000, (n=8), Medium; TMB=20000-100000, (n=7), High; TMB=>100000 (n=26). Error bars show+/−standard error of the mean. O.D=optical density. D: shows mean serum antibody response to cocktail 2 (CT2) in groups of horses with varying infection levels. CT2 contains Gala 1, Gala 2, Gala 3 and CID 1. Horses were grouped as follows according to total mucosal parasite burden (TMB). Negative; uninfected horses TMB=0 (n=5), Low; TMB=0-20000, (n=8), Medium; TMB=20000-100000, (n=7), High; TMB=>100000 (n=26). Error bars show+/−standard error of the mean. O.D=optical density.

FIG. 8A-E: ROC analysis of ELISA data derived from cocktail (CT) 1 (which includes GALA-1, 2 and -3) and CT2 (which includes GALA-1, -2, -3 and CID-1). The Areas Under the Curve (AUC) are shown on each graph for each CT at the specified *cyathostomin* burden cut-off value indicated on each set of charts. The results indicate that CT1 and CT2 allow clear discrimination at different levels of *cyathostomin* mucusal burden, especially developing larval (DL) burdens above 120,000; however, it is likely that the AUC values could be improved by developing the assay to take into account *cyathostomin* species complexity and by including proteins that specifically relate to EL3. These additional proteins have been identified and will be added systematically to the cocktails to test their effect on AUC in the ROC analysis.'

MATERIALS AND METHODS

Parasite Material

Cyathostomins were collected from equine large intestinal tissue as described previously [9]. Briefly, caecum and ventral colon samples were removed at an abattoir and luminal parasites (LP), consisting of fifth stage larvae and adults, were collected from intestinal washings using sieves. Mucosal larval stages were recovered by pepsin-HCl digestion [9]. The mucosal parasites were separated into two populations based on size following previous recommendations [13]: (i) EL3 and (ii) late third stage (LL3)/developing fourth stage (DL4), collectively termed developing larvae (DL). Nematode samples for RNA extraction were placed into RNAlater (Ambion) at 4° C., while those for protein extraction and genomic DNA isolation were snap frozen in liquid nitrogen and stored at −80° C. For immunolocalisation experiments, DL were fixed in 10% formal saline. Infective third-stage larvae (IL3) were collected from horse faeces as described previously [8]. Individual adult cyathostomins were identified to species according to published recommendations [16]. Adult stage large strongyles, *Anoplocephala perfoliata* and *Parascaris equorum*, were also obtained and stored at −80° C.

Construction of a Complementary (c)DNA Library and Immunoscreening

Cyathostomin RNA was extracted from DL populations by homogenisation in a mortar and pestle under liquid nitrogen, then using TRIzol (Invitrogen) according to the manufacturer's instructions. Integrity of RNA samples was assessed using a 2100 Bioanalyser (Agilent Technologies) and RNA stored in RNase-free water at −80° C. A mixed-species DL cDNA library was constructed using a SMART cDNA Library Construction Kit (Clontech Laboratories, Inc) using long distance PCR according to manufacturer's instructions. Briefly, the cDNA was synthesised by reverse transcriptase (RT)-PCR using 1 µg total RNA pooled from 11 separate DL RNA samples collected over a 6-month period from a range of intestinal sites. This was done to maximise cyathostomin species representation within the cDNA library. After ligation into the λTriplEx2 vector, the cDNA was packaged into Gigapack Gold III packaging extract (Stratagene) and amplified in *Escherichia coli* XL1-Blue strain, (Stratagene). Library quality was assessed by analysing insert size in 40 plaques chosen at random. Length and identity of the inserts were determined by PCR and sequencing; the majority of plaques contained an insert with an average size of 500 base pairs (bp).

An EL3 cDNA library was constructed using the same method as for the construction of the DL cDNA library with the exception being the use of a SL1 primer to amplify nematode specific DNA prior to ligation into the TriplEx2 vector. (Martin, et al, 1995). Briefly, the cDNA was synthesised by reverse transcriptase (RT)-PCR using 1 µg total RNA pooled from EL RNA samples from EL3 larvae collected from a range of intestinal sites from 6 individual horses. This cDNA was then used in a PCR with SL1 forward primer sequence: GGTTTAATTACCCAAGTTTGAG (SEQ ID NO: 59) and reverse primer sequences: ATTCTAGAGGCCGAGGC (SEQ ID NO: 60) and TTCTAGAGGCCGAGGCG (SEQ ID NO: 61). Products of this PCR were then used for packaging into the TriplEx2 vector as described for generation of the DL cDNA library.

Immunoscreening was performed according to the manufacturer's protocol. For immunoscreening, two types of sera were used: cyathostomin-infected (CI) and helminth-free (HF) sera [29]. Ponies in the CI group (n=3) had been trickle infected with a total of 3.9 million cyathostomin IL3 over a period of 9 weeks, while the HF control group (n=3) were maintained helminth-free. Serum was obtained weekly from both groups. For immunoscreening, a pool of CI sera was prepared by combining samples obtained from the three ponies at 12, 13, 14 and 16 weeks PI. The pool of HF sera was made by combining samples obtained from the three ponies at 2, 3, 4 and 6 weeks before the start of the infection period. To reduce background reactivity, both pools of sera were pre-absorbed with *E. coli* lysate by incubating equal volumes of each and rocking for 4 h at room temperature [37]. After centrifugation at 18,000×g for 10 min, the supernatant was retained for probing library filter lifts. The primary immunoscreen consisted of approximately 108,000 cDNA clones in *E. coli* XL1-Blue strain. Plaque lifts were made onto nitrocellulose filters (Hybond-C Extra, GE Healthcare). The membranes were washed [five×10 min in Tris-buffered saline (10 mM Tris, 150 mM NaCl, pH 7.4) containing 0.05% Tween-20 (TBST)], then blocked for 1 h with 1% gelatin/TBST. In the first screen, the serum pool from the CI ponies was used at 1:200 in TBST and incubated with the membranes overnight at 4° C. The secondary antibody (goat anti-equine IgG(T), Serotec) and tertiary antibody (rabbit anti-goat[IgG]:HRP, Sigma), were incubated at 1:200 and 1:500 respectively, for 1 h each, with washing (as above) between steps. Filters were developed using SIGMAFAST DAB with Metal Enhancer (Sigma). Positive clones were isolated by taking agar plugs from the corresponding plate. Plaques that reacted non-specifically with equine sera (false positives) were identified by performing a second screen. Here, clones selected in the first round were screened as described above, except that filters were cut in half and one half probed with the CI serum pool and the other with the HF serum pool. Only plaques that reacted with the CI serum pool and not the HF serum pool were selected for sequence analysis. Vector-specific primers were used to amplify selected phage inserts and the PCR products purified using a QIAquick PCR Purification Kit (Qiagen). Each purified PCR product was sequenced using a commercial service (MWG Biotech). The resultant sequences were translated and searched against the GenBank 'non-redundant protein' database using BLASTp, and then against the 'non-human, non-mouse' EST database using tBLASTn, from the National Centre for Biotechnology Information [3]. Sequence alignments were performed using ClustalW2 [21] from the European Bioinformatics Institute (http://www.ebi.ac.uk/Tools/clustalw2/) and analysis for signal peptides performed using SignalP 3.0 [5]. Sequence identities were calculated using MegAlign 8.0.2 (DNASTAR) based on ClustalW alignments. Molecular mass estimations were made using an online tool from the Sequence Manipulation Suite (http://www.bioinformatics.org/sms2/protein_mw.html) and glycosylation sites identified using ExPASy Pro site (http://ca.expasy.org/prosite/).

RT-PCR to Determine Temporal Transcription Pattern of the mRNA Encoding the *Cyathostomin* Gut-Associated Larval Antigen-1 (Cy-GALA-1)

Stage-specific cDNA was synthesised from 1 µg each of EL3, DL and LP total RNA using a SMART cDNA Library Construction Kit (Clontech Laboratories, Inc.). Briefly, first-strand cDNA was synthesised and amplified using the long-distance PCR method (22 cycles). Double-stranded cDNA was purified using a QIAquick PCR Purification Kit (Qiagen), eluted in 50 µl dH$_2$O and stored at −20° C. until required. Integrity and loading of each cDNA population was assessed by amplifying a portion of the cytochrome oxidase c subunit I (coxI) gene using primers designed to conserved sequences among cyathostomins (sense: 5'-AAAAAGGAG-GTGTTTGGTTC-3' (SEQ ID NO: 62); antisense: 5'-CT-TGAATTTGATAAAACTACACC-3' (SEQ ID NO: 63)). PCR conditions were as follows: 0.3 μM primers, 0.25 μM dNTPs and 1.5 mM MgCl$_2$ with the following cycling: 94° C. for 5 min, 40 cycles at 94° C. for 30 sec, 60° C. for 30 sec and 72° C. for 30 sec, with a final extension at 72° C. for 7 min. PCR was performed using Platinum Taq (Invitrogen) with 1 μl cDNA from each developmental stage. Primers were designed for the most abundant immunoreactive clone identified in Section 2.2 and designated cyathostomin gut-associated larval antigen-1 (Cy-GALA-1). The primer sequences were as follows: sense, 5'-AATTGTGGGGAACAGGAG-3' (SEQ ID NO: 64); antisense, 5'-AATGAAAATCAGACTC-CTAGG-3' (SEQ ID NO: 65). PCR conditions were as above, but using 35 cycles. This experiment was repeated twice and the PCR products were analysed on 2% w/v agarose gels using TrackIt 100 bp DNA Ladder (Invitrogen) for size determination. The gels were stained with 1×GelRed (Biotium).

Expression of Recombinant Cy-GALA-1

The Cy-GALA-1 clone from the library immunoscreen that contained the largest insert was chosen for expression of recombinant protein. This clone incorporated the full-length coding sequence of Cy-gala-1 including the putative initiating methionine, signal peptide and poly-A tail. Primers were designed to amplify the coding sequence of Cy-gala-1 (minus the sequence that encoded the signal peptide) for sub-cloning into pET-22b(+) vector (Novagen). Appropriate sequences encoding flanking restriction enzyme sites were incorporated for uni-directional cloning. The primer sequences were as follows (NB: BamH1 and HindIII sites underlined): sense 5'-AATTCGGATCCGCAAGGTGTCATGGACCTTTTG-3' (SEQ ID NO: 66); antisense, 5'-CCGCAAGCT-TATATCTTTCATCTGTGTTGAGTCCAAAC-3' (SEQ ID NO: 67). The PCR step was performed as described above except that the annealing temperature was 58° C. and 30 cycles were used. The PCR product was purified as described above. The pET-22b(+) vector and PCR product were digested with BamH1 and HindIII and ligation, using a 1:1 ratio of vector to PCR product, performed according to Novagen's protocol. Plasmids were transformed into E. coli JM109 Competent Cells (Promega) following manufacturer's instructions and selected on ampicillin-agar. A selection of colonies was subjected to colony PCR to ensure the presence of the cDNA encoding Cy-GALA-1. A colony which contained an insert of the correct estimated size was subjected to plasmid purification using a Wizard Plus SV Miniprep kit (Promega) and the purified plasmid was both sequenced and transformed into E. coli BL21-CodonPlus (DE3)-RIL competent cells (Stratagene) for expression of recombinant protein (rCy-GALA-1). Following induction with 1 mM isopropyl-beta-D-thiogalactopyranoside (Bioline), soluble rCy-GALA-1, present in the bacterial lysate supernatant, was purified on a His-trap HP column (GE Healthcare), following manufacturer's instructions. The purified protein was dialysed into phosphate buffered saline, pH 7.4 (PBS), using cellulose dialysis tubing (Sigma) and stored at −20° C. until required. Purified rCy-GALA-1 (0.5 μg) was separated by SDS-PAGE, and a band at the expected size excised and subjected to matrix-assisted laser desorption/ionization time-of-flight (MALDI-ToF-ToF) mass spectrometry using an Ultraflex II MALDI-ToF-ToF mass spectrometer (Bruker Daltonics). The identity of the protein was confirmed by comparing the peptide mass fingerprint (PMF) generated to the theoretical peptide mass fingerprint (PMF) of Cy-GALA-1.

Preparation of rCy-GALA-1 Antiserum in Rabbits

Anti-rCy-GALA-1 antiserum was generated by injecting a rabbit with 50 μg of rCy-GALA-1, in 0.5 mg/ml QuilA/PBS (1 ml total injection). A secondary injection was administered three weeks later, after which a test bleed indicated a specific antibody response to the recombinant antigen. This experiment was performed under the legislation of a UK Home Office Licence.

Immunoblotting

Soluble somatic antigen extracts were prepared from cyathostomin stages (IL3, EL3, DL and LP) and adult worms of other helminth species (A. perfoliata, Strongylus equinus, Strongylus edentatus, Strongylus vulgaris and P. equorum) as described previously [9]. However, IL3 were disrupted using a Ribolyser Fast Prep FP120 (Thermo Scientific) instead of a glass homogeniser. Proteins were separated on 4-12% polyacrylamide Bis-Tris gels (NuPAGE MES system, Invitrogen) according to the manufacturer's protocol. For immunoblotting, proteins were transferred to nitrocellulose membranes. To assess cross-reactivity, 0.1 μg rCy-GALA-1 was loaded onto lanes of a 15-well 12% NuPAGE gel using SeeBlue Plus2 protein standards (Invitrogen) for molecular weight estimations. In one lane, 0.4 μg was loaded and after electrophoresis was cut from the gel and stained with Coomassie blue. After transfer, the blot was sliced into separate lanes and blocked in TNTT (10 mM Tris, 0.5M NaCl, 0.05% Tween-20, 0.01% thimerosal, pH 7.4). Each of the following sera was used, diluted 1:200 in TNTT: CI and HF sera pools (described above); a pool of 5 horses found to be cyathostomin-free (CF) from a local abattoir and a pool of 12 horses (from the same abattoir) with mucosal cyathostomin burdens of >100,000 (endemic infected—EI); horses mono-specifically infected with S. edentatus or S. vulgaris [20], P. equorum or Strongylus westeri [11]. Also tested was rabbit antiserum (and pre-immunisation samples) generated to the native 20 kDa cyathostomin complex [11]. Sera were incubated at room temperature for 1.5 h. Washing consisted of three, 5 min incubations in TNTT. The secondary and tertiary steps were as described for the immunoscreening (above), with the exception that the anti-20 kDa antiserum blots were incubated with goat anti-rabbit Ig:HRP (Dako) at 1:500. The blots were developed as for the library screen.

For detection of Cy-GALA-1 protein in somatic extracts of cyathostomins and other helminth species, somatic extracts (9 μg each antigen) were loaded onto 10-well, 4-12% NuPAGE gels, using 10 ng rCy-GALA-1 for comparison. After transfer to nitrocellulose, periodate treatment of the blots was performed as described previously [9]. The blots were probed with pre-immunisation rabbit serum and anti-rCy-GALA-1 serum at 1:300 in TNTT, followed by goat anti-rabbit(Ig):HRP (Dako) at 1:500, and developed as described above. Three 5 min washes were applied between steps.

Enzyme-Linked Immunosorbant Assay (ELISA)

To test reactivity of experimentally infected pony sera (CI) to rCy-GALA-1 over the course of infection, the following conditions were used. Each well of a Microlon High Binding plate (Greiner Bio-One) was coated with 100 μl of rCy-GALA-1 (1 μml$^{-1}$ in bicarbonate coating buffer, 0.1 M, pH 9.6) overnight at 4° C. Plates were washed with 0.05% Tween-20 in PBS (PBST), six times. Block solution (2% soya infant powder (w/v) in PBST) was added, 200 μl per well, and incubated for 1 h at 37° C. Plates were washed six times and CI and HF sera (1:200 in block solution), from weekly time points 2 weeks before infection to 16 weeks PI, added and incubated for 2 h at 37° C. After washing, 100 μl goat anti-equine IgG(T) were added, diluted 1:200 in blocking solution. After 1 h at 37° C. and washing, 100 μl rabbit anti-goat (Ig):HRP were added, diluted in block at 1:500, and incubated for 1 h at 37° C. To develop the reaction, Sigma-FAST OPD tablets (Sigma) were dissolved in $H_2O$ according to the manufacturer's instructions and 100 μl added to each well and incubated for 15 min. Fifty μl of 2.5 M $H_2SO_4$ were added to stop the reaction and the absorbance read at 490 nm. The same conditions were used to measure the anti-rCy-GALA-1 antiserum response to somatic extracts of *cyathostomin* stages and other adult helminth species extracts, except that these were coated at 2 μgml$^{-1}$. The antiserum and goat anti-rabbit:HRP were used at 1:500.

Immunolocalisation

*Cyathostomin* DL were fixed in 10% formal saline and immobilised in a solidified gelatin plug by mixing with molten 5% gelatin/PBS (<30° C.) and allowing to set. The plugs were then dehydrated with alcohol and xylene and embedded in paraffin wax. Sections were cut at 3 μm using a microtome and the slides stored at 4° C. Immunolocalisation was performed using an EnVision+ System-HRP for rabbit primary antibodies (DakoCytomation) in a Sequenza Slide Rack (Thermo Scientific) at room temperature. After de-waxing, the slides were incubated in 0.5% Tween-80/PBS (PBST80) with 0.3% $H_2O_2$ for 20 min, to inactivate endogenous peroxidises. Blocking was performed using 100 μl 25% normal goat serum (NGS) in PBST80 for 1 h. Rabbit antisera obtained prior to and after two immunisations with rCy-GALA-1 were diluted 1:100 in 10% NGS/PBST80, and 100 μl incubated on the slides for 1 h. After two washes in PBS at room temperature, 100 μl of HRP-labelled polymer conjugated to goat anti-rabbit Ig, was incubated (neat) for 30 min. The reactions were developed in neat 3-amino-9-ethylcarbazole substrate chromogen for 7.5 min. Slides were washed in $H_2O$ and counterstained using haematoxylin.

Single Worm PCR to Identify the Gene Encoding GALA in Different *Cyathostomin* Species Genomic DNA was isolated from 54 individually identified adult cyathostomins using the DNeasy Blood and Tissue kit (Qiagen) according to their protocol, but with the addition of a homogenisation step before the proteinase K digestion step; each individual was disrupted briefly using a 1.5 ml microfuge tube homogeniser in 50 μl ATL buffer supplied with the kit. The following 10 species were examined (NB: numbers of worms used for each species is shown in parenthesis): *Cyathostomum catinatum* (10), *Cylicostephanus goldi* (8), *Coronocyclus coronatus* (6), *Cyathostomum pateratum* (6), *Cylicocyclus nassatus* (6), *Cylicostephanus longibursatus* (5), *Cylicocyclus ashworthi* (4), *Cylicocyclus leptostomum* (3), *Coronocyclus labiatus* (1) and *Cylicostephanus minutus* (1). The same primers used in Section 2.3 for RT-PCR were used to amplify a conserved fragment of Cy-gala in each species. The cycling conditions were: 2 min at 94° C., followed by 40 cycles of 15 sec at 94° C., 30 sec at 58° C. and 60 sec at 72° C., and a final extension at 72° C. for 7 min. PCR products were analysed on agarose gels as described above and PCR products from each of the 54 individuals cloned into pGEMT-Easy (Promega) according to manufacturer's instructions. Each clone was sequenced in forward and reverse directions with vector-specific primers using the commercial sequence facility described above.

Results

Immunoscreening of the *Cyathostomin* DL cDNA Library and Sequence Analysis of Cy-Gala-1

The primary immunoscreening yielded 33 positive clones; five of which were excluded as false positives on the basis of the secondary screen using HF sera. The remaining 28 clones contained inserts ranging in size from approximately 500 to 1500 bp. Sequence analysis indicated that 15 of these showed high identity to one another (73-100% at the amino acid [aa] level). One of these (Cy-gala-1) represented a full-length coding sequence: i.e. it contained a putative initiation codon, signal peptide and termination codon upstream of a poly-A tail. The entire coding sequence was 223 aa which, after cleavage of the signal peptide, would result in a 206 aa mature protein estimated at 25.6 kDa. Cy-GALA-1 contains a highly conserved domain as revealed by a domain search via BLASTp analysis [28]. The function of this domain is unknown and in *Caenorhabditis elegans* is designated Domain of Unknown Function 148 (DUF148). The Cy-GALA-1 sequence displayed highest aa identity to a sequence from *Nippostrongylus brasiliensis* (accession number: BAB68205; 35% identity over 128 residues), also identified via immunoscreening [38]. Two predicted proteins from *C. elegans* showed 34% identity over 105 residues to Cy-GALA-1. These proteins were 44.5% identical to each other. Also identified, were two trichostrongyloid ESTs: one from *Teladorsagia circumcincta* L3 (accession number: AAM45145), which displayed 32% identity to Cy-GALA-1 over 102 aa, and one from Ostertagia osteragi adult worms (accession number: CAD22110) with showed 32% identity over 140 aa. The two *C. elegans* orthologues (referred to here as Ce-KLP-1 (NP_502026) and Ce-KLP-2 (NP_501448)) contain glycine-rich domains which gives them homology to keratin sequences and hence their designation as 'keratin-like' proteins (KLP). All the parasitic nematode sequences described here lack this glycine rich sequence, despite some being previously designated as 'KLP-like' proteins [38]. Rather than classifying Cy-GALA-1 as a KLP, it was instead named to reflect its localisation to the gut (see below). An alignment of Cy-GALA-1 with its orthologous sequences in *N. brasiliensis* and *C. elegans* is depicted in FIG. 1. In all the parasitic nematode sequences, except that of *T. circumcincta*, a histidine-rich motif precedes DUF148 (FIG. 1); its function is unknown. In addition, four potential N-linked glycosylation sites were identified. Searching Cy-GALA-1 at Nembase gave additional significant hits. All of these EST sequences contained regions with high identity to DUF148 and some had glycine-rich regions. The closest matches were to sequences identified in adult *Ancylostoma ceylanicum* (accession numbers: CB176510, CB190303 and CB339159), with 45-46% aa identity to Cy-GALA-1 over 110 residues.

Temporal Transcription Pattern of Cy-Gala-1

Cy-gala-1 transcript was detected in DL and EL3 cDNA and not in cDNA from LP parasites (FIG. 2). After 40 cycles, similar levels of coxI PCR product were observed in DL and LP cDNA. However, a coxI PCR product from EL3 was less intense, indicating low quality of EL3 cDNA. This was due to degradation of EL3 RNA caused by the extensive digestion method required to harvest these larvae. These results indicate the apparent specificity of this transcript for mucosal stages; hence the gene was selected for expression of recombinant protein for assessment as a diagnostic marker.

Expression of rCy-GALA-1 and its Immunoreactivity rCy-GALA-1 was obtained from the soluble fraction of the *E. coli* lysate; the purified protein was approximately 28 kDa (FIG. 3). The identity of this protein as rCy-GALA-1 was confirmed by MALDI-ToF-ToF (data not shown). Its molecular weight was slightly higher than the expected size of native Cy-GALA, calculated to be 25.6 kDa, and was due to addition of the His-tag and *E. coli* signal peptide. Anti-rCy-GALA-1 antiserum predominantly recognised the expected size band in somatic DL extracts (Section 3.4 and FIG. 4). The immunoreactivity of the recombinant antigen is shown in FIG. 3. Only IgG(T) in CI and EI sera equine sera bound rCy-GALA- 1, indicating that both experimentally and naturally infected horses recognise this antigen. Sera from horses harbouring other parasitic helminths did not contain IgG(T) that bound Cy-GALA-1. The rabbit antiserum to the *cyathostomin* larval anti-20 kDa complex generated previously [11], showed strong reactivity to rCy-GALA-1.

Levels of rCy-GALA-1-specific IgG(T) in sera from infected vs. non-infected ponies [29] were measured by ELISA (FIG. 3). Increases in rCy-GALA-1-specific IgG(T) levels were observed in all infected ponies by 6 weeks PI. A more rapid increase was observed in pony 104. Antigen-specific IgG(T) levels plateaued at 8 weeks PI for 104 and 12 weeks PI for 101 and 105; these levels remained elevated until the end of the measurement period at 16 weeks PI. No significant increases in rCy-GALA-1-specific IgG(T) levels were observed in any of the HF ponies throughout the experiment. Murphy and Love (1997) [29] described clinical signs in the infected animals from 4-6 weeks PI. While all showed a slower increase in percentage weight gain than the control group, pony 104 showed a drop in weight gain over weeks 4-8 PI. These signs may indicate a higher level of infection in 104. Anti-rCy-GALA-1 antiserum reactivity was tested against somatic extracts from *A. perfoliata, P. equorum, S. edentatus, S. vulgaris* and *S. equorum* [FIG. 4]. No reactivity was observed except to a band at 38 kDa in the *P. equorum* extract. Binding to this band was less than that seen in the *cyathostomin* DL lane (FIG. 4).

Detection of Cy-GALA-1 in Different *Cyathostomin* Stages

Antiserum raised to rCy-GALA-1 was used to investigate the presence of the native protein in different *cyathostomin* stages (FIG. 4). This antiserum bound the 28 kDa recombinant antigen (FIG. 4, lane 1): an additional band at 53 kDa was bound and may represent a dimeric form of Cy-GALA-1. The anti-rCy-GALA-1 antisera showed reactivity to EL3 and DL somatic extracts but not to adult extract (FIG. 4). Immunoreactivity to antigens in EL3 and DL stages was primarily directed at molecules of approximately 26 kDa, corresponding to the calculated molecular mass of Cy-GALA-1. Two other EL3 and DL antigens were bound by IgG in anti-Cy-GALA-1 antisera, one at approximately 45 kDa and the other at 55 kDa. The ELISA results indicated high reactivity to DL, however no binding was observed in EL3 or adult extract.

Immunolocalisation of Cy-GALA-1

DL were subjected to immunolocalisation studies (FIG. 5). Reactivity was detected in the gut of individual worms, where considerable staining was observed on the gut epithelium and in the gut lumen. No reactivity was detected to any other structures in the nematodes.

Single Worm PCR to Identify the Gene Encoding Cy-GALA in Different *Cyathostomin* Species Single worm PCR experiments were performed using primers to amplify a 220 bp fragment of Cy-gala-1 from 50 morphologically-identified adult worms encompassing 10 species. A PCR product was obtained from all nematodes tested and sequencing confirmed that PCR products representative of each species encoded Cy-gala sequence. FIG. 6 shows a schematic representation of this fragment and PCR products from each species. There was variation in size of the PCR product obtained from different species; from 267 bp (for all *C. coronatus* individuals) to 284 bp (for one *C. goldi* individual). This variation was due to a difference in intron size at this site amongst the species. The precise location of the intron was conserved as indicated by splice site analysis (FIG. 6). Nucleotide identities between individuals from different species ranged from 78.9-99.1% for the whole fragment. Higher nucleotide identities were observed in the coding region; interspecies variation ranged from 82.2-98.9% over 180 nt, while the amino acid identities were 80-100% over 60 residues. At the aa level, intra-species variation was as follows: *C. catinatum* 93.3-100%; *Cs. goldi* 90.0-100.0%; *Co. coronatus* 96.7-100.0%; *C. pateratum* 93.3-100%; *Cc. nassatus* 88.3-98.3%; *Cs. longibursatus* 91.7-100%; *Cc. ashworthi* 90.0-100.0%; *Cc. leptostomum* 88.3-100.0%. In an attempt to assign a species for the library clone, Cy-gala-1, the coding sequence from each individual was compared against Cy-gala-1 in this 220 bp fragment. The highest identity was found to a *C. pateratum* individual (97.8% nt identity and 98.3% aa identity). Therefore, with the available sequence data for each species, we have provisionally identified Cy-gala-1 as belonging to *C. pateratum*.

Optimisation of Antigen Cocktails.

The optimum concentration of antigen to use in an ELISA using a cocktail of antigens was evaluated using sera from *cyathostomin* infected (positive) and non-infected (negative) animals. FIG. 7A shows the serum antibody response to varying concentrations of antigen in two different cocktails of antigen (CT1 and CT2). CT1 contains GALA-1, -Gala 2 and -3. CT2 contains these three antigens plus CID1. Individual antigen concentration is shown on the x-axis and optical density (O.D) on the y-axis. FIG. 7B shows the ratio of the OD signal obtained om *cyathostomin* infected (positive) vs. uninfected (negative) animals in an ELISA. Individual antigen concentration is on the x-axis and ratio of positive to negative optical density on the y-axis.

Evaluation of Antigen Cocktail for Discriminating Different Levels of Infection.

Two different cocktails of antigen were tested in an ELISA to assess their potential for discriminating different levels of mucosal infection. FIGS. 7 C and D shows mean serum antibody response to cocktail 1 (CT1) and cocktail 2 (CT2) respectively in groups of horses with varying infection levels. CT1 and CT2 were as described above. Horses were grouped as follows according to total mucosal parasite burden (TMB). Neg; uninfected horses TMB=0 (n=5), Low; TMB=0-20000, (n=8), Medium; TMB=20000-100000, (n=7), High; TMB=>100000 (n=26). Error bars show+/−standard error of the mean. O.D=optical density.

Discussion

Identification of the *cyathostomin* GALA sequence is an advance in the development of an ELISA for the diagnosis of larval cyathostominosis. Three important criteria were met by this protein: 1) it appeared to be specific to larval stages; 2) there was no cross reactivity with the other equine helminth species assessed here and 3) the gene encoding the protein was isolated from all *cyathostomin* species examined with a relatively low level of sequence variation amongst the species. Furthermore, serum IgG(T) responses to rCy-GALA-1 increased within 5 weeks of the administration of an experimental infection and the protein was also the target of IgG(T) responses in naturally infected horses.

The RT-PCR, immunoblot and ELISA results indicated that Cy-GALA-1 is restricted to parasitic larval stages, particularly DL stages. This is a vital feature for a diagnostic marker that specifically indicates mucosal larval burden. Despite numerous attempts, RNA extracted from EL3 was of relatively poor quality so it was difficult to judge precise levels of transcription in these stages. EL3 require extensive digestion in pepsin/HCl at 37° C. to remove them in sufficient quantity from the intestinal mucosa and submucosa and so it is technically difficult to obtain sufficient high quality RNA. The EL3 somatic protein extracts also contained a small amount of contaminating host protein (it is impossible to totally separate every single worm from its host capsule), and this may have resulted in the lower levels of reactivity of EL3 extracts to Cy-GALA-1 antiserum as indicated by the ELISA results. Immunolocalisation was also attempted in EL3, but degradation resulted in a lack of distinct morphology and no specific binding was observed (data not shown). Therefore it remains to be fully elucidated if Cy-GALA is a significant immunogen of EL3, or is predominantly an antigen of the later larval stages. Immunolocalisation studies of diseased equine mucosa are planned, to provide EL3 embedded in their mucosal cysts. Serum IgG(T) responses to rCy-GALA-1 over the time course of an experimental infection showed that the antigen is a reasonably early indicator of infection and these responses were identified whilst the infections were not patent [29]. Indeed, in these ponies, the infections never progressed to patency even though the experiment was continued until 60 and 62 weeks PI in two of the animals. Substantial increases in reactivity were observed at 5 weeks PI in one animal (pony 104) and by 6 weeks in all ponies. *cyathostomin* larval-specific serum IgG(T) responses were analysed previously in these animals and similar dynamics of responses were observed to the 20 and 25 kDa complexes purified from EL3/DL mixtures [11]. Furthermore, serum IgG(T) reactivity to crude larval antigen was also observed to increase only after 6 weeks PI in these ponies [9], suggesting that only by this time point do larvae stimulate a detectable serum IgG(T) response. Pony 104 had the most pronounced increase in IgG(T) to rCy-GALA-1 and this is similar to its response to crude larval antigen and the purified 20- and 25-kDa antigen complexes [9, 11]. The clinical signs observed in this pony (reduced weight gain, lowest plasma fructosamine) indicate that it may have had a greater burden of mucosal larvae [29]. Indeed, when this animal was euthanized at 20 weeks PI it was found to have a high *cyathostomin* burden. Unfortunately the other two ponies in the group were necropsied at 60 and 62 weeks PI so their burdens cannot be directly compared with pony 104. Nevertheless, the data provides preliminary evidence that this recombinant antigen may be able to distinguish varying degrees of disease.

As mentioned above, there is similarity of the IgG(T) response to rCy-GALA-1 and to the two larval antigen complexes purified and shown to have diagnostic potential previously [10, 11]. The molecular mass of Cy-GALA, estimated at 25.6 kDa, means that it could feasibly be a component of the 25 kDa antigen complex, an observation supported by the results using anti-rCy-GALA-1 against EL and DL somatic extracts in western blots. Antiserum generated to the 20 kDa complex in rabbits also bound rCy-GALA-1 indicating its presence in this complex also. This is not altogether surprising as these complexes were excised rather crudely from SDS-polyacrylamide gels [10, 11].

Specificity of Cy-GALA-1 in the cyathostominae was confirmed by probing the recombinant protein with sera from horses infected mono-specifically with heterologous helminth species. While experimentally infected (CI) and naturally infected (EI) horses recognised rCy-GALA-1, IgG(T) in serum from horses with large strongyle infections (*S. edentatus, S. westeri* or *S. vulgaris*) and *P. equorum* infection, did not bind the antigen. Cross-reactivity was further explored by probing somatic extracts of other equine parasites with anti-rCy-GALA-1 serum: extracts from *A. perfoliata, P. equorum, S. edentatus, S. vulgaris* and *S. equorum* were analysed. In the ELISA no binding above background levels was observed in any of the five other parasite extracts. In the immunoblot, there was a degree of binding to a band of approximately 38 kDa in the *P. equorum* extract, but this was of far less intensity than binding observed in the *cyathostomin* DL samples. Furthermore, there was no cross reactivity to *P. equorum* antigens when the samples were assessed using the ELISA.

The presence of sequences encoding GALA-like proteins was confirmed in 10 *cyathostomin* species, indicating ubiquity of this gene in the group. There are currently 50 recognised *cyathostomin* species [23], and while a large number of species are often found in infected individuals [6,7], the bulk of the burden is consistently found to comprise 5-10 species [26, 27, 36]. Nine of the species explored in this study belong to the 10 most common cyathostomins as identified by Reinemeyer et al. (1984) [36], Ogbourne (1976) [30] and Lictenfels et al 2001 [22]. The presence of Cy-GALA in these species indicates it is likely to be present in most, if not all, cyathostomins. An analysis of the sequence of Cy-gala-1 amongst the cyathostomins indicated a low level of sequence diversity across the selected 220 bp region. It is possible that greater diversity exists outside this region and the full-length cDNA sequences of Cy-gala are currently being isolated from a number of species to investigate this further. Promisingly, for development of a specific immunoassay, the levels of sequence diversity identified thus far are substantially lower among cyathostomins than they are when the Cy-gala sequences are compared to orthologous sequences in other nematode species, i.e. 80-100% vs. 25-35% identity. The nematodes that were present in the CI pony group unfortunately had not been identified, so it is difficult to compare levels of rCy-GALA-1 IgG(T) with the species present.

A factor that must be considered in the development of any helminth immunodiagnostic assay is the length of time that circulating specific immunoglobulin levels take to return to normal values after anthelmintic treatment. Since the ponies used in the experimental infection were not treated with anthelmintic before necropsy, this could not be assessed here. Studies on a commercially-available serological ELISA for *A. perfoliata* [33, 34], which is based on the specific binding of IgG(T) to a purified 12/13 kDa antigen complex, indicated that post-treatment IgG(T) levels can take months to reduce to 'non-infection' levels [2,4]. Also, Kjaer et al. (2007) [18] found that two thirds of horses which had no visible signs of tapeworm infection at necropsy had ELISA ODs higher than the current accepted cut-off for infection (0.2). Despite this, the *A. perfoliata* 12/13 kDa antigen ELISA is still regarded as the most useful diagnostic tool for infection [1, 18]. These observations suggest that circulating IgG(T) levels may remain high for a time after treatment and this will be considered when designing how a *cyathostomin* diagnostic assay, based on IgG(T), could be used in future.

No function has been ascribed to orthologues of Cy-GALA in other nematode species and only Nb-KLP has been characterised in any detail [38]. It was speculated that Nb-KLP may be a cuticular protein, based on its identity to Ce-KLPs, which are described as 'keratin-like'. However the authors did not explore this further. Ce-KLP-1 and -2 encode hypothetical proteins, and some information regarding these is available in WormBase (www.wormbase.org). Both are predicted to be alpha-helical proteins, and Ce-KLP-1 has been confirmed by transcript evidence, while Ce-KLP-2 has been partially confirmed. Ce-KLP-1 shows no RNAi phenotype, while Ce-KLP-2 displays 'embryonic lethal', indicating that it may play a role in development. An anatomic expression plan is available for Ce-KLP-2, showing expression in pharyngeal muscles and tail neurons which is different to what was observed here with localisation of Cy-GALA to the worm intestinal lumen. The function of this molecule remains to be elucidated.

REFERENCES

[1] Abbott J. B., Barrett E. J., The problem of diagnosing tapeworm infections in horses, Equine Vet. J. (2008) 40:5-6.

[2] Abbott J. B., Mellor D. J., Barrett E. J., Proudman C. J., Love S., Serological changes observed in horses infected with *Anoplocephala perfoliata* after treatment with praziquantel and natural reinfection, Vet. Rec. (2008) 162:50-3.

[3] Altschul S. F., Gish W., Miller W., Myers E. W., Lipman D. J., Basic Local Alignment Search Tool, J. Mol. Biol. (1990) 215:403-410.

[4] Barrett E. J., Farlam J., Proudman C. J., Field trial of the efficacy of a combination of ivermectin and praziquantel in horses infected with roundworms and tapeworms, Vet. Rec. (2004) 154:323-325.

[5] Bendtsen J. D., Nielsen H., von Heijne G., Brunak S., Improved prediction of signal peptides: SignalP 3.0, J. Mol. Biol. (2004) 340:783-95.

[6] Bucknell D. G., Gasser R. B., Beveridge I., The prevalence and epidemiology of gastrointestinal parasites of horses in Victoria, Australia, Int. J. Parasitol. (1995) 25:711-24.

[7] Chapman M. R., Kearney M. T., Klei T. R., Equine cyathostome populations: accuracy of species composition estimations, Vet. Parasitol. (2003) 116:15-21.

[8] Clark H. J., Kaplan R. M., Matthews J. B., Hodgkinson J. E., Isolation and characterisation of a beta tubulin isotype 2 gene from two species of *cyathostomin*, Int. J. Parasitol. (2005) 35:349-58.

[9] Dowdall S. M., Matthews J. B., Mair T., Murphy D., Love S., Proudman C. J., Antigen-specific IgG(T) responses in natural and experimental cyathostominae infection in horses, Vet. Parasitol. (2002) 106:225-42.

[10] Dowdall S. M., Proudman C. J., Klei T. R., Mair T., Matthews J. B., Characterisation of IgG(T) serum antibody responses to two larval antigen complexes in horses naturally- or experimentally-infected with cyathostomins, Int. J. Parasitol. (2004) 34:101-8.

[11] Dowdall S. M., Proudman C. J., Love S., Klei T. R., Matthews J. B., Purification and analyses of the specificity of two putative diagnostic antigens for larval *cyathostomin* infection in horses, Res. Vet. Sci. (2003) 75:223-9.

[12] Eysker M., Boersema J. H., Kooyman F. N. J., The effect of ivermectin treatment against inhibited early 3rd stage, late 3rd stage and 4th stage sarvae and adult stages of the cyathostomes in Shetland ponies and spontaneous expulsion of these helminths, Vet. Parasitol. (1992) 42:295-302.

[13] Eysker M., Klei T. R., Mucosal larval recovery techniques of cyathostomes: can they be standardized?, Vet. Parasitol. (1999) 85:137-44.

[14] Geldhof P., Vercauteren I., Knox D., De Maere V., Van Zeveren A., Berx G., Vercruysse J., Protein disulphide isomerase of *Ostertagia ostertagi*: an excretory-secretory product of L4 and adult worms? Int. J. Parasitol. (2003) 33:129-36.

[15] Giles C. J., Urquhart K. A., Longstaffe J. A., Larval cyathostomiasis (immature trichonema-induced enteropathy): a report of 15 clinical cases, Equine Vet. J. (1985) 17:196-201.

[16] Hodgkinson J. E., Love S., Lichtenfels J. R., Palfreman S., Ramsey Y. H., Matthews J. B., Evaluation of the specificity of five oligoprobes for identification of *cyathostomin* species from horses, Int. J. Parasitol. (2001) 31:197-204.

[17] Kaplan R. M., Anthelmintic resistance in nematodes of horses, Vet. Res. (2002) 33:491-507.

[18] Kjaer L. N., Lungholt M. M., Nielsen M. K., Olsen S, N., Maddox-Hyttel C., Interpretation of serum antibody response to *Anoplocephala perfoliata* in relation to parasite burden and faecal egg count, Equine Vet. J. (2007) 39:529-33.

[19] Klei T. R., Chapman M. R., French D. D., Taylor H. W., Evaluation of ivermectin at an elevated dose against encysted equine cyathostome larvae, Vet. Parasitol. (1993) 47:99-106.

[20] Klei T. R., Torbert B. J., Chapman M. R., Ochoa R., Irradiated larval vaccination of ponies against *Strongylus vulgaris*, J. Parasitol. (1982) 68:561-9.

[21] Larkin M. A., Blackshields G., Brown N. P., Chema R., McGettigan P. A., McWilliam H., Valentin F., Wallace I. M., Wilm A., Lopez R., Thompson J. D., Gibson T. J., Higgins D. G., Clustal W and clustal X version 2.0, Bioinformatics (2007) 23:2947-8.

[22] Lichtenfels J. R., McDonnell A., Love S., Matthews J. B., Nematodes of the tribe Cyathostominea (Strongylidae) collected from horses in Scotland, Comp. Parasitol., (2001) 68:265-269.

[23] Lichtenfels J. R., Kharchenko V. A., Dvojnos G. M., Illustrated identification keys to strongylid parasites (Strongylidae: Nematoda) of horses, zebras and asses (Equidae), Vet. Parasitol. (2008) 156:4-161.

[24] Love S., Duncan J. L., The development of naturally acquired cyathostome infection in ponies, Vet. Parasitol. (1992) 44:127-42.

[25] Love S., Murphy D., Mellor D., Pathogenicity of cyathostome infection, Vet. Parasitol. (1999) 85:113-21.

[26] Lyons E. T., Tolliver S. C., Drudge J. H., Historical perspective of cyathostomes: prevalence, treatment and control programs, Vet. Parasitol. (1999) 85:97-111.

[27] Lyons E. T., Tolliver S. C., Drudge J. H., Stamper S., Swerczek T. W., Granstrom, D. E., A study (1977-1992) of population dynamics of endoparasites featuring benzimidazole-resistant small strongyles (Population S) in Shetland ponies, Vet. Parasitol. (1996) 66:75-86.

[28] Marchler-Bauer A., Anderson J. B., Derbyshire M. K., Weese-Scott C., Gonzales N. R., Gwadz M., Hao, L. N., He S. Q., Hurwitz D. I., Jackson J. D., Ke Z. X., Krylov D., Lanczycki C. J., Liebert C. A., Liu C. L., Lu F., Lu S. N., Marchler G. H., Mullokandov M., Song J. S., Thanki, N., Yamashita, R. A., Yin, J. J., Zhang, D. C., Bryant S. H., CDD: a conserved domain database for interactive domain family analysis, Nucleic Acids Res. (2007) 35:D237-D240.

[29] Murphy D., Love S., The pathogenic effects of experimental cyathostome infections in ponies, Vet. Parasitol. (1997) 70:99-110.

[30] Ogbourne C. P., The prevalence, relative abundance and site distribution of nematodes of the subfamily Cyathostominae in horses killed in Britain, J. Helminthol. (1976) 50:203-14.

[31] Paul J. W., Equine larval cyathostomosis, Comp. Cont. Educ. Pract. Vet. (1998) 20:509-515.

[32] Proudman C. J., Matthews J., Control of intestinal parasites in horses, In Pract. (2000) 22:90-97.

[33] Proudman C. J., Trees A. J., Correlation of antigen specific IgG and IgG(T) responses with *Anoplocephala perfoliata* infection intensity in the horse, Parasite Immunol. (1996) 18:499-506.

[34] Proudman C. J., Trees A. J., Use of excretory/secretory antigens for the serodiagnosis of *Anoplocephala perfoliata* cestodosis, Vet. Parasitol. (1996) 61:239-47.

[35] Reid S. W. J., Mair T. S., Hillyer M. H., Love, S., Epidemiologic risk-factors associated with a diagnosis of clinical cyathostomiasis in the horse, Equine Vet. J. (1995) 27:127-30.

[36] Reinemeyer C. R., Smith S. A., Gabel A. A., Herd R. P., The prevalence and intensity of internal parasites of horses in the USA, Vet. Parasitol. (1984) 15:75-83.

[37] Sambrook J., Fritsch E., Maniatis T., Molecular cloning: a laboratory manual, Cold Harbor Spring Laboratory Press, second edition, 1989.

[38] Shibui A., Takamoto M., Shi Y., Komiyama A., Sugane K., Cloning and characterization of a novel gene encoding keratin-like protein from nematode *Nippostrongylus brasiliensis*, BBA-Gene Structure and Expression (2001)

[40] Martin S. A. M, Thompson F. J, Devaney E, The construction of spliced leader cDNA libraries from the filarial nematode Brugia pahangi, Molecular and Biochemical Parasitology, (1995)

Additional immunoreactive clones: The following table lists additional sequences encoding immunoreactive cyathostomin antigens which were identified from the larval cDNA library, from two screenings which revealed distinct clones. The first immunoscreen (A) used serum from experimentally cyathostomin-infected ponies (from a previous study[1]), and the second immunoscreen (B) used a pool of sera from naturally infected horses; both groups had high parasite burdens. The antigens which have been checked for immunogenicity and cross specificity by recombinant bacterial expression are also indicated.

| Antigen | Number of clones per screen A | Number of clones per screen B | Closest homologues (Accession numbers in brackets) | Amino acid identity | Transcription pattern EL3 | Transcription pattern DL | Transcription pattern LP | Immuno-genicity | Cross specificity |
|---|---|---|---|---|---|---|---|---|---|
| Gut-associated larval antigen (GALA) | 15 | 1 | Keratin-like protein, *Nippostrongylus brasiliensis*, (BAB68205). | 35% over 128 a.a. | + | ++ | − | + | + |
|  |  |  | Keratin-like proteins, *Caenorhabditis elegans* (NP_502026 and NP_501448) | 34% over 104 a.a. |  |  |  |  |  |
| Glutathione-S-transferase (GST) | 1 | 0 | Cytosolic GST from *Oesophagostomum dentatum* (ACA30415) | 85% over 209 a.a. | − | + | + |  |  |
| Galectin-1 (GAL-1) | 1 | 0 | Galectin family member, *C. elegans* (NP_495163) | 83% over 279 a.a. | − | ++ | + |  |  |
| Galectin-2 (GAL-2) | 0 | 1 | Galectin family member, *Haemonchus contortus* (AAF63406) | 91% over 259 a.a. | + | ++ | ++ |  |  |
| Nematode polyprotein allergen/antigen (NPA) | 4 | 0 | NPA from *Dictyocaulus viviparus* (Q24702) | 42% over 314 a.a. | − | ++ | ++ |  |  |
| Cyathostomin immunodominant antigen-1 (CID-1) | 3 | 0 | EST from larval-stage *Necator americanus* (BG467549). Function of this is unknown. | 59% over 61 a.a. | − | ++ | ++ | + |  |
| Surface associated antigen (SAA) | 4 | 8 | SAA-2, *N. americanus* (ACE79378) | 71% over 146 a.a. | + | ++ | ++ |  |  |
| Fatty acid/retinol binding protein -1 (FAR-1) | 0 | 1 | Putative ES protein with FAR binding domain, *Ostertagia ostertagi* (CAD20464) | 45% over 100 a.a. | + | ++ | ++ |  |  |
| Fatty acid/retinol binding protein -2 (FAR-2) | 0 | 1 | FAR binding protein, *Ancylostoma ceylanicum* (ACC76809) | 72% over 160 a.a. | − | ++ | + |  |  |
| Globin (GLO) | 0 | 15 | Cuticle globin, from *Syngamus trachea* (AAL56426) | 54% over 161 a.a | + | ++ | ++ |  |  |
| Clone of unknown function -20a (Unk-20a) | 0 | 1 | No homology found | NA | − | ++ | ++ |  |  |
| Unk-46a | 0 | 1 | Third-stage larval EST, *N. brasiliensis* (EH359049) | 33% over 124 a.a. | − | ++ | ++ |  |  |
| Unk-50a | 0 | 1 | Hypothetical protein, *C. elegans* (NP_490737) | 33% over 140 a.a. | − | ++ | + |  |  |

[1] Murphy D., Love S., The pathogenic effects of experimental cyathostome infections in ponies, Vet. Parasitol. (1997) 70: 99-110.

Homologues of cyathostomin gut-associated larval antigen (Cy-GALA)

| Homologue | Amino acid identity to Cy-GALA-1 | Putative species |
|---|---|---|
| Cy-GALA-1 | — | *C. patemtum* |
| Cy-GALA-2 | 83.3 % | *C. nassatus* |
| Cy-GALA-3 | 77.7 % | *C. coronatus* |
| Cy-GALA-4 | 93.0 % | *C. catinatum* |

Sequences of a conserved region of GALA from individual cyathostomin species

| Species | Sequence | Number of individuals | Intraspecies aa identity range |
|---|---|---|---|
| C. ashworthi | LTFAEKKGKISEWAKKYNVVDEVASYNAYREKLKQEHRKNVS(E/V)LVSGLP(G/D)AVKKVN(E/V)LLD (SEQ ID NO: 68) | 4 | 90.0-100% |
| C. catinatum | LTFAEKK(E/K)EISEWAKKYNVVDEVASYNAYREKLKQEHRKNVSELVSALPNAVKKVNDLLD (SEQ ID NO: 69) | 10 | 91.7-100% |
| C. coronatus | LTFAEKKEKISEWAKKYKVEDEVASYNAYREKLKQEHRKNVSELVSALPGAVKKVNELLD (SEQ ID NO: 70) | 6 | 96.7-100% |

Sequences of a conserved region of GALA from individual cyathostomin species

| Species | Sequence | Number of individuals | Intraspecies aa identity range |
|---|---|---|---|
| C. goldi | LTFAEKKKEISEWAKKYNVVDEVASYNAYREKLKQEHRKNVSELVSDLPSAVKKVNDLLD (SEQ ID NO: 71) | 8 | 90.0-100% |
| C. labiatus | LTFAEKKEKISEWAKKYNVVDEVARYNAYREKLKQEYRKNVSELVSGLPNAVKKVNDLLD (SEQ ID NO: 72) | 1 | — |
| C. leptostomum | LTFAEKKGKISEWAKKYNVVDEVASYNAYREKLKQEHRKNVSELVSGLPGAVKKVNELLD (SEQ ID NO: 73) | 3 | 88.3-100% |
| C. longibursatus | LTFAEKKEEISKWAKKYNVVDEVASYNAYREKLKQEHRKNVSEIVSDLPNAVKKVNDLLD (SEQ ID NO: 74) | 5 | 91.7-100% |
| C. minutus | LTFAEKKEKISEWAKKYNVVDEVASYNAYREKLKQEHRKNVSQLVSALPNAVKKVNDLLD (SEQ ID NO: 75) | 1 | — |
| C. nassatus | LTFAEKKEKIGEWAKKYNVVDEVAXYNAYREKLKQEHRKNVSELVSGLPNAVKKVNELLD (SEQ ID NO: 76) | 6 | 88.3-100% |
| C. pateratum | LTFAEKK(K/E)EISEWAKKYNVVDEVASYNAYREKLKQEHRKNVSELVSALPNAVKKVNDLLD (SEQ ID NO: 77) | 6 | 93.3-100% |

The invention claimed is:

1. A method of diagnosing a *cyathostomin* infection in an animal, said method comprising the steps of:
   (a) contacting a sample with a *cyathostomin* larval antigen, wherein the *cyathostomin* larval antigen is at least 60% identical to the sequence of SEQ ID NO: 1; and
   (b) identifying a level of anti-*cyathostomin* larval antigen antibodies in the sample, wherein the anti-*cyathostomin* larval antigen antibodies bind to antigen comprising an immunogenic sequence at least 60% identical to the sequence of SEQ ID NO: 1; *wherein* a level of *anti-cyathostomin* larval antigen antibodies is indicative of the *cyathostomin* infection.

2. The method of claim 1, wherein the level of anti-*cyathostomin* larval antigen antibodies is evaluated relative to the level of anti-*cyathostomin* larval antigen antibodies present in a reference or control sample obtained from a healthy animal, an animal without a moderate or high mucosal burden of *cyathostomin* parasites, and/or an animal without larval cyathostominosis.

3. The method of claim 1, wherein the sample is contacted with a *cyathostomin* larval antigen comprising SEQ ID NO: 1.

4. The method of claim 1, wherein the *cyathostomin* larval antigen is bound, conjugated or immobilized on or to a suitable substrate.

5. The method of claim 1, wherein the sample is contacted with one or more agent(s) capable of binding:
   (a) a *cyathostomin* larval antigen comprising SEQ ID NO: 1; or
   (b) a *cyathostomin* larval antigen comprising an amino acid sequence at least 60% identical to the amino acid sequence of SEQ ID NO: 1.

6. The method of claim 5, wherein the binding agent(s) are bound, conjugated or immobilized on or to a suitable substrate.

7. The method of claim 1, wherein the animal is a member of the Equidae family.

8. The method of claim 1, wherein the animal is a horse.

9. The method of claim 1, wherein the sample is a biological sample selected from the group consisting of: whole blood, serum, plasma, saliva, sweat, semen, tissue biopsy, tissue scraping, tissue/organ wash/lavage, and fecal preparation.

10. The method of claim 3, wherein the *cyathostomin* larval antigen is bound, conjugated, or immobilized on or to a suitable substrate.

11. The method of claim 1, wherein the level of anti-*cyathostomin* larval antigen antibody is identified using an immunological detection technique.

12. The method of claim 11, wherein the immunological detection technique is selected from the group consisting of enzyme-linked immunosorbent assay (ELISA), Western blot, and dot blot.

* * * * *

UNITED STATES PATENT AND TRADEMARK OFFICE
CERTIFICATE OF CORRECTION

PATENT NO. : 8,663,939 B2  Page 1 of 1
APPLICATION NO. : 13/260935
DATED : March 4, 2014
INVENTOR(S) : Matthews et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this

Twenty-ninth Day of September, 2015

Michelle K. Lee
*Director of the United States Patent and Trademark Office*